US008324380B2

(12) United States Patent
Coats et al.

(10) Patent No.: US 8,324,380 B2
(45) Date of Patent: Dec. 4, 2012

(54) AMINO-HETEROARYL-CONTAINING PROKINETICIN 1 RECEPTOR ANTAGONISTS

(75) Inventors: Steven J. Coats, McDonough, GA (US); Alexey B. Dyatkin, Maple Glen, PA (US); Wei He, Audubon, PA (US); Joseph Lisko, Glenmoore, PA (US); Tamara A. Miskowski, Chalfont, PA (US); Janet L. Ralbovsky, Shelton, CT (US); Mark J. Schulz, Skippack, PA (US)

(73) Assignee: Janssen Pharmaceutica NV, Beerse (BE)

( * ) Notice: Subject to any disclaimer, the term of this patent is extended or adjusted under 35 U.S.C. 154(b) by 836 days.

(21) Appl. No.: 12/256,891

(22) Filed: Oct. 23, 2008

(65) Prior Publication Data
US 2009/0163505 A1 Jun. 25, 2009

Related U.S. Application Data

(60) Provisional application No. 60/983,638, filed on Oct. 30, 2007.

(51) Int. Cl.
C07D 251/30 (2006.01)
C07D 401/06 (2006.01)
C07D 401/14 (2006.01)
C07D 403/06 (2006.01)
C07D 403/14 (2006.01)
C07D 401/12 (2006.01)
C07D 403/12 (2006.01)
A61K 31/53 (2006.01)
A61P 1/12 (2006.01)
A61P 1/06 (2006.01)
A61P 1/00 (2006.01)

(52) U.S. Cl. ...................... 544/220; 514/241
(58) Field of Classification Search .................. 544/220; 514/241
See application file for complete search history.

(56) References Cited

U.S. PATENT DOCUMENTS 7,825,117 B2 * 11/2010 Mabus et al. ................. 514/241
7,902,358 B2 * 3/2011 Coats et al. ................... 544/223
7,968,710 B2 * 6/2011 Coats et al. ................... 544/223

FOREIGN PATENT DOCUMENTS

WO WO 2004/087054 A2 10/2004
WO WO 2006/104715 A1 10/2006

OTHER PUBLICATIONS

Freshney et al., Culture of Animal Cells, A Manual of Basic Technique, Alan R. Liss, Inc., 1983, New York, p. 4.*
Dermer et al., Bio/Technology, 1994, 12:320.*
Golub et al., Science, 286, 531-537, 1999.*
Powell et al., British Journal of Dermatology, 141 802-810, 1999.*
Cecil Textbook of Medicine, edited by Bennet, J.C., and Plum F., 20th edition, vol. 1, 1004-101 O, 1996.*
West, Anthony R., Solid State Chemistry and its Applications, Wiley, New York, 1988, pp. 358 & 365.*
Vippagunta et al., Advanced Drug Delivery Reviews 48: 3-26, 2001.*
Zhou et al., Molecular Interventions, vol. 6(6), 330-338, 2006.*
Akehurst, R. et al., "Treatment of irritable bowel syndrome: a review of randomized controlled trials", Gut 2001, 48:272-282.
Berge, S. et al., "Pharmaceutical Salts", Journal of Pharmaceutical Sciences, vol. 66, Issue 1, pp. 1-19, 1977.
Bullock, C. et al., "Structural determinants required for the bioactivities of prokineticins and identification of prokineticin receptor antagonists", Molecular Pharmacology, 2004, vol. 65 (3), pp. 582-588.
Goi, T. et al., "Angiogenesis and tumor proliferation/metastasis of human colorectal cancer cell line SW620 transfected with endocrine glands-derived-vascular endothelial growth factor, as a new angiogenic factor", Cancer Research, 2004, 64:1906-1910.
Gould, Philip L., "Salt selection for basic drugs", International Journal of Pharmaceutics, 1986, 33:201-217.
Jackson, J. et al., "Treatment of functional gastrointestinal disorders with antidepressant medications: a meta-analysis", American Journal of Medicine, 2000, 108:65-72.
Jailwala, J. et al., "Pharmacologic treatment of the irritable bowel syndrome: a systematic review of randomized, controlled trials", Ann. Intern. Med. 2000, 133:136-147.
LeCouter J. et al., "Identification of an angiogenic mitogen selective for endocrine gland endothelium", Nature 2001, 412:877-884.
LeCouter, J. et al., "The endocrine-gland-derived VEGF homologue Bv8 promotes angiogenesis in the testis: Localization of Bv8 receptors to endothelial cells" Proc. Natl. Acad. Sci., 2003, 100:2685-2690.
LeCouter, J. et al., "The role of EG-VEGF in the regulation of angiogenesis in endocrine glands", Cold Spring Harbor Symposia on Quantitative Biology, 2002, 67:217-221.
Li, M. et al., "Identification of two prokineticin cDNAs: recombinant proteins potently contract gastrointestinal smooth muscle", Molecular Pharmacology, 2001 59:692-698.
Masuda, Y. et al., "Isolation and identification of EG-VEGF/prokineticins as cognate ligands for two orphan G-protein-coupled receptors", Biochem. Biophys. Res. Comm., 2002, 293(1):396-402.
Mollay, C. et al., "Bv8, a small protein from frog skin and its homologue from snake venom induce hyperalgesia in rats", European Journal of Pharmacology, 1999, 374:189-196.

(Continued)

Primary Examiner — Venkataraman Balasubramanian

(57) ABSTRACT

The present invention relates to certain novel compounds of Formula (I):

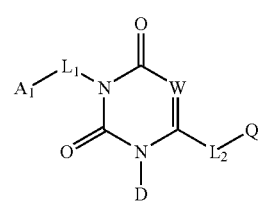

Formula (I)

and methods for preparing these compounds, compositions, intermediates and derivatives thereof and for the treatment of prokineticin 1 or prokinetin 1 receptor mediated disorders.

6 Claims, 5 Drawing Sheets

OTHER PUBLICATIONS

Negri, L. et al., "Bv8, the amphibian homologue of the mammalian prokineticins, modulates ingestive behaviour in rats" British Journal of Pharmacology, 2004, 142:181-191.

Negri, L. et al, "Nociceptive sensitization by the secretory protein Bv8", British Journal of Pharmacology, 2002, 137:1147-1154.

Poynard, T., et al., "Meta-analysis of smooth muscle relaxants in the treatment of irritable bowel syndrome", Aliment Pharmacol. Ther., 2001, 15:355-361.

Saito, Y., et al., "The epidemiology of irritable bowel syndrome in North America: a systematic review", The American Journal of Gastroenterology, 2002, 97:1910-1915.

Thompson, W. G., et al., "Functional bowel disorders in apparently healthy people", Gastroenterology, 1980, 79:283-288.

\* cited by examiner

Figure 1. Matrix Assisted Laser Desorption (MALDI) mass spectrum of protein mixture.

Figure 2. *Effect of Prokineticin 1 Peptide on Gut Mucosal Ion Transport ex vivo.*

AMINO-HETEROARYL-CONTAINING PROKINETICIN 1 RECEPTOR ANTAGONISTS

CROSS REFERENCE TO RELATED APPLICATIONS

This application claims priority to provisional application, U.S. Ser. No. 60/983,638, filed Oct. 30, 2007.

STATEMENT REGARDING FEDERALLY SPONSORED RESEARCH OR DEVELOPMENT

The research and development of the invention described below was not federally sponsored.

BACKGROUND OF THE INVENTION

Functional bowel disorders involve abnormal motility and secretion within organs of the gastrointestinal (GI) tract, and are characterized by abdominal discomfort/pain. The criteria for these disorders are summarized by gastroenterologists in the 'Rome II criteria'. Based on these criteria the disorders are common and include, but are not limited to, functional dyspepsia, irritable bowel syndrome (IBS), gastroesophageal reflux disease (GERD) and non-erosive reflux disease (NERD), and chronic constipation (including colonic inertia, idiopathic pseudoobstruction). GERD is extremely prevalent, is usually associated with non-cardiac chest pain and may be treated with acid-suppressing agents and prokinetic agents. IBS is characterized by the presence of reoccurring constipation and/or diarrhea, which can be associated with gaseous distention/bloating and abdominal discomfort/pain (Thompson, W. G. and Heaton, K. W. *Gastroenterology* 1980, 79, 283-288). The onset of the pain of IBS is associated with a change in the frequency and/or form of stool and can be relieved by defecation. IBS is an extremely prevalent condition that occurs to varying severity in 10-15% of the population (Saito, Y. A.; Schoenfeld, P.; and Locke, G. R. *Am. J. Gastroenterol.* 2002, 97, 1910-1915). The pain may be treated with smooth muscle relaxants and antidepressants (Jackson, J. L.; O'Malley, P. G.; Tomkins, G.; Balden, E.; Santoro, J.; and Kroenke, K.; *Am. J. Med.* 2000, 108, 65-72; Jailwala, J.; Imperiale, T. F.; and Kroenke, K.; *Ann. Intern. Med.* 2000, 133:136-147; Akehurst, R. and Kaltenthaler, E. *Gut* 2001, 48, 272-282; Poynard, T.; Regimbeau, C.; and Benhamou, Y.; *Aliment Pharmacol. Ther.* 2001, 15, 355-361). Severe diarrhea predominant IBS is treated by alosetron, whereas constipation predominant IBS is treated by tegaserod. Functional dyspepsia is a disorder of the upper GI tract with symptoms exacerbated by a meal and associated with early satiety, nausea and vomiting. Although its etiology is unknown, prokinetic agents may relieve the symptoms of IBS. In some patients there is overlap in symptoms between GERD/NERD, functional dyspepsia and IBS. Treatments for functional bowel disorders, such as IBS, have low efficacy and are associated with adverse effects. For example, alosetron is approved by the FDA on a risk management program because it is associated with an increase in a serious adverse event, ischemic colitis. No treatments effectively alleviate pain in functional bowel disorders.

In addition to functional disorders, inflammatory bowel diseases (IBD) are common and include ulcerative colitis (UC) and Crohn's disease (CD). Although there may be a genetic component to CD, the etiology of both CD and UC is unknown.

UC is a diffuse mucosal disease of the colon, characterized by inflammation and ulceration, which is associated with diarrhea and abdominal cramping. The mucosal inflammation progresses from the rectal area to eventually extend through the large bowel. CD is a transmural inflammation that most frequently involves the distal small bowel and colon. The inflammation can result in ulcers of varying involvement and in severe cases result in transmural scarring and chronic inflammation. Both infectious and dysregulated immune functions may contribute to disease onset. Therapies for IBD include corticosteroids, immunosuppressives (azathioprine, mercaptopurine, and methotrexate) and aminosalicylates (5-ASA). These therapies involve suppression of the immune system by mimicking corticoids, or unknown mechanisms of action. Oral corticosteroid use is associated with serious adverse effects, whereas immunosuppressives and aminosalicylates are only moderately effective. Infliximab (a chimeric monoclonal anti-tumor necrosis factor antibody) is effective in CD, however, its use is associated with the presence of antibodies, which reduce its efficacy. There are no treatments that target the motility and secretory abnormalities or painful sensation that are associated with gut inflammation.

The cysteine rich proteins known as Prokineticin 1 (PK1) and Prokineticin 2 (PK2), as well as variants, fragments and molecules having PK activity, have been identified. These have been shown to contract gastrointestinal smooth muscle (Li, M.; Bullock, C. M.; Knauer, D. J.; Ehlert, F. J.; and Zhou, Q. Y., *Mol. Pharmacol.* 2001, 59, 692-698), and suppress feeding (Negri, L.; Lattanzi, R.; Giannini, E.; De Felice, M.; Colucci, A. and Melchiorri, P. *Brit. J. Pharmacol.* 2004, 142, 181-191). PK1 and PK2 act on both PK1 and PK2 receptors, and limited structural changes of C-terminal cysteine-rich regions of these related PKs are tolerated. For example, chimeric PKs, where the cysteine-rich domains of PK 1 and PK 2 were exchanged between the two; and a splice variant of PK2 that included a 21 residue insertion in its C-terminal domain retained activity (Bullock, C M; Li J. D.; Zhou, Q. Y.; *Mol. Pharmacol.* 2004, 65(3), 582-8). A PK variant binds to receptors of primary sensory neurons, and results in an intense sensitization of peripheral nociceptors to thermal and mechanical stimuli (Mollay, C.; Weschelberger, C.; Mignogna, G.; Negri, L.; Melchiorri, P.; Barra, D.; Kreil, G.; *Eur. J. Pharmacol.* 1999, 374, 189-196; Negri, L.; Lattanzi, R.; Giannini, E.; Metere, A.; Colucci, M.; Barra, D.; Kreil, G.; Melchiorri, P.; Brit. *J. Pharmacol.* 2002, 137(8), 1147-54).

Patent application PCT/US2004/087054 A2 provides methods of modulating gastric acid or pepsinogen secretion by administering an amount of a prokineticin receptor antagonist effective to alter one or more indicia of gastric acid secretion.

PK1 induces proliferation, migration and fenestration in capillary endothelial cells derived from endocrine glands. The expression of PK mRNA is restricted to the steroidogenic glands, ovary, testis, adrenal and placenta (LeCouter, J.; Kowalski, J.; Foster, J.; Hass, P., Zhang, Z.; Dillard-Telm, L., Frantz, G., Rangell, L.; DeGuzman, L.; Keller, G. A.; Peale, F.; Gurney, A.; Hillan, K. J.; Ferrara, N. *Nature* 2001, 412 (6850), 877-84). In 2002 the identification of the PK1 receptor provided a novel molecular basis for the regulation of angiogenesis in endocrine glands (Masuda, Y.; Takatsu, Y.; Terao, Y.; Kumano, S.; Ishibashi, Y.; Suenaga, M.; Abe, M.; Fukusumi, S.; Watanabe, T.; Shintani, Y.; Yamada, T.; Hinuma, S.; Inatomi, N.; Ohtaki, T.; Onda, H.; Fujino, M.; *Biochem. Biophys. Res. Commun.* 2002, 293(1), 396-402; LeCouter, J.; Lin, R.; Ferrara, N.; *Cold Spring Harb Symp Quant Biol.* 2002, 67, 217-21). For example, adenoviral delivery of PK1 to the mouse testis results in a potent angiogenic response (LeCouter, J.; Lin, R.; Tejada, M.; Frantz, G.; Peale, F.; Hillan, K. J.; Ferrara, N. *Proc. Natl. Acad. Sci. USA.* 2003, 100, 2685-90). Recently, it was shown that PK1 mRNA is not normally expressed in colorectal normal mucosa but is detected in colorectal cancer cells (Goi, T.; Fujioka, M.; Satoh, Y.; Tabata, S.; Koneri, K.; Nagano, H.; Hirono, Y.; Katayama, K.; Hirose, K. and Yamaguchi., *Cancer Res.* 2004, 64, 1906-1910).

Prokineticin 1 receptor antagonists are useful in the treatment and prevention of various mammalian disease states, for example, visceral pain that is associated with IBS and IBD. Additionally, PK1 receptor antagonists are useful for the treatment of GERD or other forms of secretory diarrhea. Additionally, PK1 receptor antagonists are useful in treating cancer-specific angiogenesis factor in the large intestine and reproductive organs.

It is an object of the present invention to provide prokineticin 1 receptor antagonists. It is also an object of the invention to provide a method of treating or ameliorating a condition mediated by prokineticin 1 receptor. And, it is an object of the invention to provide a useful pharmaceutical composition comprising a compound of the present invention useful as a prokineticin 1 receptor antagonist.

SUMMARY OF THE INVENTION

The present invention is directed to a compound of Formula (I):

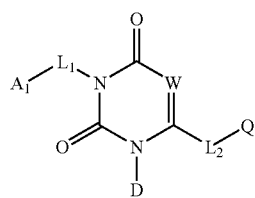

Formula (I)

$A_1$ is hydrogen, $C_{1-4}$alkoxy, aryl, aryloxy, optionally benzofused heterocyclyl, or an optionally benzofused heteroaryl; and aryl, aryloxy, heteroaryl, heterocyclyl, the benzo portion of benzofused heterocyclyl, and benzofused heteroaryl are optionally substituted with a substituent selected from the group consisting of $C_{1-6}$alkyl, hydroxy($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, $C_{1-6}$alkylamino, di($C_{1-6}$alkyl)amino, cyano, hydroxy, aminocarbonyl, $C_{1-6}$alkylaminocarbonyl, di($C_{1-6}$alkyl)aminocarbonyl, $C_{1-6}$alkoxycarbonylamino, $C_{1-6}$alkylcarbonyl, $C_{1-6}$alkylthiocarbonyl, formyl, $C_{1-6}$alkylsulfonyl, $C_{1-6}$alkylsulfonylamino, aminosulfonyl, $C_{1-6}$alkylaminosulfonyl, and di($C_{1-6}$alkyl)aminosulfonyl;

and wherein aryl, aryloxy, heteroaryl, heterocyclyl, the benzo portion of benzofused heterocyclyl, and benzofused heteroaryl are optionally further substituted with one to two substituents independently selected from the group consisting of $C_{1-4}$alkyl, $C_{1-4}$alkoxy, halogen, and hydroxy; provided that $A_1$ is other than 3,5-di-t-butyl-phenyl;

$L_1$ is —(CH$_2$)$_r$—, —CH$_2$C$_{2-4}$alkenyl-, or —CH$_2$CH$_2$X(CH$_2$)$_s$—, wherein $L_1$ is optionally substituted with one to two substituents independently selected from the group consisting of $C_{1-6}$alkyl, $C_{2-6}$alkenyl, $C_{2-6}$alkynyl, and halogen; and, r is an integer of 1 to 5; such that r is greater than or equal to 4 when $A_1$ is $C_{1-4}$alkoxy;

s is an integer of 1 to 3;
X is O or S;
D is —P-$A_2$;

wherein P is —(CH$_2$)$_{1-2}$— or —CH$_2$CH=CH— when $A_2$ is phenyl, optionally benzofused heterocyclyl, optionally benzofused heteroaryl, or $C_{3-8}$cycloalkyl; alternatively, P is —(CH$_2$)$_{3-6}$— when $A_2$ is hydrogen, $C_{1-4}$alkoxy, or $C_{1-4}$alkoxycarbonyl; and wherein P is optionally substituted with one to two substituents independently selected from the group consisting of $C_{1-6}$alkyl, $C_{2-6}$alkenyl, $C_{2-6}$alkynyl, and halogen;

$A_2$ is hydrogen; dihydrobenzofuranyl; heteroaryl other than unsubstituted pyridin-2-yl; $C_{3-8}$cycloalkyl; or phenyl optionally substituted at the meta and para positions with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, $C_{1-6}$alkylamino, di($C_{1-6}$alkyl)amino, cyano, hydroxy, nitro, $C_{1-6}$alkylcarbonyl, $C_{1-6}$alkylthiocarbonyl, aminocarbonyl, $C_{1-6}$alkylaminocarbonyl, di($C_{1-6}$alkyl)aminocarbonyl, $C_{1-6}$alkylcarbonylamino, and a non fused $C_{3-6}$cycloalkyloxy; wherein dihydrobenzofuranyl, heteroaryl, and $C_{3-8}$cycloalkyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, $C_{1-6}$alkylamino, di($C_{1-6}$alkyl)amino, cyano, hydroxy, nitro, $C_{1-6}$alkylcarbonyl, $C_{1-6}$alkylthiocarbonyl, aminocarbonyl, $C_{1-6}$alkylaminocarbonyl, di($C_{1-6}$alkyl)aminocarbonyl, $C_{1-6}$alkylcarbonylamino, and a non fused $C_{3-6}$cycloalkyloxy;

provided that no more than two substituents on $A_2$ are aryl($C_{1-6}$)alkoxy, phenyl, or a non fused $C_{3-6}$cycloalkyloxy;

such that both $A_1$ and $A_2$ are not 4-fluoro-phenyl when $L_1$ and $L_2$ are both —CH$_2$— and Q is a substituent of formula $Q_1$;

W is N or C($R_W$); wherein $R_W$ is H or $C_{1-2}$alkyl;

$L_2$ is a bivalent radical selected from the group consisting of
pyrrolidinyl or piperidinyl attached to the W-containing ring of Formula (I) via its nitrogen atom, wherein said pyrrolidinyl or piperidinyl is substituted on a carbon atom with —(CH$_2$)$_{0-2}$—;

—NH—C$_{5-7}$cycloalkyl-(CH$_2$)$_{0-2}$—; such that when C$_{5-7}$cycloalkyl is cyclohexyl, Q is attached at either the 2- or cis-4-position relative to the position of —NH—;

—C(=O)NH(CR$^y$R$^z$)$_{2-5}$—;
and
—NH—CH(R$^x$)—(CR$^y$R$^z$)$_{1-5}$—;

R$^x$, R$^y$, and R$^z$ are independently H or $C_{1-4}$alkyl;

and provided that $L_2$ in any instance does not exceed 7 atoms in length;

such that Q is selected from the group consisting of $Q_1$, $Q_2$, $Q_4$, and $Q_6$ when $L_2$ is other than —NH—CH(R$^x$)—(CR$^y$R$^z$)$_{1-5}$—;

Q is

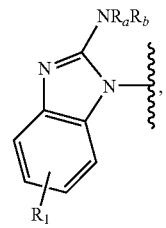

$Q_1$

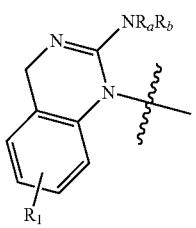

Q₂

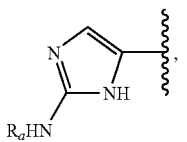

Q₃

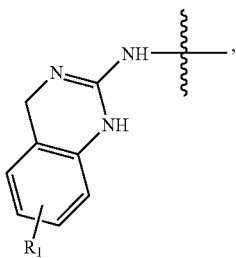

Q₄

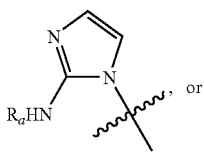

Q₅

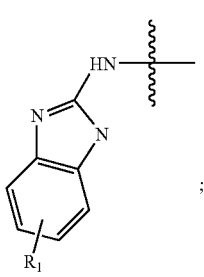

Q₆ wherein the benzo portion of Q₁, Q₂, Q₄ and Q₆ is optionally substituted with R₁;

R₁ is one to two substituents independently selected from the group consisting of hydrogen, C₁₋₄alkyl, C₁₋₄alkoxy, hydroxy, halogen, trifluoromethyl, and C₁₋₄alkylsulfonyl;

R_a and R_b are independently hydrogen, trifluoromethylcarbonyl, C₁₋₄alkylcarbonyl, and methyl;

and enantiomers, diastereomers, solvates, and pharmaceutically acceptable salts thereof.

DETAILED DESCRIPTION OF THE INVENTION

Figure 1:
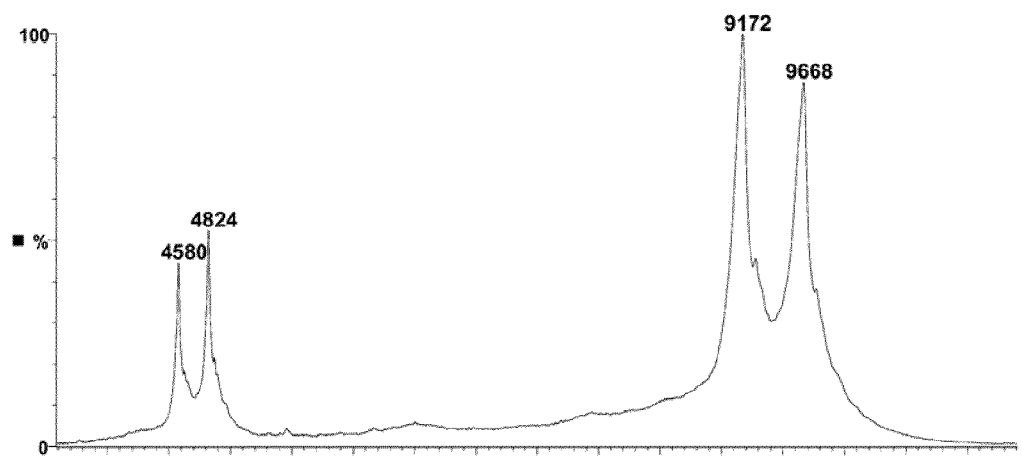
FIG. 1 shows a MALDI-TOF ANALYSIS of a Prokineticin-1 ligand preparation mixture. The mixture includes a four C-terminal residue truncated product (MW=9172), and a full-length prokineticin-1 ligand (MW=9668).

As used herein, the following terms are intended to have the following meanings:

"$C_{a-b}$" (where a and b are integers) refers to a radical containing from a to b carbon atoms inclusive. For example, $C_{1-3}$ denotes a radical containing 1, 2 or 3 carbon atoms.

With reference to substituents, the term "independently" means that when more than one of such substituent is possible, such substituents may be the same or different from each other. Therefore, designated numbers of carbon atoms (e.g. $C_{1-8}$) shall refer independently to the number of carbon atoms in an alkyl or cycloalkyl moiety or to the alkyl portion of a larger substituent in which alkyl appears as its prefix root.

As used herein, unless otherwise noted, "alkyl" whether used alone or as part of a substituent group refers to straight and branched carbon chains having 1 to 8 carbon atoms or any number within this range. The term "alkoxy" refers to an —Oalkyl substituent group, wherein alkyl is as defined supra. Similarly, the terms "alkenyl" and "alkynyl" refer to straight and branched carbon chains having 2 to 8 carbon atoms or any number within this range, wherein an alkenyl chain has at least one double bond in the chain and an alkynyl chain has at least one triple bond in the chain. An alkyl and alkoxy chain may be substituted on a carbon atom. In substituent groups with multiple alkyl groups such as (C₁₋₆alkyl)₂amino- the C₁₋₆alkyl groups of the dialkylamino may be the same or different.

"Halogenated alkyl" refers to a saturated branched or straight chain alkyl radical derived by removal of 1 hydrogen atom from the parent alkyl; the parent alkyl chain contains from 1 to 8 carbon atoms with 1 or more hydrogen atoms substituted with halogen atoms up to and including substitution of all hydrogen atoms with halogen. Preferred halogenated alkyl groups include trifluoromethyl substituted alkyls and perfluorinated alkyls; more preferred fluorinated alkyls include trifluoromethyl and difluoromethyl.

"Halogenated alkoxy" refers to a radical derived from a halogenated alkyl, radical attached to an oxygen atom with the oxygen atom having one open valence for attachment to a parent structure.

The term "cycloalkyl" refers to saturated or partially unsaturated, monocyclic or polycyclic hydrocarbon rings of from 3 to 20 carbon atom members (preferably from 3 to 14 carbon atom members). Examples of such rings include, and are not limited to, cyclopropyl, cyclobutyl, cyclopentyl, cyclohexyl, cycloheptyl or adamantyl. The term cycloalkyl includes a cycloalkyl ring fused to a benzene ring (benzo fused cycloalkyl), a 5 or 6 membered heteroaryl ring (containing one of O, S or N and, optionally, one additional nitrogen) to form a heteroaryl fused cycloalkyl.

The term "heterocyclyl" refers to a nonaromatic cyclic ring of 5 to 10 members in which 1 to 4 members are nitrogen or a nonaromatic cyclic ring of 5 to 10 members in which zero, one or two members are nitrogen and up to two members is oxygen or sulfur; wherein, optionally, the ring contains zero, one or two unsaturated bonds. The term heterocyclyl includes a heterocyclyl ring fused to a benzene ring (benzo fused heterocyclyl), a 5 or 6 membered heteroaryl ring (containing one of O, S or N and, optionally, one additional nitrogen), a 5 to 7 membered cycloalkyl or cycloalkenyl ring, a 5 to 7 membered heterocyclyl ring (of the same definition as above but absent the option of a further fused ring) or fused with the carbon of attachment of a cycloalkyl, cycloalkenyl or heterocyclyl ring to form a spiro moiety. For instant compounds of the invention, the carbon atom ring members that form the heterocyclyl ring are fully saturated. Other compounds of the invention may have a partially saturated heterocyclyl ring. Additionally, heterocyclyl includes a heterocyclic ring bridged to form bicyclic rings. Preferred partially saturated heterocyclyl rings may have from one to two double bonds. Such compounds are not considered to be fully aromatic and are not referred to as heteroaryl compounds. Examples of heterocyclyl groups include, and are not limited to, pyrrolinyl (including 2H-pyrrole, 2-pyrrolinyl or 3-pyrrolinyl), pyrrolidinyl, 2-imidazolinyl, imidazolidinyl, 2-pyrazolinyl, pyrazolidinyl, piperidinyl, morpholinyl, thiomorpholinyl and piperazinyl.

The term "aryl" refers to an unsaturated, aromatic monocyclic ring of 6 carbon members or to an unsaturated, aromatic polycyclic ring of from 10 to 14 carbon members. Examples of such aryl rings include, and are not limited to, phenyl, naphthalenyl or anthracenyl. Preferred aryl groups for the practice of this invention are phenyl and naphthalenyl.

The term "heteroaryl" refers to an aromatic ring of 5 or 6 members wherein the ring consists of carbon atoms and has at least one heteroatom member. Suitable heteroatoms include nitrogen, oxygen or sulfur. In the case of 5 membered rings, the heteroaryl ring contains one member of nitrogen, oxygen or sulfur and, in addition, may contain up to three additional nitrogens. In the case of 6 membered rings, the heteroaryl ring may contain from one to three nitrogen atoms. For the case wherein the 6 membered ring has three nitrogens, at most two nitrogen atoms are adjacent. The term heteroaryl includes a heteroaryl ring fused to a benzene ring (benzofused heteroaryl), a 5 or 6 membered heteroaryl ring (containing one of O, S or N and, optionally, one additional nitrogen), a 5 to 7 membered cycloalkyl ring or a 5 to 7 membered heterocyclic ring (as defined supra but absent the option of a further fused ring). Examples of heteroaryl groups include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl or pyrazinyl; fused heteroaryl groups include indolyl, isoindolyl, indolinyl, benzofuryl, benzothienyl, indazolyl, benzimidazolyl, benzthiazolyl, benzoxazolyl, benzisoxazolyl, benzothiadiazolyl, benzotriazolyl, quinolizinyl, quinolinyl, isoquinolinyl or quinazolinyl.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

The term "halogen" refers to fluorine, chlorine, bromine and iodine. Substituents that are substituted with multiple halogens are substituted in a manner that provides compounds, which are stable.

The term "oxo" whether used alone or as part of a substituent group refers to an O= to either a carbon or a sulfur atom. For example, phthalimide and saccharin are examples of compounds with oxo substituents.

Whenever the term "alkyl" or "aryl" or either of their prefix roots appear in a name of a substituent (e.g., arylalkyl, alkylamino) it shall be interpreted as including those limitations given above for "alkyl" and "aryl." Designated numbers of carbon atoms (e.g., $C_1$-$C_6$) shall refer independently to the number of carbon atoms in an alkyl moiety or to the alkyl portion of a larger substituent in which alkyl appears as its prefix root. For alkyl, and alkoxy substituents the designated number of carbon atoms includes all of the independent member included in the range specified individually and all the combination of ranges within in the range specified. For example $C_{1-6}$ alkyl would include methyl, ethyl, propyl, butyl, pentyl and hexyl individually as well as sub-combinations thereof (e.g. $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As used herein, the term "acyl" refers to alkylcarbonyl substituents.

Throughout this disclosure, the terminal portion of the designated side chain is described first, followed by the adjacent functionality toward the point of attachment. Thus, for example, a "phenyl($C_{1-6}$)alkylaminocarbonyl($C_{1-6}$)alkyl" substituent refers to a group of the formula

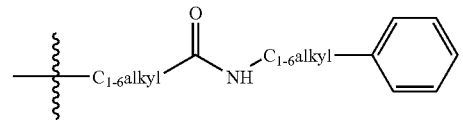

Embodiments of the present invention include compounds of Formula (I) wherein:
a) $A_1$ is phenyl, benzofused heterocyclyl wherein the point of attachment to $L_1$ is at the benzo ring, or benzofused heteroaryl; wherein phenyl, the benzo portion of benzofused heterocyclyl, and benzofused heteroaryl are optionally substituted with a substituent selected from the group consisting of $C_{1-4}$alkyl, hydroxy($C_{1-4}$)alkyl, $C_{1-4}$alkoxy, fluoro, chloro, halogenated $C_{1-4}$alkyl, halogenated $C_{1-4}$alkoxy, $C_{1-4}$alkylthio, $C_{1-4}$alkoxycarbonyl, amino, $C_{1-4}$alkylamino, di($C_{1-4}$alkyl)amino, cyano, hydroxy, aminocarbonyl, $C_{1-4}$alkylaminocarbonyl, di($C_{1-4}$alkyl)aminocarbonyl, $C_{1-4}$alkoxycarbonylamino, $C_{1-4}$alkylcarbonyl, $C_{1-4}$alkylthiocarbonyl, formyl, $C_{1-4}$alkylsulfonyl, $C_{1-4}$alkylsulfonylamino, aminosulfonyl, $C_{1-4}$alkylaminosulfonyl, and di($C_{1-4}$alkyl)aminosulfonyl; and wherein phenyl, the benzo portion of benzofused heterocyclyl, and benzofused heteroaryl are optionally further substituted with one to two substituents independently selected from the group consisting of $C_{1-4}$alkyl, $C_{1-4}$alkoxy, fluoro, chloro, and hydroxy; provided that $A_1$ is other than 3,5-di-t-butylphenyl;
b) $A_1$ is phenyl, benzofused heterocyclyl wherein the point of attachment to $L_1$ is at the benzo ring, or benzofused heteroaryl; wherein phenyl, the benzo portion of benzofused heterocyclyl, and benzofused heteroaryl are optionally substituted with a substituent selected from the group consisting of $C_{1-4}$alkyl, hydroxy($C_{1-4}$)alkyl, $C_{1-4}$alkoxy, fluoro, chloro, trifluoromethyl, trifluoromethoxy, $C_{1-4}$alkylthio, and hydroxy; and wherein phenyl, the benzo portion of benzofused heterocyclyl, and benzofused heteroaryl are optionally further substituted with one to two substituents independently selected from the group consisting of $C_{1-4}$alkyl, $C_{1-4}$alkoxy, fluoro, chloro, and hydroxy; and wherein phenyl, the benzo portion of benzofused heterocyclyl, and benzofused heteroaryl are optionally further substituted with a fluoro or chloro substituent; provided that $A_1$ is other than 3,5-di-t-butyl-phenyl;

c) $A_1$ is phenyl, benzofused heterocyclyl wherein the point of attachment to $L_1$ is at the benzo ring, or benzofused heteroaryl; wherein phenyl, the benzo portion of benzofused heterocyclyl, and benzofused heteroaryl are optionally substituted with a substituent selected from the group consisting of $C_{1-4}$alkyl, hydroxy($C_{1-4}$)alkyl, $C_{1-4}$alkoxy, fluoro, chloro, trifluoromethyl, trifluoromethoxy, $C_{1-4}$alkylthio, and hydroxy; and wherein phenyl, the benzo portion of benzofused heterocyclyl, and benzofused heteroaryl are optionally further substituted with a fluoro or chloro substituent;

d) $A_1$ is phenyl, 2,3-dihydro-benzofuranyl wherein the point of attachment to $L_1$ is at the benzo ring, or 1-methyl-benzotriazol-5-yl; wherein phenyl is optionally substituted with a substituent selected from the group consisting of $C_{1-2}$alkyl, $C_{1-2}$alkoxy, fluoro, chloro, and $C_{1-2}$alkylthio; and wherein phenyl is optionally further substituted with a fluoro or chloro substituent;

e) $A_1$ is 4-ethyl-phenyl, 3,4-dichloro-phenyl, 4-fluoro-phenyl, 4-chloro-phenyl, 4-methylthio-phenyl, 2,3-dihydro-benzofuran-5-yl, or 1-methyl-benzotriazol-5-yl;

f) $L_1$ is —$(CH_2)_r$—, optionally substituted with one to three substituents independently selected from the group consisting of $C_{1-6}$alkyl, $C_{2-6}$alkenyl, $C_{2-6}$alkynyl, and halogen; provided that when $A_1$ is hydrogen, r is greater than or equal to 4;

g) $L_1$ is —$(CH_2)_r$—, optionally substituted with a substituent selected from the group consisting of $C_{1-4}$alkyl, $C_{2-4}$alkenyl, and $C_{2-4}$alkynyl, provided that r is 1 to 3 when $A_1$ is other than hydrogen; or r is greater than or equal to 4 when $A_1$ is hydrogen;

h) $L_1$ is —$(CH_2)_r$— optionally substituted with a substituent selected from the group consisting of methyl and allyl, provided that r is 1 to 3 when $A_1$ is other than hydrogen;

i) $L_1$ is —$CH_2$—;

j) P is —$CH_2$— or —$CH_2CH=CH$—;

k) P is —$CH_2$—;

l) $A_2$ is hydrogen, heteroaryl other than unsubstituted pyridin-2-yl, dihydrobenzofuranyl, or phenyl optionally substituted at the meta and para positions with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, cyano, hydroxy, nitro, aminocarbonyl, $C_{1-6}$alkylcarbonylamino, and a non fused $C_{3-6}$cycloalkyloxy; wherein heteroaryl other than unsubstituted pyridin-2-yl and dihydrobenzofuranyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, cyano, hydroxy, nitro, aminocarbonyl, $C_{1-6}$alkylcarbonylamino, and a non fused $C_{3-6}$cycloalkyloxy;

provided that no more than two substituents on $A_2$ are aryl($C_{1-6}$)alkoxy, phenyl, or a non fused $C_{3-6}$cycloalkyloxy;

m) $A_2$ is heteroaryl other than unsubstituted pyridin-2-yl, dihydrobenzofuranyl, or phenyl optionally substituted at the meta and para positions with one to three substituents independently selected from the group consisting of $C_{1-6}$alkyl, $C_{1-6}$alkoxy, halogen, halogenated $C_{1-6}$alkyl, halogenated $C_{1-6}$alkoxy, $C_{1-6}$alkylthio, $C_{1-6}$alkoxycarbonyl, amino, hydroxy, nitro, aminocarbonyl, $C_{1-6}$alkylcarbonylamino, and a non fused $C_{3-6}$cycloalkyloxy; wherein heteroaryl other than unsubstituted pyridin-2-yl and dihydrobenzofuranyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, $C_{1-6}$alkylthio, $C_{1-6}$alkoxycarbonyl, amino, hydroxy, nitro, aminocarbonyl, $C_{1-6}$alkylcarbonylamino, and a non fused $C_{3-6}$cycloalkyloxy; provided that no more than two substituents on $A_2$ are non fused $C_{3-6}$cycloalkyloxy;

n) $A_2$ is furanyl, pyridin-3-yl, pyridin-4-yl, or phenyl optionally substituted at the meta and para positions with one to three substituents independently selected from the group consisting of $C_{1-4}$alkyl, $C_{1-4}$alkoxy, halogen, halogenated $C_{1-3}$alkoxy, $C_{1-3}$alkylthio, hydroxy, amino, aminocarbonyl, $C_{1-3}$alkylcarbonylamino, and a non fused $C_{3-6}$cycloalkyloxy; and wherein furanyl, pyridin-3-yl, and pyridin-4-yl are optionally substituted with one to three substituents independently selected from the group consisting of $C_{1-4}$alkyl, $C_{1-4}$alkoxy, halogen, halogenated $C_{1-3}$alkoxy, $C_{1-3}$alkylthio, hydroxy, amino, aminocarbonyl, $C_{1-3}$alkylcarbonylamino, and a non fused $C_{3-6}$cycloalkyloxy;

provided that no more than two substituents on $A_2$ are non fused $C_{3-6}$cycloalkyloxy;

o) $A_2$ is pyridin-3-yl pyridin-4-yl, or phenyl optionally substituted at the meta and para positions with one to two substituents independently selected from the group consisting of methyl, ethyl, methoxy, ethoxy, isopropyloxy, trifluoromethoxy, difluoromethoxy, hydroxy, aminocarbonyl, and methylcarbonylamino; wherein pyridin-3-yl and pyridin-4-yl are optionally substituted with one to two substituents independently selected from the group consisting of methyl, ethyl, methoxy, ethoxy, isopropyloxy, trifluoromethoxy, difluoromethoxy, hydroxy, aminocarbonyl, and methylcarbonylamino;

p) $A_2$ is phenyl substituted at the para position with a substituent selected from the group consisting of methoxy, ethoxy, isopropyloxy, difluoromethoxy, hydroxy, and aminocarbonyl; or $A_2$ is pyridin-3-yl or pyridin-4-yl substituted with methoxy;

q) W is N or $C(R_w)$ wherein $R_w$ is H;

r) W is N;

s) $L_2$ is a bivalent radical selected form the group consisting of —C(=O)NH$(CR^yR^z)_{2-5}$— and —NH—CH$(R^x)$—$(CR^yR^z)_{1-5}$—;

wherein $R^x$, $R^y$, and $R^z$ are independently H or $C_{1-4}$alkyl; and provided that $L_2$ in any instance does not exceed 7 atoms in length; such that Q is selected from the group consisting of $Q_1$, $Q_2$, $Q_4$, and $Q_6$ when $L_2$ is other than —NH—CH$(R^x)$—$(CR^yR^z)_{1-5}$—;

t) L$_2$ is a bivalent radical selected form the group consisting of —NH—CH(R$^x$)—(CR$^y$R$^z$)$_{1-5}$—;
  wherein R$^x$, R$^y$, and R$^z$ are independently H or C$_{1-4}$alkyl;
  and provided that L$_2$ in any instance does not exceed 7 atoms in length;
u) L$_2$ is a bivalent radical selected form the group consisting of —NH—CH(R$^x$)—(CR$^y$R$^z$)—;
  wherein R$^x$, R$^y$, and R$^z$ are independently H or C$_{1-4}$alkyl;
v) L$_2$ is a bivalent radical selected form the group consisting of —NH—CH$_2$CH$_2$—; wherein R$^x$, R$^y$, and R$^z$ are each H;
w) Q is

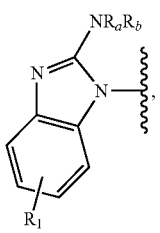  Q$_1$

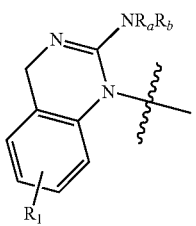  Q$_2$

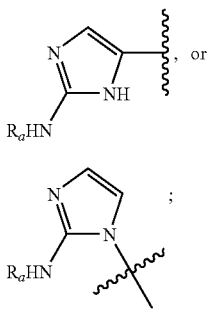  Q$_3$, or Q$_5$ x) Q is

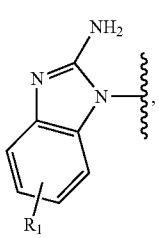  Q$_1$

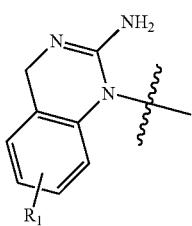  Q$_2$

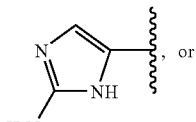  Q$_3$, or

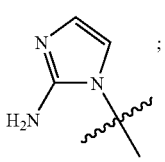  Q$_5$;

wherein R$_a$ and R$_b$ are each hydrogen;
y) R$_1$ is one to two substituents independently selected from the group consisting of hydrogen, methyl, methoxy, fluoro, chloro, and trifluoromethyl;
z) R$_1$ is one to two substituents wherein one substituent is selected from the group consisting of hydrogen, methyl, methoxy, fluoro, chloro, and trifluoromethyl; and the second substituent is hydrogen, fluoro, or chloro;
aa) R$_1$ is a substituent selected from hydrogen, fluoro, or chloro;
bb) R$_a$ is hydrogen, trifluoromethylcarbonyl, methylcarbonyl, or t-butylcarbonyl; and R$_b$ is hydrogen;
cc) R$_a$ and R$_b$ are each hydrogen;
and any combination of embodiments a) through cc) above, provided that it is understood that combinations in which different embodiments of the same substituent would be combined are excluded.

An embodiment of the present invention is directed to a compound of Formula (I) wherein:
A$_1$ is phenyl, benzofused heterocyclyl wherein the point of attachment to L$_1$ is at benzo ring, or benzofused heteroaryl; wherein phenyl, the benzo portion of benzofused heterocyclyl, and benzofused heteroaryl are optionally substituted with a substituent selected from the group consisting of C$_{1-4}$alkyl, hydroxy(C$_{1-4}$)alkyl, C$_{1-4}$alkoxy, fluoro, chloro, halogenated C$_{1-4}$alkyl, halogenated C$_{1-4}$alkoxy, C$_{1-4}$alkylthio, C$_{1-4}$alkoxycarbonyl, amino, C$_{1-4}$alkylamino, di(C$_{1-4}$alkyl)amino, cyano, hydroxy, aminocarbonyl, C$_{1-4}$alkylaminocarbonyl, di(C$_{1-4}$alkyl)aminocarbonyl, C$_{1-4}$alkoxycarbonylamino, C$_{1-4}$alkylcarbonyl, C$_{1-4}$alkylthiocarbonyl, formyl, C$_{1-4}$alkylsulfonyl, C$_{1-4}$alkylsulfonylamino, aminosulfonyl, C$_{1-4}$alkylaminosulfonyl, and di(C$_{1-4}$alkyl)aminosulfonyl; and wherein phenyl, the benzo portion of benzofused heterocyclyl, and benzofused heteroaryl are optionally further substituted with one to two substituents independently selected from the group consisting of C$_{1-4}$alkyl, C$_{1-4}$alkoxy, fluoro, chloro, and hydroxy; provided that A$_1$ is other than 3,5-di-t-butyl-phenyl;
L$_1$ is —(CH$_2$)$_r$—, optionally substituted with one to three substituents independently selected from the group consisting of C$_{1-6}$alkyl, C$_{2-6}$alkenyl, C$_{2-6}$alkynyl, and halogen; provided that when A$_1$ is hydrogen, r is greater than or equal to 4;
D is —P-A$_2$;
P is —CH$_2$— or —CH$_2$CH═CH—;
A$_2$ is hydrogen, heteroaryl other than unsubstituted pyridin-2-yl, dihydrobenzofuranyl, or phenyl optionally substituted at the meta and para positions with one to three substituents independently selected from the group consisting of C$_{1-6}$alkyl, C$_{1-6}$alkoxy, halogen, halogenated C$_{1-6}$alkyl, halogenated C$_{1-6}$alkoxy, aryl(C$_{1-6}$)alkoxy, phenyl, $C_{1-6}$alkylthio, $C_{1-6}$alkoxycarbonyl, amino, cyano, hydroxy, nitro, aminocarbonyl, $C_{1-6}$alkylcarbonylamino, and a non fused $C_{3-6}$cycloalkyloxy; wherein heteroaryl other than unsubstituted pyridin-2-yl and dihydrobenzofuranyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, cyano, hydroxy, nitro, aminocarbonyl, $C_{1-6}$alkylcarbonylamino, and a non fused $C_{3-6}$cycloalkyloxy;

provided that no more than two substituents on $A_2$ are aryl ($C_{1-6}$)alkoxy, phenyl, or a non fused $C_{3-6}$cycloalkyloxy;

W is N or $C(R_w)$ wherein $R_w$ is H;

$L_2$ is a bivalent radical selected form the group consisting of —C(=O)NH(CR$^y$R$^z$)$_{2-5}$— and —NH—CH(R$^x$)—(CR$^y$R$^z$)$_{1-5}$—;

wherein R$^x$, R$^y$, and R$^z$ are independently H or $C_{1-4}$alkyl; such that Q is selected from the group consisting of $Q_1$, $Q_2$, $Q_4$, and $Q_6$ when $L_2$ is other than —NH—CH(R$^x$)—(CR$^y$R$^z$)$_{1-5}$—;

and provided that $L_2$ in any instance does not exceed 7 atoms in length;

Q is

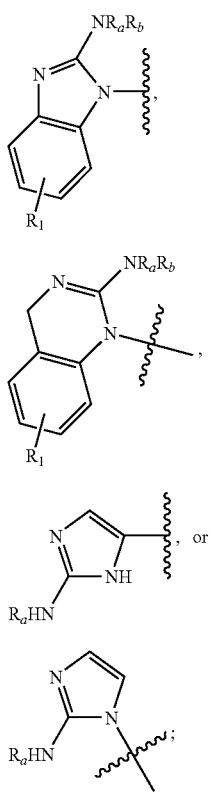

$R_1$ is one to two substituents independently selected from the group consisting of hydrogen, methyl, methoxy, fluoro, chloro, and trifluoromethyl;

$R_a$ is hydrogen, trifluoromethylcarbonyl, methylcarbonyl, or t-butylcarbonyl; and $R_b$ is hydrogen;

and enantiomers, diastereomers, solvates, and pharmaceutically acceptable salts thereof.

A further embodiment of the present invention is directed to a compound of Formula (I) wherein:

$A_1$ is phenyl, benzofused heterocyclyl wherein the point of attachment to $L_1$ is at the benzo ring, or benzofused heteroaryl; wherein phenyl, the benzo portion of benzofused heterocyclyl, and benzofused heteroaryl are optionally substituted with a substituent selected from the group consisting of $C_{1-4}$alkyl, hydroxy($C_{1-4}$)alkyl, $C_{1-4}$alkoxy, fluoro, chloro, trifluoromethyl, trifluoromethoxy, $C_{1-4}$alkylthio, and hydroxy; and wherein phenyl, the benzo portion of benzofused heterocyclyl, and benzofused heteroaryl are optionally further substituted with one to two substituents independently selected from the group consisting of $C_{1-4}$alkyl, $C_{1-4}$alkoxy, fluoro, chloro, and hydroxy; and wherein phenyl, the benzo portion of benzofused heterocyclyl, and benzofused heteroaryl are optionally further substituted with a fluoro or chloro substituent; provided that $A_1$ is other than 3,5-di-t-butyl-phenyl;

$L_1$ is —(CH$_2$)$_r$—, optionally substituted with one to three substituents independently selected from the group consisting of $C_{1-6}$alkyl, $C_{2-6}$alkenyl, $C_{2-6}$alkynyl, and halogen; provided that when $A_1$ is hydrogen, r is greater than or equal to 4;

D is —P-$A_2$;

P is —CH$_2$— or —CH$_2$CH=CH—;

$A_2$ is heteroaryl other than unsubstituted pyridin-2-yl, dihydrobenzofuranyl, or phenyl optionally substituted at the meta and para positions with one to three substituents independently selected from the group consisting of $C_{1-6}$alkyl, $C_{1-6}$alkoxy, halogen, halogenated $C_{1-6}$alkyl, halogenated $C_{1-6}$alkoxy, $C_{1-6}$alkylthio, $C_{1-6}$alkoxycarbonyl, amino, hydroxy, nitro, aminocarbonyl, $C_{1-6}$alkylcarbonylamino, and a non fused $C_{3-6}$cycloalkyloxy; wherein heteroaryl other than unsubstituted pyridin-2-yl and dihydrobenzofuranyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, $C_{1-6}$alkylthio, $C_{1-6}$alkoxycarbonyl, amino, hydroxy, nitro, aminocarbonyl, $C_{1-6}$alkylcarbonylamino, and a non fused $C_{3-6}$cycloalkyloxy; provided that no more than two substituents on $A_2$ are non fused $C_{3-6}$cycloalkyloxy;

W is N or $C(R_W)$ wherein $R_W$ is H;

$L_2$ is a bivalent radical selected form the group consisting of —C(=O)NH(CR$^y$R$^z$)$_{2-5}$— and —NH—CH(R$^x$)—(CR$^y$R$^z$)$_{1-5}$—;

wherein R$^x$, R$^y$, and R$^z$ are independently H or $C_{1-4}$alkyl;

and provided that $L_2$ in any instance does not exceed 7 atoms in length;

Q is

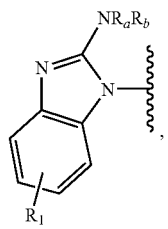

-continued

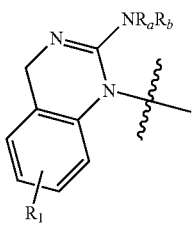
Q₂

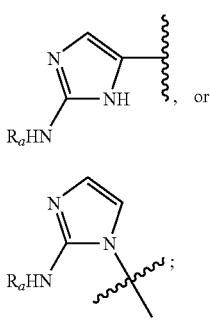
Q₃ or Q₅

R₁ is one to two substituents independently selected from the group consisting of hydrogen, methyl, methoxy, fluoro, chloro, and trifluoromethyl;
R_a is hydrogen, trifluoromethylcarbonyl, methylcarbonyl, or t-butylcarbonyl; and R_b is hydrogen;
and enantiomers, diastereomers, solvates, and pharmaceutically acceptable salts thereof.

A further embodiment of the present invention is directed to a compound of Formula (I) wherein:
$A_1$ is phenyl, benzofused heterocyclyl wherein the point of attachment to $L_1$ is at the benzo ring, or benzofused heteroaryl; wherein phenyl, the benzo portion of benzofused heterocyclyl, and benzofused heteroaryl are optionally substituted with a substituent selected from the group consisting of $C_{1-4}$alkyl, hydroxy($C_{1-4}$)alkyl, $C_{1-4}$alkoxy, fluoro, chloro, trifluoromethyl, trifluoromethoxy, $C_{1-4}$alkylthio, and hydroxy; and wherein phenyl, the benzo portion of benzofused heterocyclyl, and benzofused heteroaryl are optionally further substituted with a fluoro or chloro substituent;
$L_1$ is —(CH₂)_r—, optionally substituted with a substituent selected from the group consisting of $C_{1-4}$alkyl, $C_{2-4}$alkenyl, and $C_{2-4}$alkynyl, provided that r is 1 to 3 when $A_1$ is other than hydrogen; or r is greater than or equal to 4 when $A_1$ is hydrogen;
D is —P-A₂;
P is —CH₂—;
A₂ is furanyl, pyridin-3-yl, pyridin-4-yl, or phenyl optionally substituted at the meta and para positions with one to three substituents independently selected from the group consisting of $C_{1-4}$alkyl, $C_{1-4}$alkoxy, halogen, halogenated $C_{1-3}$alkoxy, $C_{1-3}$alkylthio, hydroxy, amino, aminocarbonyl, $C_{1-3}$alkylcarbonylamino, and a non fused $C_{3-6}$cycloalkyloxy; and wherein furanyl, pyridin-3-yl, and pyridin-4-yl are optionally substituted with one to three substituents independently selected from the group consisting of $C_{1-4}$alkyl, $C_{1-4}$alkoxy, halogen, halogenated $C_{1-3}$alkoxy, $C_{1-3}$alkylthio, hydroxy, amino, aminocarbonyl, $C_{1-3}$alkylcarbonylamino, and a non fused $C_{3-6}$cycloalkyloxy;
provided that no more than two substituents on A₂ are non fused $C_{3-6}$cycloalkyloxy;

W is N;
L₂ is a bivalent radical selected form the group consisting of
—NH—CH(R^x)—(CR^yR^z)_{1-5}—;
wherein R^x, R^y, and R^z are independently H or $C_{1-4}$alkyl;
and provided that L₂ in any instance does not exceed 7 atoms in length;
Q is

Q₁

Q₂

Q₃ or

Q₅ wherein R_a and R_b are each hydrogen;
R₁ is one to two substituents wherein one substituent is selected from the group consisting of hydrogen, methyl, methoxy, fluoro, chloro, and trifluoromethyl; and the second substituent is hydrogen, fluoro, or chloro;
and enantiomers, diastereomers, solvates, and pharmaceutically acceptable salts thereof.

A further embodiment of the present invention is directed to a compound of Formula (I) wherein:
$A_1$ is phenyl, benzofused heterocyclyl wherein the point of attachment to $L_1$ is at the benzo ring, or benzofused heteroaryl; wherein phenyl, the benzo portion of benzofused heterocyclyl, and benzofused heteroaryl are optionally substituted with a substituent selected from the group consisting of $C_{1-4}$alkyl, hydroxy($C_{1-4}$)alkyl, $C_{1-4}$alkoxy, fluoro, chloro, trifluoromethyl, trifluoromethoxy, $C_{1-4}$alkylthio, and hydroxy; and wherein phenyl, the benzo portion of benzofused heterocyclyl, and benzofused heteroaryl are optionally further substituted with a fluoro or chloro substituent;
$L_1$ is —(CH₂)_r—, optionally substituted with a substituent selected from the group consisting of $C_{1-4}$alkyl, $C_{2-4}$alkenyl, and $C_{2-4}$alkynyl, provided that r is 1 to 3 when $A_1$ is other than hydrogen; or r is greater than or equal to 4 when $A_1$ is hydrogen;

D is —P-A$_2$;
P is —CH$_2$—;
A$_2$ is furanyl, pyridin-3-yl, pyridin-4-yl, or phenyl optionally substituted at the meta and para positions with one to three substituents independently selected from the group consisting of C$_{1-4}$alkyl, C$_{1-4}$alkoxy, halogen, halogenated C$_{1-3}$alkoxy, C$_{1-3}$alkylthio, hydroxy, amino, aminocarbonyl, C$_{1-3}$alkylcarbonylamino, and a non fused C$_{3-6}$cycloalkyloxy; and wherein furanyl, pyridin-3-yl, and pyridin-4-yl are optionally substituted with one to three substituents independently selected from the group consisting of C$_{1-4}$alkyl, C$_{1-4}$alkoxy, halogen, halogenated C$_{1-3}$alkoxy, C$_{1-3}$alkylthio, hydroxy, amino, aminocarbonyl, C$_{1-3}$alkylcarbonylamino, and a non fused C$_{3-6}$cycloalkyloxy;
provided that no more than two substituents on A$_2$ are non fused C$_{3-6}$cycloalkyloxy;
W is N;
L$_2$ is a bivalent radical selected form the group consisting of —NH—CH(R$^x$)—(CR$^y$R$^z$)—;
wherein R$^x$, R$^y$, and R$^z$ are independently H or C$_{1-4}$alkyl;
Q is

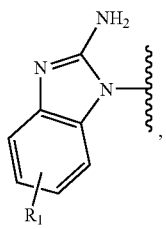

Q$_1$

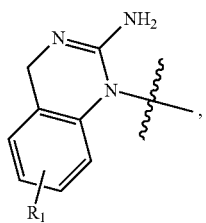

Q$_2$

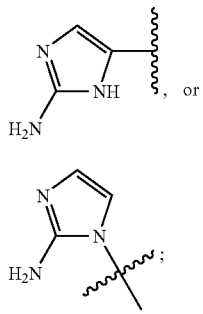

Q$_3$, or

Q$_5$ wherein R$_a$ and R$_b$ are each hydrogen;
R$_1$ is one to two substituents wherein one substituent is selected from the group consisting of hydrogen, methyl, methoxy, fluoro, chloro, and trifluoromethyl; and the second substituent is hydrogen, fluoro, or chloro;
and enantiomers, diastereomers, solvates, and pharmaceutically acceptable salts thereof.

A further embodiment of the present invention is directed to a compound of Formula (I) wherein:
A$_1$ is phenyl, 2,3-dihydro-benzofuranyl wherein the point of attachment to L$_1$ is at the benzo ring, or 1-methyl-benzotriazol-5-yl; wherein phenyl is optionally substituted with a substituent selected from the group consisting of C$_{1-2}$alkyl, C$_{1-2}$alkoxy, fluoro, chloro, and C$_{1-2}$alkylthio; and wherein phenyl is optionally further substituted with a fluoro or chloro substituent;
L$_1$ is —(CH$_2$)$_r$— optionally substituted with a substituent selected from the group consisting of methyl and allyl, provided that r is 1 to 3 when A$_1$ is other than hydrogen;
D is —P-A$_2$;
P is —CH$_2$—;
A$_2$ is pyridin-3-yl pyridin-4-yl, or phenyl optionally substituted at the meta and para positions with one to two substituents independently selected from the group consisting of methyl, ethyl, methoxy, ethoxy, isopropyloxy, trifluoromethoxy, difluoromethoxy, hydroxy, aminocarbonyl, and methylcarbonylamino; wherein pyridin-3-yl and pyridin-4-yl are optionally substituted with one to two substituents independently selected from the group consisting of methyl, ethyl, methoxy, ethoxy, isopropyloxy, trifluoromethoxy, difluoromethoxy, hydroxy, aminocarbonyl, and methylcarbonylamino;
W is N;
L$_2$ is a bivalent radical selected form the group consisting of —NH—CH$_2$CH$_2$—; wherein R$^x$, R$^y$, and R$^z$ are each H;
Q is

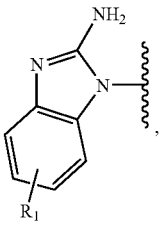

Q$_1$

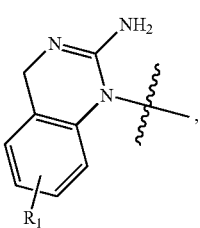

Q$_2$

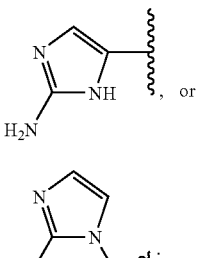

Q$_3$, or

Q$_5$ wherein R$_a$ and R$_b$ are each hydrogen;
R$_1$ is a substituent selected from hydrogen, fluoro, or chloro;
and enantiomers, diastereomers, solvates, and pharmaceutically acceptable salts thereof.

A further embodiment of the present invention is directed to a compound of Formula (I) wherein:
A$_1$ is 4-ethyl-phenyl, 3,4-dichloro-phenyl, 4-fluoro-phenyl, 4-chloro-phenyl, 4-methylthio-phenyl, 2,3-dihydro-benzofuran-5-yl, or 1-methyl-benzotriazol-5-yl;

$L_1$ is —CH$_2$—;
D is —P-A$_2$;
P is —CH$_2$—;
A$_2$ is phenyl substituted at the para position with a substituent selected from the group consisting of methoxy, ethoxy, isopropyloxy, difluoromethoxy, hydroxy, and aminocarbonyl; or A$_2$ is pyridin-3-yl or pyridin-4-yl substituted with methoxy;
W is N;
L$_2$ is a bivalent radical selected form the group consisting of —NH—CH$_2$CH$_2$—; wherein R$^x$, R$^y$, and R$^z$ are each H;
Q is

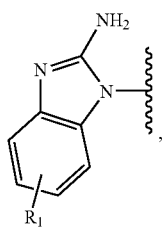
Q$_1$

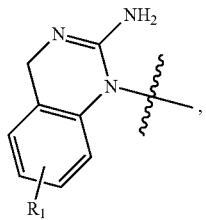
Q$_2$

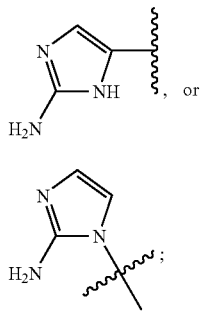
Q$_3$, or

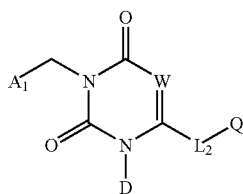
Q$_5$;

wherein R$_a$ and R$_b$ are each hydrogen;
R$_1$ is a substituent selected from hydrogen, fluoro, or chloro; and enantiomers, diastereomers, solvates, and pharmaceutically acceptable salts thereof.

A further embodiment of the present invention is directed to a pharmaceutical composition comprising of Formula (Ia) (wherein L$_1$ is CH$_2$)

Formula (Ia)

selected from the group consisting of
a compound of Formula (Ia) wherein A$_1$ is 3,4-dichloro-phenyl, D is 4-methoxy-phenylmethyl, W is N, L$_2$ is —NH(CH$_2$)$_2$—, and Q is 1H-benzoimidazol-2-ylamino;
a compound of Formula (Ia) wherein A$_1$ is 4-fluoro-phenyl, D is 4-methoxy-phenylmethyl, W is N, L$_2$ is —NH(CH$_2$)$_2$—, and Q is 2-amino-imidazol-1-yl;
a compound of Formula (Ia) wherein A$_1$ is 4-fluoro-phenyl, D is 4-methoxy-phenylmethyl, W is N, L$_2$ is —NH(CH$_2$)$_2$—, and Q is 2-amino-benzoimidazol-1-yl;
a compound of Formula (Ia) wherein A$_1$ is 4-fluoro-phenyl, D is 4-methoxy-phenylmethyl, W is N, L$_2$ is NH(CH$_2$)$_2$—, and Q is 2-amino-3H-imidazol-4-yl;
a compound of Formula (Ia) wherein A$_1$ is 4-fluoro-phenyl, D is 4-methoxy-phenylmethyl, W is N, L$_2$ is —NH(CH$_2$)$_2$—, and Q is 2-amino-5-fluoro-benzoimidazol-1-yl;
a compound of Formula (Ia) wherein A$_1$ is 4-fluoro-phenyl, D is 4-methoxy-phenylmethyl, W is N, L$_2$ is —NHCH$_2$—, and Q is 2-amino-1H-imidazol-4-yl;
a compound of Formula (Ia) wherein A$_1$ is 4-fluoro-phenyl, D is 4-methoxy-phenylmethyl, W is N, L$_2$ is —NH(CH$_2$)$_2$—, and Q is 2-amino-6-methyl-benzoimidazol-1-yl;
a compound of Formula (Ia) wherein A$_1$ is 4-fluoro-phenyl, D is 4-methoxy-phenylmethyl, W is N, L$_2$ is —NH(CH$_2$)$_2$—, and Q is 2-amino-5-trifluoromethyl-benzoimidazol-1-yl;
a compound of Formula (Ia) wherein A$_1$ is 4-fluoro-phenyl, D is 4-methoxy-phenylmethyl, W is N, L$_2$ is —NH(CH$_2$)$_2$—, and Q is 2-amino-5-methanesulfonyl-benzoimidazol-1-yl;
a compound of Formula (Ia) wherein A$_1$ is 4-fluoro-phenyl, D is 4-methoxy-phenylmethyl, W is N, L$_2$ is —NH(CH$_2$)$_2$—, and Q is 2-amino-6-chloro-benzoimidazol-1-yl;
a compound of Formula (Ia) wherein A$_1$ is 4-fluoro-phenyl, D is 4-methoxy-phenylmethyl, W is N, L$_2$ is —NH(CH$_2$)$_2$—, and Q is 2-amino-4-fluoro-benzoimidazol-1-yl;
a compound of Formula (Ia) wherein A$_1$ is 4-fluoro-phenyl, D is 4-methoxy-phenylmethyl, W is N, L$_2$ is —NH(CH$_2$)$_2$—, and Q is 2-amino-4H-quinazolin-3-yl;
a compound of Formula (Ia) wherein A$_1$ is 4-methoxy-phenyl, D is 4-methoxy-phenylmethyl, W is CH, L$_2$ is —C(O)NH(CH$_2$)$_2$—, and Q is 2-amino-benzoimidazol-1-yl;
a compound of Formula (Ia) wherein A$_1$ is 4-chloro-phenyl, D is 4-methoxy-phenylmethyl, W is N, L$_2$ is —NH(CH$_2$)$_2$—, and Q is 2-amino-benzoimidazol-1-yl;
a compound of Formula (Ia) wherein A$_1$ is 4-fluoro-phenyl, D is 4-methoxy-phenylmethyl, W is N, L$_2$ is —NH(CH$_2$)$_2$—, and Q is 2-t-butylcarbonylamino-benzoimidazol-1-yl;
a compound of Formula (Ia) wherein A$_1$ is 4-fluoro-phenyl, D is 4-methoxy-phenylmethyl, W is N, L$_2$ is —NH(CH$_2$)$_2$—, and Q is a mixture of 2-methylamino-benzoimidazol-1-yl and 2-dimethylamino-benzoimidazol-1-yl;
a compound of Formula (Ia) wherein A$_1$ is 4-fluoro-phenyl, D is 4-methoxy-phenylmethyl, W is N, L$_2$ is —NH(CH$_2$)$_2$—, and Q is 2-trifluoromethylcarbonylamino-benzoimidazol-1-yl;
a compound of Formula (Ia) wherein A$_1$ is 4-fluoro-phenyl, D is 4-methoxy-phenylmethyl, W is N, L$_2$ is —NH(CH$_2$)$_2$—, and Q is 2-t-butylcarbonylamino-imidazol-1-yl;
a compound of Formula (Ia) wherein A$_1$ is 4-fluoro-phenyl, D is 4-trifluoromethoxy-phenylmethyl, W is N, L$_2$ is —NH(CH$_2$)$_2$—, and Q is 2-amino-benzoimidazol-1-yl;
a compound of Formula (Ia) wherein A$_1$ is 4-fluoro-phenyl, D is 4-difluoromethoxy-phenylmethyl, W is N, L$_2$ is —NH(CH$_2$)$_2$—, and Q is 2-amino-benzoimidazol-1-yl;
a compound of Formula (Ia) wherein A$_1$ is 4-fluoro-phenyl, D is 4-fluoro-phenylmethyl, W is N, L$_2$ is —NH(CH$_2$)$_2$—, and Q is 2-amino-imidazol-1-yl;
a compound of Formula (Ia) wherein A$_1$ is 4-fluoro-phenyl, D is 4-trifluoromethoxy-phenylmethyl, W is N, L$_2$ is —NH(CH$_2$)$_2$—, and Q is 2-amino-imidazol-1-yl;
a compound of Formula (Ia) wherein A$_1$ is 4-fluoro-phenyl, D is 4-difluoromethoxy-phenylmethyl, W is N, L$_2$ is —NH(CH$_2$)$_2$—, and Q is 2-amino-imidazol-1-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-methylcarbonylamino-benzoimidazol-1-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-6-fluoro-benzoimidazol-1-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 5-fluoro-2-amino-benzoimidazol-1-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-5-trifluoromethyl-benzoimidazol-1-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-4,6-difluoro-benzoimidazol-1-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-6,7-difluoro-benzoimidazol-1-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-6-chloro-benzoimidazol-1-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-4-fluoro-benzoimidazol-1-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-7-fluoro-benzoimidazol-1-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-6-fluoro-benzoimidazol-1-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-5-fluoro-benzoimidazol-1-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, 2-amino-5-trifluoromethyl-benzoimidazol-1-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-4,6-difluoro-benzoimidazol-1-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-6,7-difluoro-benzoimidazol-1-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-6-chloro-benzoimidazol-1-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-4-fluoro-benzoimidazol-1-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-7-fluoro-benzoimidazol-1-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-4H-quinazolin-3-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-5-chloro-4H-quinazolin-3-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-6-chloro-4H-quinazolin-3-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-7-chloro-4H-quinazolin-3-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-6-fluoro-4H-quinazolin-3-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-7-fluoro-4H-quinazolin-3-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-4H-quinazolin-3-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-5-chloro-4H-quinazolin-3-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-6-chloro-4H-quinazolin-3-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-7-chloro-4H-quinazolin-3-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-6-fluoro-4H-quinazolin-3-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-7-fluoro-4H-quinazolin-3-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-3H-imidazol-4-yl;

a compound of Formula (Ia) wherein $A_1$ is 4-fluoro-phenyl, D is 4-trifluoromethoxy-phenylmethyl, W is N, $L_2$ is —NH($CH_2$)$_2$—, and Q is 2-amino-3H-imidazol-4-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-4-methoxy-benzoimidazol-1-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-6-hydroxy-4H-quinazolin-3-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-7-methoxy-4H-quinazolin-3-yl;

a compound of Formula (Ia) wherein $A_1$ is 4-fluoro-phenyl, D is 4-difluoromethoxy-phenylmethyl, W is N, $L_2$ is —NH($CH_2$)$_2$—, and Q is 2-amino-4H-quinazolin-1-yl;

a compound of Formula (Ia) wherein $A_1$ is 3,4-dichloro-phenyl, D is 4-methoxy-phenylmethyl, W is N, $L_2$ is —NH($CH_2$)$_2$—, and Q is 2-amino-3H-imidazol-4-yl;

a compound of Formula (Ia) wherein $A_1$ is 4-ethyl-phenyl, D is 4-methoxy-phenylmethyl, W is N, $L_2$ is —NH($CH_2$)$_2$—, and Q is 2-amino-3H-imidazol-4-yl;

a compound of Formula (Ia) wherein $A_1$ is 4-methylthio-phenyl, D is 4-methoxy-phenylmethyl, W is N, $L_2$ is —NH($CH_2$)$_2$—, and Q is 2-amino-3H-imidazol-4-yl;

a compound of Formula (Ia) wherein $A_1$ is 2,3-dihydro-benzofuran-5-yl, D is 4-methoxy-phenylmethyl, W is N, $L_2$ is —NH($CH_2$)$_2$—, and Q is 2-amino-3H-imidazol-4-yl;

a compound of Formula (Ia) wherein $A_1$ is 3,4-dichloro-phenyl, D is 2,3-dihydro-benzofuran-5-ylmethyl, W is N, $L_2$ is —NH($CH_2$)$_2$—, and Q is 2-amino-3H-imidazol-4-yl;

a compound of Formula (Ia) wherein $A_1$ is 4-methylthio-phenyl, D is 2,3-dihydro-benzofuran-5-ylmethyl, W is N, $L_2$ is —NH(CH$_2$)$_2$—, and Q is 2-amino-3H-imidazol-4-yl;

a compound of Formula (Ia) wherein $A_1$ is 4-ethyl-phenyl, D is 2,3-dihydro-benzofuran-5-ylmethyl, W is N, $L_2$ is —NH(CH$_2$)$_2$—, and Q is 2-amino-3H-imidazol-4-yl;

a compound of Formula (Ia) wherein $A_1$ is 2,3-dihydro-benzofuran-5-yl, D is 2,3-dihydro-benzofuran-5-ylmethyl, W is N, $L_2$ is —NH(CH$_2$)$_2$—, and Q is 2-amino-3H-imidazol-4-yl;

a compound of Formula (Ia) wherein $A_1$ is 1-methyl-1H-benzotriazol-5-yl, D is 4-methoxy-phenylmethyl, W is N, $L_2$ is —NH(CH$_2$)$_2$—, and Q is 2-amino-3H-imidazol-4-yl;

a compound of Formula (Ia) wherein $A_1$ is 1-methyl-1H-benzotriazol-5-yl, D is 2,3-dihydro-benzofuran-5-ylmethyl, W is N, $L_2$ is —NH(CH$_2$)$_2$—, and Q is 2-amino-3H-imidazol-4-yl;

a compound of Formula (Ia) wherein $A_1$ is 3,4-dichloro-phenyl, D is 4-methoxy-phenylmethyl, W is N, $L_2$ is —NH(CH$_2$)$_2$—, and Q is 2-amino-benzoimidazol-1-yl;

a compound of Formula (Ia) wherein $A_1$ is 4-methylthio-phenyl, D is 4-methoxy-phenylmethyl, W is N, $L_2$ is —NH(CH$_2$)$_2$—, and Q is 2-amino-benzimidazol-1-yl;

a compound of Formula (Ia) wherein $A_1$ is 4-ethyl-phenyl, D is 4-methoxy-phenylmethyl, W is N, $L_2$ is —NH(CH$_2$)$_2$—, and Q is 2-amino-benzoimidazol-1-yl;

a compound of Formula (Ia) wherein $A_1$ is 2,3-dihydro-benzofuran-5-yl, D is 4-methoxy-phenylmethyl, W is N, $L_2$ is —NH(CH$_2$)$_2$—, and Q is 2-amino-benzoimidazol-1-yl;

a compound of Formula (Ia) wherein $A_1$ is 3,4-dichloro-phenyl, D is 2,3-dihydro-benzofuran-5-ylmethyl, W is N, $L_2$ is —NH(CH$_2$)$_2$—, and Q is 2-amino-benzoimidazol-1-yl;

a compound of Formula (Ia) wherein $A_1$ is 4-methylthio-phenyl, D is 2,3-dihydro-benzofuran-5-ylmethyl, W is N, $L_2$ is —NH(CH$_2$)$_2$—, and Q is 2-amino-benzoimidazol-1-yl;

a compound of Formula (Ia) wherein $A_1$ is 4-ethyl-phenyl, D is 2,3-dihydro-benzofuran-5-ylmethyl, W is N, $L_2$ is —NH(CH$_2$)$_2$—, and Q is 2-amino-benzoimidazol-1-yl;

a compound of Formula (Ia) wherein $A_1$ is 2,3-dihydro-benzofuran-5-yl, D is 2,3-dihydro-benzofuran-5-ylmethyl, W is N, $L_2$ is —NH(CH$_2$)$_2$—, and Q is 2-amino-benzoimidazol-1-yl;

a compound of Formula (Ia) wherein $A_1$ is 1-methyl-1H-benzotriazol-5-yl, D is 4-methoxy-phenylmethyl, W is N, $L_2$ is —NH(CH$_2$)$_2$—, and Q is 2-amino-benzoimidazol-1-yl;

a compound of Formula (Ia) wherein $A_1$ is 1-methyl-1H-benzotriazol-5-yl, D is 2,3-dihydro-benzofuran-5-ylmethyl, W is N, $L_2$ is —NH(CH$_2$)$_2$—, and Q is 2-amino-benzoimidazol-1-yl;

a compound of Formula (Ia) wherein $A_1$ is 3,4-dichloro-phenyl, D is 4-difluoromethoxy-phenylmethyl, W is N, $L_2$ is —NH(CH$_2$)$_2$—, and Q is 2-amino-3H-imidazol-4-yl;

a compound of Formula (Ia) wherein $A_1$ is 4-methylthio-phenyl, D is 4-difluoromethoxy-phenylmethyl, W is N, $L_2$ is —NH(CH$_2$)$_2$—, and Q is 2-amino-3H-imidazol-4-yl;

a compound of Formula (Ia) wherein $A_1$ is 4-ethyl-phenyl, D is 4-difluoromethoxy-phenylmethyl, W is N, $L_2$ is —NH(CH$_2$)$_2$—, and Q is 2-amino-3H-imidazol-4-yl;

a compound of Formula (Ia) wherein $A_1$ is 2,3-dihydro-benzofuran-5-yl, D is 4-difluoromethoxy-phenylmethyl, W is N, $L_2$ is —NH(CH$_2$)$_2$—, and Q is 2-amino-3H-imidazol-4-yl;

a compound of Formula (Ia) wherein $A_1$ is 1-methyl-1H-benzotriazol-5-yl, D is 4-difluoromethoxy-phenylmethyl, W is N, $L_2$ is —NH(CH$_2$)$_2$—, and Q is 2-amino-3H-imidazol-4-yl;

a compound of Formula (Ia) wherein $A_1$ is 3,4-dichloro-phenyl, D is 4-difluoromethoxy-phenylmethyl, W is N, $L_2$ is —NH(CH$_2$)$_2$—, and Q is 2-amino-benzoimidazol-1-yl;

a compound of Formula (Ia) wherein $A_1$ is 4-methylthio-phenyl, D is 4-difluoromethoxy-phenylmethyl, W is N, $L_2$ is —NH(CH$_2$)$_2$—, and Q is 2-amino-benzoimidazol-1-yl;

a compound of Formula (Ia) wherein $A_1$ is 4-ethyl-phenyl, D is 4-difluoromethoxy-phenylmethyl, W is N, $L_2$ is —NH(CH$_2$)$_2$—, and Q is 2-amino-benzoimidazol-1-yl;

and a compound of Formula (Ia) wherein $A_1$ is 2,3-dihydro-benzofuran-5-yl, D is 4-difluoromethoxy-phenylmethyl, W is N, $L_2$ is —NH(CH$_2$)$_2$—, and Q is 2-amino-benzoimidazol-1-yl and enantiomers, diastereomers, solvates, and pharmaceutically acceptable salts thereof.

Additional embodiments of the present invention include those compounds wherein the substituents selected from one or more of the variables defined herein (i.e. $A_1$, $L_1$, s, X, P, $A_2$, W, $L_2$, and Q) are independently selected to be any individual substituent or any subset of substituents selected from the complete list as defined herein.

The compounds of the present invention may also be present in the form of pharmaceutically acceptable salts. For use in medicine, the salts of the compounds of this invention refer to non-toxic "pharmaceutically acceptable salts" (Ref. International J. Pharm., 1986, 33, 201-217; J. Pharm. Sci., 1977 (January), 66, 1, 1). Other salts well known to those in the art may, however, be useful in the preparation of compounds according to this invention or of their pharmaceutically acceptable salts. Representative organic or inorganic acids include, but are not limited to, hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexane-sulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are intended to be encompassed within the scope of this invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

Even though the compounds of the present invention (including their pharmaceutically acceptable salts and pharmaceutically acceptable solvates) can be administered alone, they will generally be administered in admixture with a pharmaceutical carrier, excipient, or diluent selected with regard to the intended route of administration and standard pharmaceutical or veterinary practice. Thus, the present invention is directed to pharmaceutical and veterinary compositions comprising compounds of Formula (I) and one or more pharmaceutically acceptable carriers, excipients or diluents.

By way of example, in the pharmaceutical and veterinary compositions of the present invention, the compounds of the present invention may be admixed with any suitable binder(s), lubricant(s), suspending agent(s), coating agent(s), and/or solubilising agent(s).

Tablets or capsules of the compounds may be administered singly or two or more at a time, as appropriate. It is also possible to administer the compounds in sustained release formulations.

Alternatively, the compounds of the general Formula (I) can be administered by inhalation or in the form of a suppository or pessary, or they may be applied topically in the form of a lotion, solution, cream, ointment or dusting powder. An alternative means of transdermal administration is by use of a skin patch. For example, they can be incorporated into a cream consisting of an aqueous emulsion of polyethylene glycols or liquid paraffin. They can also be incorporated, at a concentration of between 1 and 10% by weight, into an ointment consisting of a white wax or white soft paraffin base together with such stabilisers and preservatives as may be required.

For some applications, preferably the compositions are administered orally in the form of tablets containing excipients such as starch or lactose, or in capsules or ovules either alone or in admixture with excipients, or in the form of elixirs, solutions or suspensions containing flavouring or coloring agents.

The compositions (as well as the compounds alone) can also be injected parenterally, for example intracavernosally, intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

By way of further example, pharmaceutical and veterinary compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate the major site of absorption. For parenteral administration, the carrier will usually consist of sterile water and other ingredients may be added to increase solubility or preservation. Injectable suspensions or solutions may also be prepared utilizing aqueous carriers along with appropriate additives.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those skilled in that art. To be administered in the form of a transdermal delivery system, the dosage administration will, of course, be continuous rather than intermittent throughout the dosage regimen.

The instant pharmaceutical composition will generally contain a per dosage unit (e.g., tablet, capsule, powder, injection, teaspoonful and the like) from about 0.001 to about 50 mg/kg. In one embodiment, the instant pharmaceutical composition contains a per dosage unit of from about 0.01 to about 20 mg/kg of compound, and preferably from about 0.05 to about 10 mg/kg. Methods are known in the art for determining therapeutically effective doses for the instant pharmaceutical composition. The therapeutically effective amount for administering the pharmaceutical composition to a human, for example, can be determined mathematically from the results of animal studies.

A therapeutically effective amount for use of the instant compounds or a pharmaceutical composition thereof comprises a dose range from about 0.1 mg to about 3000 mg, in particular from about 1 mg to about 1000 mg or, more particularly from about 10 mg to about 500 mg of active ingredient in a regimen of about 1 to 4 times per day for an average (70 kg) human; although, it is apparent to one skilled in the art that the therapeutically effective amount for active compounds of the invention will vary as will the conditions being treated.

For oral administration, a pharmaceutical composition is preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated.

It is also apparent to one skilled in the art that the therapeutically effective dose for active compounds of the invention or a pharmaceutical composition thereof will vary according to the desired effect. Therefore, optimal dosages to be administered may be readily determined and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

Compounds of this invention may be administered in any of the foregoing compositions and dosage regimens or by means of those compositions and dosage regimens established in the art whenever use of the compounds of the invention as prokineticin receptor antagonists is required for a subject in need thereof.

The invention also provides a pharmaceutical or veterinary pack or kit comprising one or more containers filled with one or more of the ingredients of the pharmaceutical and veterinary compositions of the invention.

As antagonists of a Prokineticin 1 receptor, the compounds of Formula (I) are useful in methods for treating or preventing a disease or condition in a mammal which disease or condition is affected by the antagonistic activity of one or more Prokineticin 1 receptors. Such methods comprise administering to a mammal in need of such treatment or prevention a therapeutically effective amount of a compound, salt or solvate of Formula (I). The compounds of Formula (I) are useful in methods for preventing or treating gastrointestinal (GI) diseases, cancers of the GI tract and reproductive organs, and pain. Examples of GI diseases to be within the scope of the present invention include, but are not limited to: irritable bowel syndrome (IBS, including diarrhea-predominant, as well as alternating diarrhea/constipation forms of IBS), inflammatory bowel disease (IBD, including ulcerative colitis, and Crohn's disease), and GERD and secretory bowel disorders induced by pathogens. Examples of cancers within the scope of the present invention include, but are not limited to, testicular cancer, ovarian cancer, Leydig cell carcinoma, and cancers of the small or large bowel. An example of pain to be covered within the scope of the present invention, is, but not restricted to, visceral hyperalgesia often associated with IBS and IBD.

While the present invention comprises compositions comprising one or more of the compounds of Formula (I) the present invention also comprises compositions comprising intermediates used in the manufacture of compounds of Formula (I).

Representative IUPAC names for the compounds of the present invention were derived using the ACD/LABS SOFTWARE™ Index Name Pro Version 4.5 nomenclature software program provided by Advanced Chemistry Development, Inc., Toronto, Ontario, Canada.

Abbreviations used in the instant specification, particularly the Schemes and Examples, are as follows:

| | |
|---|---|
| Boc = | tert-butoxycarbonyl |
| BuLi = | n-butyllithium |
| Cpd or Cmpd = | compound |
| d = | day/days |
| DCM = | dichloromethane |
| DIAD = | diisopropyl azodicarboxylate |
| DIPEA or DIEA = | diisopropylethylamine |
| DMEM = | Dulbecco's Modified Eagle Medium |
| DMF = | N,N-dimethylformamide |
| DMSO = | dimethylsulfoxide |
| EtOAc = | ethyl acetate |
| EtOH = | ethanol |
| h = | hour/hours |
| LDA = | lithium diisopropylamide |
| M = | molar |
| MeCN = | acetonitrile |
| MeOH = | methanol |
| min = | minute(s) |
| NaOMe = | sodium methoxide |
| rt/RT = | room temperature |
| THF = | tetrahydrofuran |
| TFA = | trifluoroacetic acid |

General Schemes

Representative compounds of the present invention can be synthesized in accordance with the general synthetic methods described below and are illustrated in the schemes that follows. The starting materials and reagents used in the schemes that follow are understood to be either commercially available or prepared by methods known to those skilled in the art. Since the schemes are an illustration, the invention should not be construed as being limited by the chemical reactions and conditions expressed.

Scheme A illustrates the general synthesis of certain intermediates of the present invention wherein W is N and $L_2$ is other than —C(=O)NH(CR$^y$R$^z$)$_{2-5}$—.

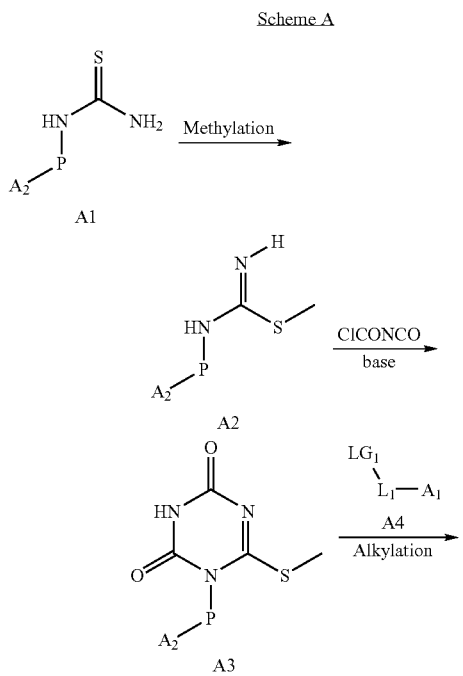

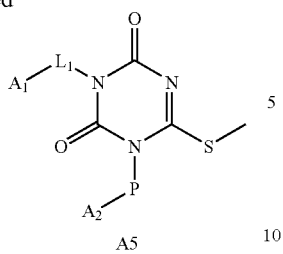

A compound of formula A1 may be methylated with a methylating agent such as methyl iodide in a polar solvent such as methanol to give a compound of formula A2. A compound of formula A2 may be condensed with an appropriately substituted isocyanate such as N-chlorocarbonyl isocyanate in the presence of excess tertiary amine such as diisopropylethylamine to give a triazine of formula A3. A compound of formula A3 may be alkylated with a compound of formula A4, wherein $LG_1$ is a leaving group, using conventional chemistry known to one versed in the art. For instance, when $LG_1$ is a hydroxy group, compound A4 may be coupled with compound A3 with the aid of a coupling agent such as DIAD in the presence of triphenylphosphine in a non-alcoholic polar solvent such as THF or methylene chloride. Alternatively, $LG_1$ may be a halide, tosylate, or the like such that $LG_1$ is displaced by the amino portion of a compound of A3 to give a compound of formula A5.

Scheme B describes the synthesis of certain -$L_2$-Q intermediates of the present invention wherein W is N, $L_2$ is —NH—CH($R^x$)—($CR^yR^z$)$_{1-5}$—, and Q is of formula $Q_3$.

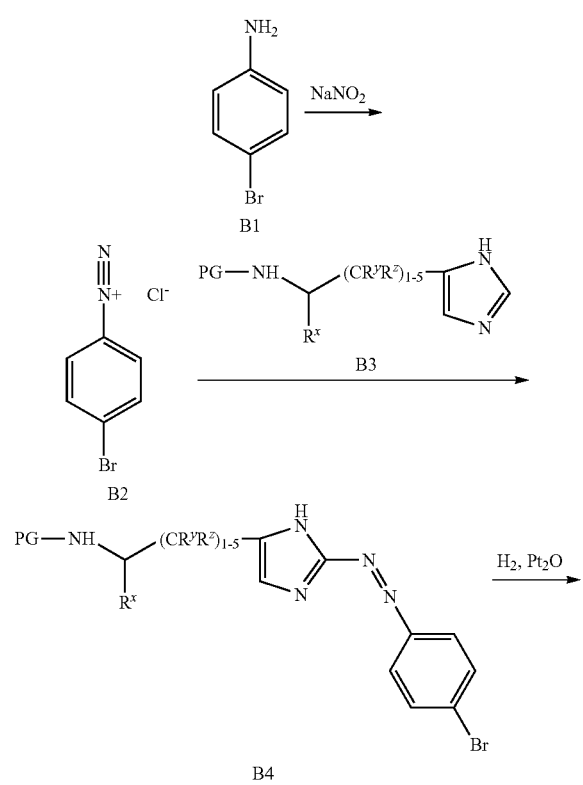

The commercially available compound of formula B1 may be treated with sodium nitrite to form a diazonium salt of formula B2. Reaction of a compound of formula B3 (wherein PG is a conventional amino protecting group) with a compound of formula B2 affords the diazo-compound of formula B4. Hydrogenation of a compound of formula B4 in the presence of a transition metal catalyst such as platinum (I) oxide affords an amino-substituted imidazole of formula B5. Subsequent removal of the amino protecting group (PG) provides a compound of formula B6, which may be used as a nucleophile in reaction with a compound of formula A5 to provide a compound of Formula (I)-B.

Scheme C describes the synthesis of certain compounds of the present invention wherein W is N, $L_2$ is other than —C(=O)NH($CR^yR^z$)$_{2-5}$— and Q is of formula $Q_2$ wherein $R_a$ is H.

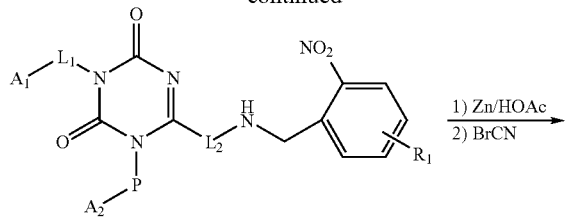

C4

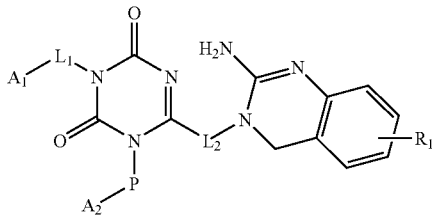

Formula (I)-C

A compound of formula A5 may be treated with a diamine of formula C1 to give a compound of formula C2. One versed in the art will recognize that when $L_2$ is asymmetrical, a nitrogen-protecting group may be necessary to avoid competing reactions between the amino groups. The terminal amine of a compound of formula C2 may be alkylated with an aldehyde of formula C3 in the presence of a hydride source, such as sodium triacetoxyborohydride, to give a compound of formula C4. Reaction with zinc metal in the presence of acetic acid, followed by treatment with cyanogen bromide affords compounds of Formula (I)-C.

Scheme D illustrates the synthesis of certain compounds of the present invention wherein W is N, $L_2$ is other than —C(=O)NH(CR$^y$R$^z$)$_{2-5}$— and Q is of formula $Q_1$ wherein $R_a$ is H.

Scheme D

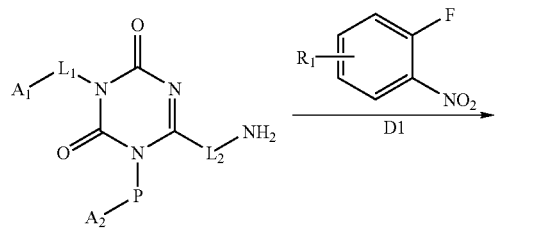

C2

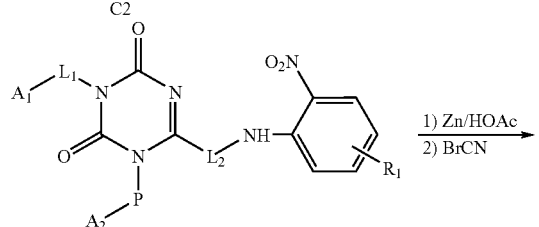

D2

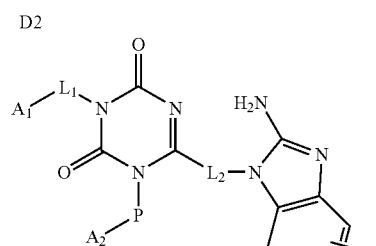

Formula (I)-D

A compound of formula C2 may undergo an aromatic nucleophilic displacement with a compound of formula D1 to give a compound of formula D2. Reaction of with zinc metal in the presence of acetic acid, followed by treatment with cyanogens bromide affords a $Q_1$-substituted compound of Formula (I)-D.

Scheme E illustrates the synthesis of certain compounds of the present invention wherein W is N, $L_2$ is other than —C(=O)NH(CR$^y$R$^z$)$_{2-5}$— and Q is of formula $Q_5$.

Scheme E

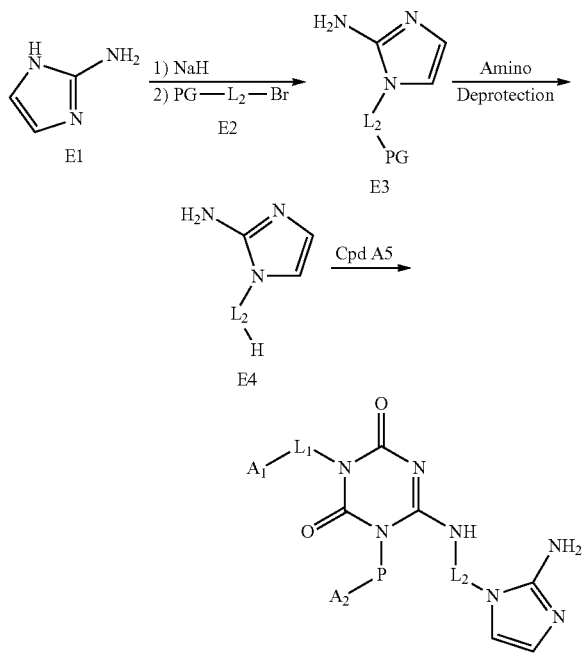

Formula (I)-E

A compound of formula E1 may be treated with a base and then alkylated with a compound of formula E2 to provide a compound of formula E3. The compound of formula E3 may be used in an nucleophilic displacement reaction with a compound of formula A5 to provide compounds of formula (I)-E of the present invention.

Scheme F illustrates the general synthesis of compounds of the present invention wherein W is C(R$_w$), and $L_2$ is other than —C(=O)NH(CR$^y$R$^z$)$_{2-5}$—.

Scheme F

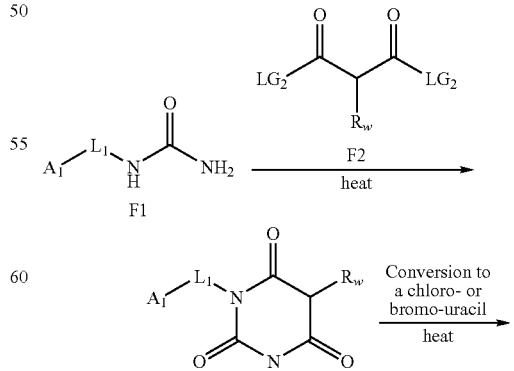

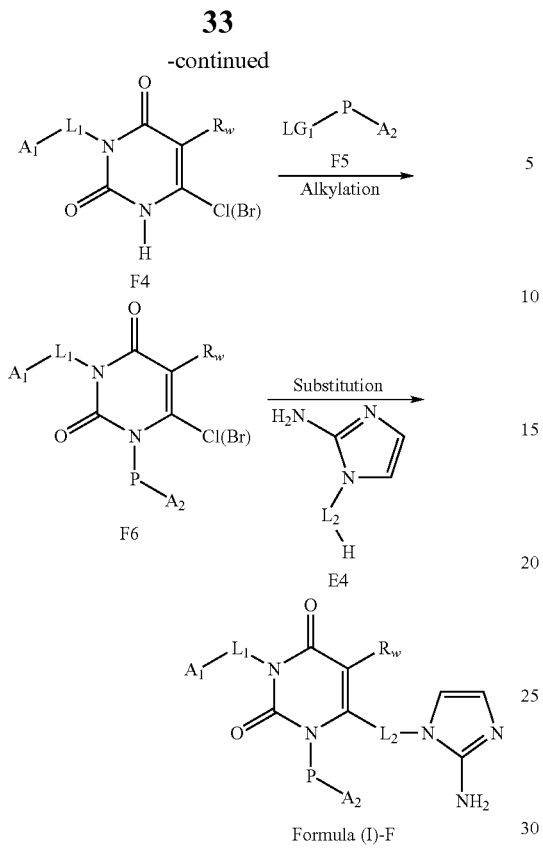

A compound of formula F1 may be condensed with a compound of formula F2 with heating, (wherein LG$_2$ is C$_{1-4}$alkoxy, choro, or the like) to form a compound of formula F3. A compound of formula F3 may then be treated with phosphorus oxychloride, phosphorus pentachloride, or the like and heat to afford a compound of formula F4. Alternatively, the bromo analog may be used in this synthetic sequence, which is prepared from F3 using phosphorus oxybromide in place of phosphorus oxychloride. A compound of formula F5 may be used to install —P-A$_2$ via conventional alkylation procedures. A compound of formula F6 may be elaborated via a nucleophilic displacement of the chloride or bromide with an amino compound of formula B6, C1, E4, or the like to afford a compound of Formula (I)-F. For illustrative purposes only, Scheme F shows a compound of formula E4 as the nucleophile in reaction with a compound of formula F6.

Scheme G illustrates the general synthesis of compounds of the present invention in which W is N and L$_2$ is —C(=O)NH(CR$^y$R$^z$)$_{2-5}$—.

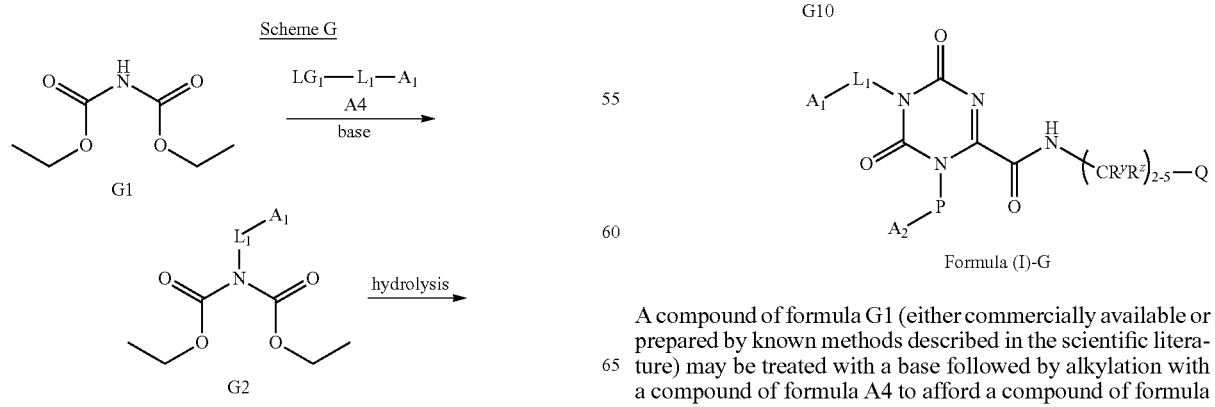

A compound of formula G1 (either commercially available or prepared by known methods described in the scientific literature) may be treated with a base followed by alkylation with a compound of formula A4 to afford a compound of formula G2. Treatment of a compound of formula G2 with an aqueous base such as sodium hydroxide gives a compound of formula G3, which upon treatment with ammonia or its equivalent provides a compound of formula G4. The compound of formula G4 may then be condensed with a compound of formula G5 to form a triazine compound of formula G6. A compound of Formula G6 may be treated with a methylating agent such as trimethylsilyl diazomethane to give a methyl ester of formula G7. Under Mitsunobu-type coupling conditions (in the presence of a coupling agent, activating agent), an alcohol of formula G8 may be coupled with a secondary amine of formula G7 to afford a compound of formula G9. Standard base hydrolysis of the methyl ester gives the corresponding carboxylic acid of formula G10, which may be coupled with an amine of formula G11 (which includes a Q-substituent or a precursor to a Q-substituent) to afford a compound of Formula (I)-G.

Scheme H illustrates the general synthesis of compounds of the present invention wherein W is CH and $L_2$ is —C(=O)NH$(CR^yR^z)_{2-5}$—.

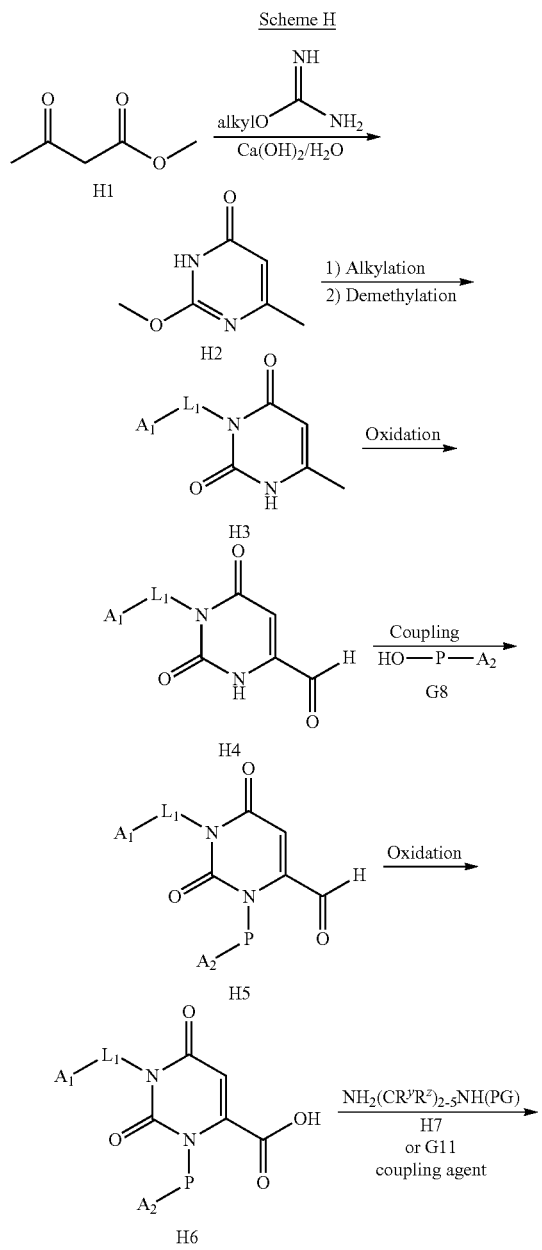

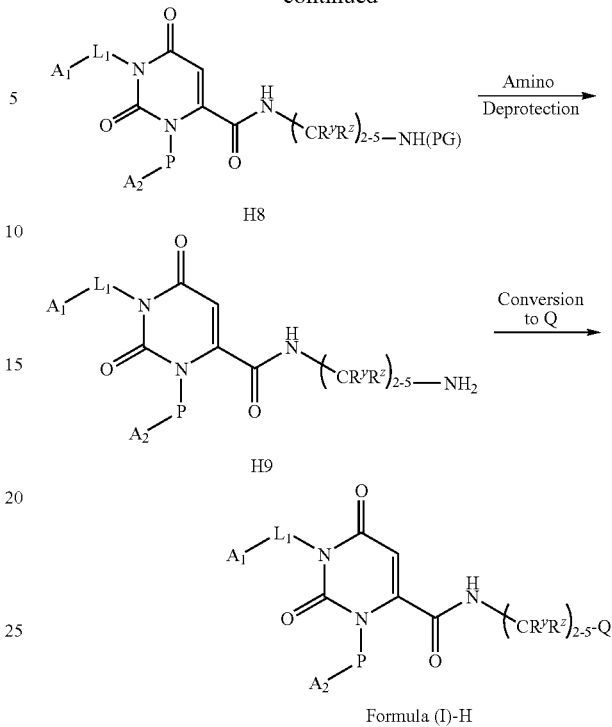

A compound of formula H1 may be condensed with an O-alkylated isourea to afford a cyclic compound of formula H2. The amine may be deprotonated with an organometallic base and subsequently treated with a compound of formula A4 to install the -L$_1$A$_1$ substituent of Formula (I). O-demethylation of an alkylated compound of H2 affords a compound of formula H3. Using conventional oxidation chemistry, the methyl substituent of H3 may be converted to its corresponding aldehyde, affording a compound of formula H4. A compound of formula H4 may be treated under Mitsunobu-type coupling conditions (in the presence of a coupling agent and activating agent), with an alcohol of formula G8 to afford a compound of formula H5. Oxidation of the aldehyde group using an appropriate oxidizing agent gives a compound of formula H6, wherein the corresponding carboxylic acid may be coupled with an amine of formula H7 (PG is an appropriate amino protecting group) to afford a compound of formula H8. The conventional removal of the amino protecting group, PG, yields the primary amine of formula H9, which may be converted to a Q-group according to the methods described herein to yield a compound of Formula (I)-H. Similarly, a compound of formula H6 may be coupled with a Q-containing amine of formula G11 to give a compound of Formula (I)-H.

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The instant compounds may also be used as intermediates in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Reagents were purchased from commercial sources. Nuclear magnetic resonance (NMR) spectra for hydrogen atoms were measured in the indicated solvent with (TMS) as the internal standard on a Bruker-Biospin Inc. DRX 500 (500 MHz) or DPX 300 (300 MHz) spectrometer. The values are expressed in parts per million downfield from TMS. The mass spectra (MS) were determined on a Micromass Platform LC spectrometer, an Agilent LC spectrometer or a Micromass LCT spectrometer using electrospray techniques. Microwave accelerated reactions were performed using a CEM Discover microwave instrument, and were contained in a sealed pressure vessel unless otherwise noted. Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Example 1

3-(4-Fluoro-benzyl)-6-methylsulfanyl-1-(4-trifluoromethoxy-benzyl)-1H-[1,3,5]triazine-2,4-dione (Cpd 1f)

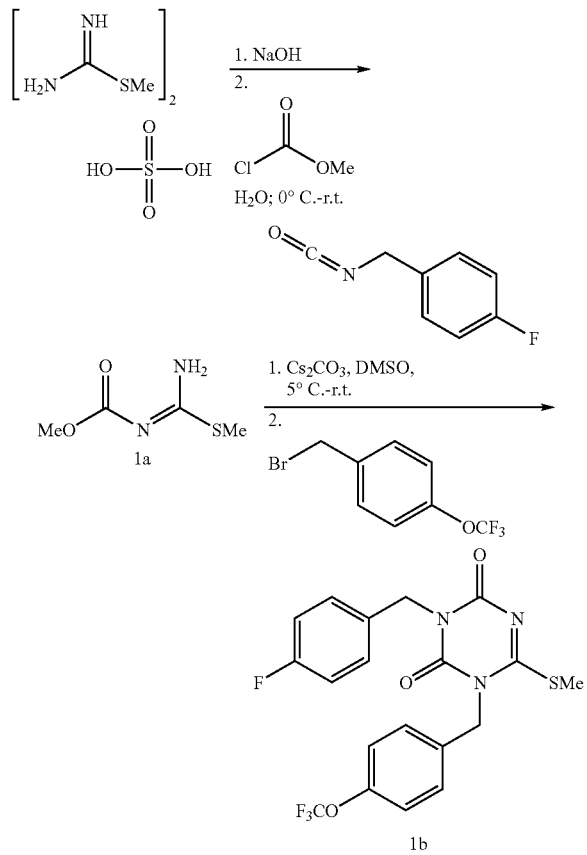

A. N-Methylcarbonyl-S-methylisothiourea (Cpd 1a). A stirred suspension of S-methylisothiourea sulfate (46 g, 0.17 mol) in water (60 mL.) was heated to 60° C. and then cooled quickly to 0° C. using an ice-salt bath. The aqueous mixture was treated over 1 h with cold aqueous NaOH (60 mL containing 13.2 g; 0.33 mol) while the internal temperature was maintained at 5° C. The thick pale green slurry obtained was stirred 30 min at 5° C., cooled to 0° C., and treated with cold methyl chloroformate (15.6 g, 0.17 mol) over 1 h while maintaining the reaction temperature at 0-5° C. Stirring was continued for another 15 min at 0-5° C. then the ice-salt bath was removed and the mixture warmed to rt. The mixture was then transferred to a separatory funnel and extracted with ethyl acetate (2×60 mL). The aqueous layer was transferred to the reaction flask, cooled to 0-5° C., treated with cold aqueous NaOH (40 mL containing 19.8 g; 0.17 mol), and the resulting mixture was stirred at 5° C. for 30 min. After cooling to 0° C., the mixture was treated with methyl chloroformate (7.8 g, 0.08 mol) over 1 hr while maintaining the temperature at 0-5° C. After stirring for an additional 15 min, the mixture was extracted with ethyl acetate (2×30 mL) and the extract was combined with the previous one. The combined extracts were washed once with cold brine (15 mL) and dried over $Na_2SO_4$. The solvent was removed under reduced pressure and the resulting residue was purified by a flash column on silica gel (10%-60% EtOAc in heptane) to afford compound 1a as a white powder. $^1$H-NMR (CDCl$_3$) δ 2.47 (s, 3H), 3.75 (s, 3H) and 7.28-8.35 (bs, 2H).

B. 3-(4-Fluoro-benzyl)-6-methylsulfanyl-1-(4-trifluoromethoxy-benzyl)-1H-[1,3,5]triazine-2,4-dione (Cpd 1b). 4-Fluorobenzyl isocyanate (2.1 mL, 16.2 mmol) was added dropwise over 3 min to a 5° C. solution of 1a (2 g, 13.5 mmol) and $Cs_2CO_3$ (14.1 g, 43.2 mmol) in DMSO (20 mL). The cooling bath was removed and the reaction was stirred toward rt. At 50 min, LC/MS analysis showed approximately 10% of compound 1a remaining. An additional portion of 4-fluorobenzyl isocyanate (0.21 mL, 1.6 mmol) was added and after stirring for 20 min the reaction was judged complete by LC/MS analysis. To the stirred rt mixture was added 4-trifluoromethoxybenzyl bromide (5.2 mL, 32.5 mmol). After stirring for 1 h, water (20 mL) was added, and the resulting solution was loaded on a 100 mL SLE cartridge. Elution with DCM (500 mL) was followed by concentration under vacuum to a DMSO-containing residue. The residue was stored for 24 h at <0.5 mm Hg to remove most of the DMSO, then purified on a silica gel flash column (20% EtOAc-75% EtOAc in heptane), to give compound 1b as a white powder.

Example 2

6-[2-(2-Amino-3H-imidazol-4-yl)-ethylamino]-3-(4-fluoro-benzyl)-1-(4-trifluoromethoxy-benzyl)-1H-[1,3,5]triazine-2,4-dione (Cpd 54)

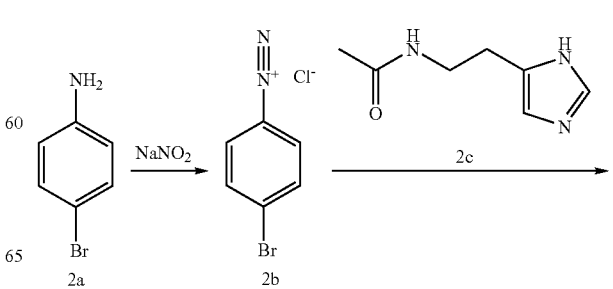

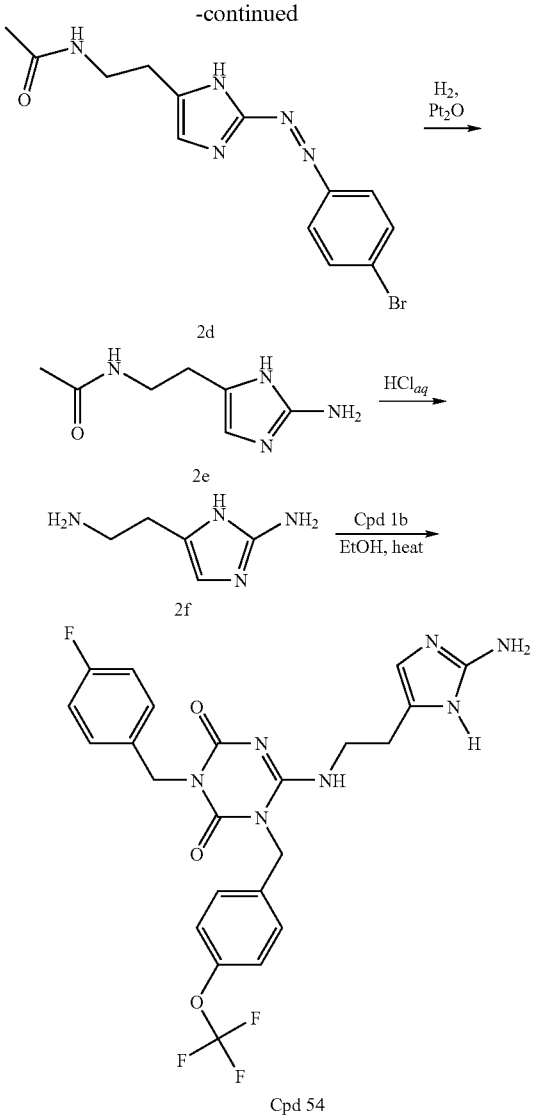

(Parr shaker). A hydrogen pressure of >45 psi was maintained throughout the reduction process. After the reaction mixture had been shaken for 23 h, the catalyst was removed by filtration over Celite and the resulting solution was concentrated. The residual mixture of compound 2e and p-bromoaniline was used in the subsequent step without further purification.

C. 5-(2-Amino-ethyl)-1H-imidazol-2-ylamine (Cpd 2f). A solution of compound 2e (0.5 g) in 10 ml of 6 N hydrochloric acid was heated at 100° C. for 16 hr. The solvent was removed in vacuo and the resulting residue was stored at <1 mm Hg for 24 h. The resulting mixture of 2f and p-bromoaniline were used without further purification.

D. 6-[2-(2-Amino-3H-imidazol-4-yl)-ethylamino]-3-(4-fluoro-benzyl)-1-(4-trifluoromethoxy-benzyl)-1H-[1,3,5] triazine-2,4-dione (Cpd 54). To a solution of compound 2f (0.050 g, 0.12 mmol) in ethanol (0.75 mL) was added compound 1b (72 mg, 0.36 mmol) and DIEA (0.084 mL, 0.48 mmol). The mixture was heated at 95° C. for 17 h, concentrated, and the resulting residue was purified by reverse-phase liquid chromatography using a gradient of 90:10 (water:acetonitrile, with 0.1% TFA) to 90:10 (water:acetonitrile, with 0.1% TFA) to give the title compound 54. HRMS calcd. for $C_{23}H_{22}F_4N_7O_3$ m/z 520.1720 (M+H). found: 520.1744.

Other compounds of the present invention may be prepared by those skilled in the art by varying the starting materials, reagent(s) and conditions used. Using the general procedure of Example 2, the following compounds were prepared:

| Cpd | MS obs | MS calc | Cpd | MS obs (ES+) | MS calc |
|---|---|---|---|---|---|
| 6 | 452.13 | 451.18 | 65 | 488.19 | 487.23 |
| 53 | 502.00 | 501.17 | 66 | 502.21 | 501.21 |
| 59 | 516.16 | 515.12 | 67 | 503.17 | 502.22 |
| 60 | 476.22 | 475.23 | 68 | 515.19 | 514.22 |
| 61 | 494.14 | 493.19 | 79 | 552.02 | 551.11 |
| 62 | 490.19 | 489.21 | 80 | 530.10 | 529.17 |
| 63 | 528.14 | 527.12 | 81 | 512.14 | 511.21 |
| 64 | 506.14 | 505.19 | 82 | 526.14 | 525.19 |
|  |  |  | 83 | 539.15 | 538.20 |

A. N-{2-[2-(4-Bromo-phenylazo)-3H-imidazol-4-yl]-ethyl}-acetamide (Cpd 2d). A solution of sodium nitrite (2.3 g, 0.033 mol) in 32 mL of water was cooled to 0° C. and was added gradually to a stirred, ice-cold solution of compound 1a (5.4 g, 0.031 mol) in 160 mL of 2.3 N hydrochloric acid. The solution of diazonium salt (2b) was stored at approximately 0° C. for 40 min and was then added gradually to a stirred, ice-cold solution of 5.0 g (0.032 mol) of compound 2c in 320 mL of 0.2 M sodium carbonate. The mixture was stirred at ice temperature for 2 h before adjusting the pH to about 10 with 3N NaOH$_{(aq)}$. The resulting yellow-orange precipitate was collected and dried. A solution of the crude product in the minimum volume of 20% methanol/chloroform was applied to a column of flash grade silica gel which had been previously equilibrated with 50% EtOAc/hexanes. The column was eluted with a gradient, increasing to 20% methanol/EtOAc. The crude mixture was purified to give compound 2d of sufficient purity for use in the subsequent step.

B. N-[2-(2-Amino-3H-imidazol-4-yl)-ethyl]-acetamide (Cpd 2e). To a nitrogen-degassed/blanketed suspension of compound 2d (3.2 g, 0.0096 mol) in 130 mL of absolute ethanol was added platinum oxide (0.32 g, 0.0014 mol). The resulting slurry was subjected to catalytic hydrogenation at ambient temperature at an initial hydrogen pressure of 55 psi Example 3

6-[2-(2-Amino-4H-quinazolin-3-yl)-ethylamino]-3-(4-fluoro-benzyl)-1-(4-methoxy-benzyl)-1H-[1,3,5] triazine-2,4-dione (Cpd 12)

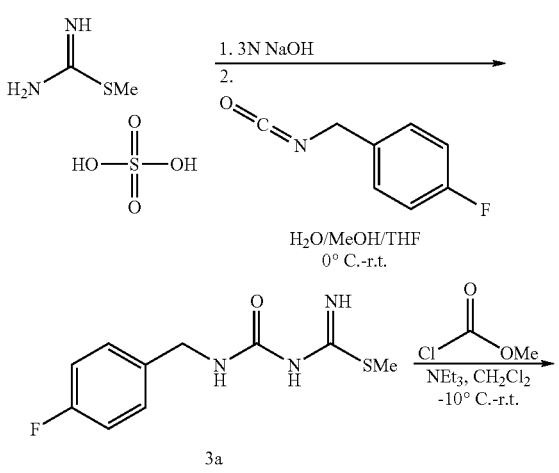

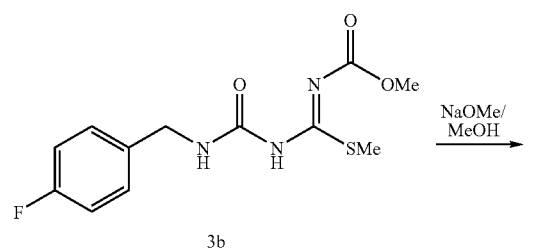
3b

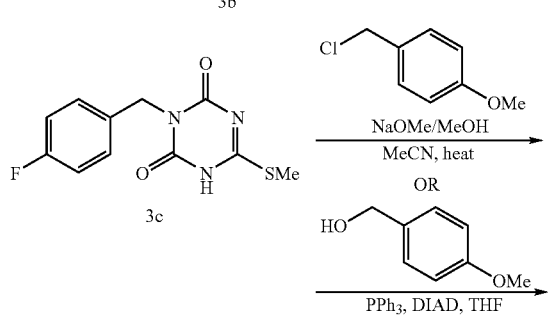
3c

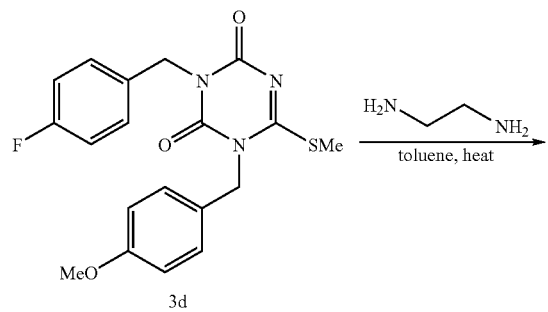
3d

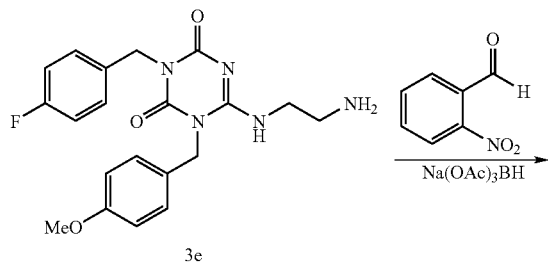
3e

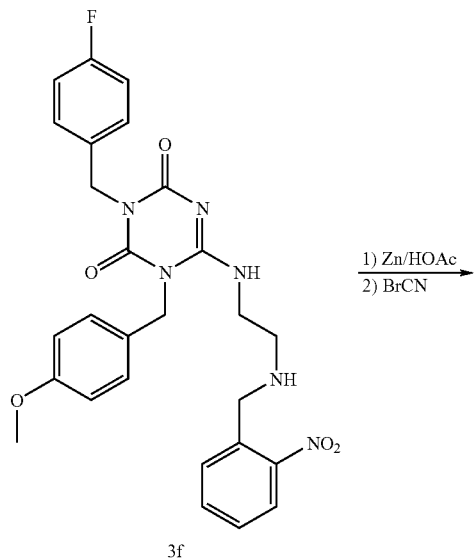
3f

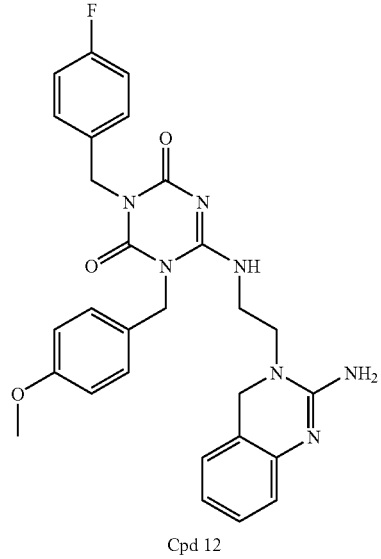
Cpd 12

A. ((4-Fluorobenzyl)amino)carbonyl)carbamimidothioic acid methyl ester (Cpd 3a). S-methylisothiouronium sulfate (10.0 g, 35.9 mmol) was dissolved in 8:2:1 MeOH/H$_2$O/THF and the mixture was treated with 3 N NaOH (12 mL, 35.9 mmol). The solution was then cooled to 0° C. and 4-fluorobenzyl isocyanate (5.43 g, 35.9 mmol) was added dropwise over 30 min. The reaction was stirred overnight and gradually warmed to room temperature. The mixture was then washed with saturated aqueous NH$_4$Cl and extracted with dichloromethane. The combined organic phases were dried over Na$_2$SO$_4$, filtered and concentrated under reduced pressure. The resultant residue was purified on an Isco flash column (20% EtOAc-100% EtOAc in heptanes), to give compound 3a (4.1 g) as a white powder.

B. 5-(Methylthio)-3,7-dioxo-1-(4-fluorobenzyl)-2-oxa-4,6,8-triazanon-4-en-9-oic acid methyl ester (Cpd 3b). A solution of compound 3a (4.1 g, 17.0 mmol) in dichloromethane was treated with triethylamine (3.08 mL, 22.1 mmol) and the mixture was cooled to −10° C. Methyl chloroformate (2.62 mL, 34.0 mmol) was added dropwise via an addition funnel over 15 min and the reaction was allowed to stir for 4 h while gradually warming to room temperature. The solution was then washed with saturated aqueous NH$_4$Cl and extracted with dichloromethane. The combined organic phases were dried over Na$_2$SO$_4$, filtered and concentrated. The resultant residue was purified on an Isco flash column (5% MeOH) to afford compound 3b (3.63 g) as a white solid.

C. 3-(4-Fluoro-benzyl)-6-methylsulfanyl-1H-[1,3,5]triazine-2,4-dione (Cpd 3c). Compound 3b (3.63 g, 12.1 mmol) was dissolved in MeOH (100 mL) and the solution was treated with NaOMe in MeOH (4.6 M, 2.90 mL, 13.3 mmol) and the reaction was allowed to stir at room temperature for 1 h. A white precipitate formed upon addition of the NaOMe. The reaction mixture was diluted with 1N HCl (50 mL) and the resultant precipitate was collected by filtration. The solid was dried under reduced pressure at 160° C. over xylenes to afford compound 3c (3.6 g) as its HCl salt.

D. 3-(4-Fluoro-benzyl)-1-(4-methoxy-benzyl)-6-methylsulfanyl-1H-[1,3,5]triazine-2,4-dione (Cpd 3d). Compound 3c (500 mg, 1.65 mmol) was dissolved in THF and was treated with 4-methoxybenzyl alcohol (227 mg, 1.65 mmol), triphenylphosphine (866 mg, 3.30 mmol), and diisopropyl azodicarboxylate (334 mg, 1.65 mmol). The reaction was allowed to stir overnight at room temperature. After monitoring the reaction via HPLC, the solution was partitioned between water and ethyl acetate. The combined organic layers were dried over anhydrous sodium sulfate, filtered and reduced. The crude mixture was purified via Isco flash column (20% ethyl acetate—100% ethyl acetate in heptane, 40 min) to afford compound 3d as a white solid. $^1$H NMR (DMSO, d$_6$). δ 3.29 (s, 3H), 3.74 (s, 3H), 4.93 (s, 2H), 5.03 (s, 2H), 6.89-6.92 (d, 2H, J=8.62), 7.12-7.36 (m, 4H), 7.38-7.41 (m, 2H).

E. 4-[3-(3,4-Dichloro-benzyl)-6-methylsulfanyl-2,4-dioxo-3,4-dihydro-2H-[1,3,5]triazin-1-ylmethyl]-benzamide (Alternative route to Cpd 3d). Compound 3c (dichlorobenzyl) (200 mg, 0.56 mmol) was dissolved in MeCN and was treated with diisopropylethylamine (0.196 mL, 1.13 mmol) and 4-chloromethyl benzyl chloride (96 mg, 0.56 mmol). The reaction mixture was heated to 80° C. and was allowed to stir overnight. The reaction mixture was washed with saturated aqueous NH$_4$Cl and extracted with ethyl acetate. The combined organic extracts were dried over Na$_2$SO$_4$, filtered and concentrated. The resultant crude mixture was purified by Isco flash column (20%-100% EtOAc in heptanes, 40 min) to afford compound 3d as a white powder.

F. 6-(2-Amino-ethylamino)-3-(4-fluoro-benzyl)-1-(4-methoxy-benzyl)-1H-[1,3,5]triazine-2,4-dione (Cpd 3e). A solution of compound 3d (390 mg, 1.01 mmol) in toluene (8 mL) and was treated with ethylenediamine (302 mg, 5.03 mmol). The reaction was heated to 90° C. and was allowed to stir overnight. The mixture was then partitioned between water and ethyl acetate. The combined organic layers were dried over Na$_2$SO$_4$, filtered and reduced to provide compound 3e as a crude mixture. The crude compound was used in subsequent steps without additional purification.

G. 3-(4-Fluoro-benzyl)-1-(4-methoxy-benzyl)-6-[2-(2-nitro-benzylamino)-ethylamino]-1H-[1,3,5]triazine-2,4-dione (Cpd 3f). To a flask containing compound 3e (0.050 g, 0.13 mmol) in DCE (0.5 mL) was added 2-nitrobenzaldehyde (0.022 g, 0.14 mmol). After stirring at room temperature for 30 min, Na(OAc)$_3$BH (0.055 g, 0.26 mmol) was added, and the reaction mixture was stirred at room temperature for 18 h. The reaction mixture was quenched with MeOH (0.1 mL)/isopropyl alcohol (0.5 mL), concentrated to a residue, and stored at <1 mm Hg for 15 minutes. The resulting residue containing compound 3f and approximately 30% of a dialkylated by-product was used in the following step without further purification. HRMS calcd. for C$_{27}$H$_{28}$FN$_6$O$_5$ m/z 535.2105 (M+H). found: 535.2123.

H. 6-[2-(2-Amino-4H-quinazolin-3-yl)-ethylamino]-3-(4-fluoro-benzyl)-1-(4-methoxy-benzyl)-1H-[1,3,5]triazine-2,4-dione (Cpd ??). To the above residue of compound 3f was added isopropyl alcohol (0.5 mL), acetic acid (0.1 mL, 1.7 mmol), and Zn (0.051 g, 0.78 mmol). The reaction slurry was heated with stirring at 50° C. for 20 min. After cooling to rt, the reaction mixture was quenched with 50% aqueous NaOH (0.05 mL), stirred for 5 minutes, and loaded on a 1 g silica SPE cartridge. After 5 min the organic products were eluted with a solution of 94% CH$_2$Cl$_2$/5% MeOH/1% Et$_3$N, (13 mL). The resulting solution was concentrated and stored at <1 mm Hg for 18 h. The resulting residue was used in the following step without further purification. HRMS calcd. for C$_{27}$H$_{30}$FN$_6$O$_3$ m/z 505.2363 (M+H). found: 505.2374.

The above residue was dissolved in EtOH (0.5 mL), CH$_2$Cl$_2$ (0.1 mL), and cyanogen bromide (0.065 mL, 0.195 mmol, 3M in CH$_2$Cl$_2$) was added. The resulting solution was stirred for 6.5 h at room temperature. The reaction mixture was quenched with 50% NaOH (0.05 mL), stirred for 5 minutes, and loaded on a 1 g silica SPE cartridge. After 5 minutes the organics were eluted with a solution of 94% CH$_2$Cl$_2$/5% MeOH/1% Et$_3$N, (13 mL). The resulting solution was concentrated and stored at <1 mm Hg for 18 h. The resulting residue was purified by preparative reverse phase HPLC to yield the title compound 12. $^1$H NMR (CDCl$_3$) δ 3.45-3.82 (4H, m), 3.68 (3H, s), 4.41 (2H, s), 4.88 (2H, s), 5.05 (2H, s), 6.71-6.52 (12H, m), 7.62 (1H, bs), 8.39 (2H, bs). HRMS calcd. for C$_{28}$H$_{29}$FN$_7$O$_3$ m/z 530.2316 (M+H). found: 530.2316.

Other compounds of the present invention may be prepared by those skilled in the art by varying the starting materials, reagent(s) and conditions used. Using the general procedure of Example 3, the following compounds were prepared:

| Cpd | MS obs (ES+) | MS calc |
|---|---|---|
| 41 | 566.23 | 565.20 |
| 42 | 600.14 | 599.17 |
| 43 | 600.17 | 599.17 |
| 44 | 600.18 | 599.17 |
| 45 | 584.23 | 583.20 |
| 46 | 584.20 | 583.20 |
| 48 | 618.16 | 617.16 |
| 49 | 618.22 | 617.16 |
| 50 | 618.22 | 617.16 |
| 51 | 602.19 | 601.19 |
| 52 | 602.19 | 601.19 |
| 56 | 582.21 | 581.20 |
| 57 | 596.22 | 595.22 |
| 58 | 566.23 | 565.20 |

Example 4

6-[2-(2-Amino-6-methyl-benzoimidazol-1-yl)-ethylamino]-3-(4-fluoro-benzyl)-1-(4-methoxy-benzyl)-1H-[1,3,5]triazine-2,4-dione (Cpd 3)

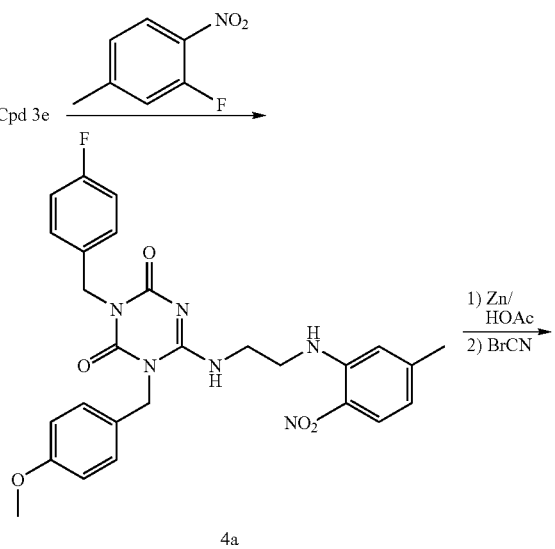

4a

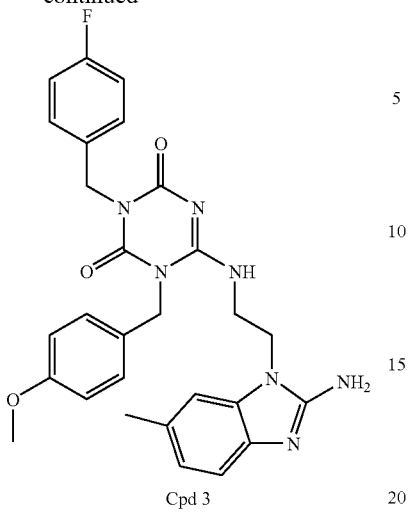

Cpd 3

A. 3-(4-Fluoro-benzyl)-1-(4-methoxy-benzyl)-6-[2-(5-methyl-2-nitro-phenylamino)-ethylamino]-1H-[1,3,5]triazine-2,4-dione (Cpd 4a). To a flask containing compound 3e (0.025 g, 0.063 mmol) in DMF (0.3 mL) was added 2-fluoro-4-methyl-nitrobenzene (0.011 g, 0.069 mmol). The reaction was sealed and the mixture heated to 60° C. with stirring for 17 h. The mixture was cooled to rt and used in the following step without further purification. HRMS calcd. for $C_{27}H_{28}FN_6O_5$ m/z 535.2105 (M+H). found: 535.2117.

B. 6-[2-(2-Amino-6-methyl-benzoimidazol-1-yl)-ethylamino]-3-(4-fluoro-benzyl)-1-(4-methoxy-benzyl)-1H-[1,3,5]triazine-2,4-dione (Cpd 3) To a solution of crude compound 4a was added isopropyl alcohol (0.3 mL), acetic acid (0.050 mL, 0.85 mmol), and Zn (0.026 g, 0.39 mmol). The reaction slurry was heated with stirring at 65° C. for 30 min. After cooling to rt, the reaction mixture was quenched with 50% NaOH (0.05 mL), stirred for 5 minutes, and loaded on a 1 g silica SPE cartridge. After 5 min the organics were eluted with a solution of 94% $CH_2Cl_2$/5% MeOH/1% $Et_3N$, (13 mL). The resulting solution was concentrated and stored at <1 mm Hg for 18 h. The resulting residue was used in the following step without further purification. HRMS calcd. for $C_{27}H_{30}FN_6O_3$ m/z 505.2363 (M+H). found: 505.2360.

The above residue was dissolved in EtOH (0.5 mL) and cyanogen bromide (0.035 mL, 0.095 mmol, 3M in $CH_2Cl_2$) was added. The resulting solution was stirred for 6.5 h at room temperature. The reaction mixture was quenched with 50% NaOH (0.05 mL), stirred for 5 min, and loaded on a 1 g silica SPE cartridge. After 5 minutes the organics were eluted with a solution of 94% $CH_2Cl_2$/5% MeOH/1% $Et_3N$, (13 mL). The resulting solution was concentrated and stored at <1 mm Hg for 18 h. The resulting residue was purified by preparative reverse phase HPLC to yield the title compound 3. $^1$H NMR (CDCl$_3$) δ 2.32 (3H, s), 3.63 (3H, s), 3.67-3.81 (2H, m), 4.13-4.28 (2H, m), 4.87 (2H, s), 5.00 (2H, s), 6.70 (2H, J=8.59 Hz, d), 6.86-7.01 (4H, m), 7.05-7.16 (3H, m), 7.33 (2H, dd, J=8.72 and 3.16 Hz), 7.71 (1H, bs), 8.73 (2H, bs). HRMS calcd. for $C_{28}H_{29}FN_7O_3$ m/z 530.2316 (M+H). found: 530.2316.

Other compounds of the present invention may be prepared by those skilled in the art by varying the starting materials, reagent(s) and conditions used. Using the general procedure of Example 4, the following compounds were prepared:

| Cpd | MS obs (ES+) | MS calc |
|---|---|---|
| 5 | 534.05 | 533.20 |
| 7 | 530.19 | 529.22 |
| 8 | 584.03 | 583.20 |
| 9 | 594.16 | 593.19 |
| 10 | 550.14 | 549.17 |
| 11 | 534.17 | 533.20 |
| 14 | 532.20 | 531.18 |
| 15 | 599.30 | 599.27 |
| 17 |  | 611.19 |
| 20 | 552.16 | 551.19 |
| 24 |  | 593.20 |
| 25 | 570.12 | 569.18 |
| 26 | 570.13 | 569.18 |
| 27 | 620.15 | 619.18 |
| 28 | 588.16 | 587.17 |
| 29 | 588.13 | 587.17 |
| 30 | 586.14 | 585.15 |
| 31 | 570.14 | 569.18 |
| 32 | 570.14 | 569.18 |
| 33 | 588.13 | 587.17 |
| 34 | 588.13 | 587.17 |
| 35 | 638.12 | 637.17 |
| 36 | 606.11 | 605.16 |
| 37 | 606.11 | 605.16 |
| 38 | 604.14 | 603.14 |
| 39 | 588.12 | 587.17 |
| 40 | 588.12 | 587.17 |
| 55 | 582.21 | 581.20 |
| 69 | 566.15 | 565.14 |
| 70 | 544.14 | 543.21 |
| 71 | 526.20 | 525.25 |
| 72 | 540.23 | 539.23 |
| 73 | 578.11 | 577.14 |
| 74 | 556.16 | 555.21 |
| 75 | 538.19 | 537.25 |
| 76 | 552.20 | 551.23 |
| 77 | 553.23 | 552.23 |
| 78 | 565.25 | 564.23 |
| 84 | 601.89 | 601.12 |
| 85 | 579.96 | 579.19 |
| 86 | 562.00 | 561.23 |
| 87 | 576.01 | 575.21 |

Example 5

6-[2-(2-Amino-imidazol-1-yl)-ethylamino]-3-(4-fluoro-benzyl)-1-(4-methoxy-benzyl)-1H-[1,3,5]triazine-2,4-dione (Cpd 2)

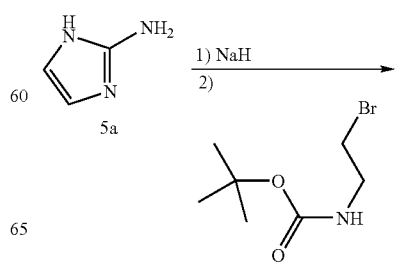

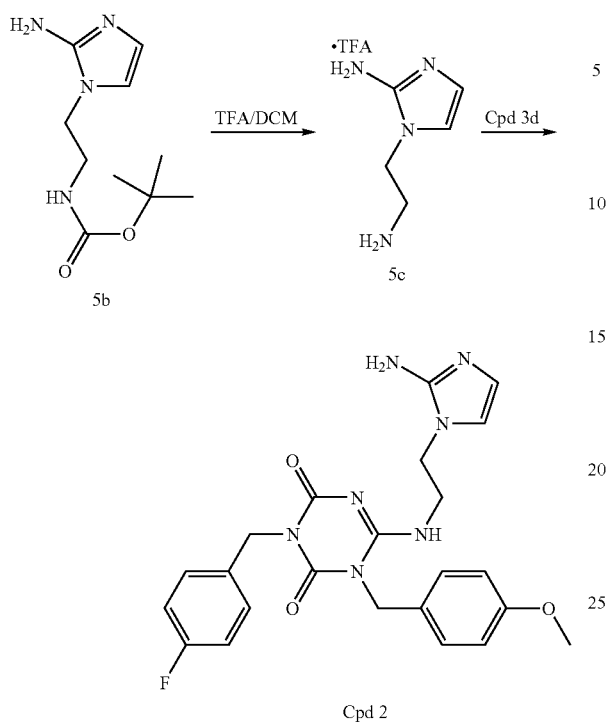

Cpd 2

6.96 (2H, at, J=8.74 Hz), 7.15 (2H, d, J=8.18 Hz), 7.37 (1H, d, J=7.37 Hz), 7.39 (1H, d, J=8.23 Hz), 7.81 (2H, bs), 12.67 (1H, bs). HRMS calcd. for $C_{23}H_{25}FN_7O_3$ m/z 466.2003 (M+H). found: 466.2008.

Other compounds of the present invention may be prepared by those skilled in the art by varying the starting materials, reagent(s) and conditions used. Using the general procedure of Example 5, the following compounds were prepared:

| Cpd | MS obs (ES+) | MS calc |
|---|---|---|
| 2 | 466.19 | 465.19 |
| 18 | 549.6 | 549.25 |
| 19 | 570.19 | 569.18 |
| 21 | 454.09 | 453.17 |
| 22 | 520.04 | 519.16 |
| 23 | 502.15 | 501.17 |

Example 6

6-[2-(1H-Benzoimidazol-2-ylamino)-ethylamino]-3-(3,4-dichloro-benzyl)-1-(4-methoxy-benzyl)-1H-[1,3,5]triazine-2,4-dione (Cpd 1)

A. [2-(2-Amino-imidazol-1-yl)-ethyl]-carbamic acid tert-butyl ester (Cpd 5b). To a flask containing 2-aminoimidazole sulfate 5a (1 g, 3.8 mmol) in DMF (20 mL) was added sodium hydride (0.65 g, 16.3 mmol) in small portions with stirring. The temperature was maintained below 30° C. during the addition by means of an ice bath. After stirring for 30 minutes at 25-30° C., the solution was cooled to 0° C. and (2-bromoethyl)-carbamic acid tert-butyl ester (1.7 g, 7.6 mmol) in DMF (1 mL) was added. After stirring for 1 min the cooling bath was removed and the solution was stirred toward rt for 16 h. The reaction was carefully quenched with water (10 mL), extracted with EtOAc (4×10 mL), dried over sodium sulfate, filtered, and concentrated to a residue. The residue was stored at <0.5 mm Hg for 24 h to remove residual DMF, then purified by normal phase chromatography to give compound 5b (0.29 g) as a brown glass. HRMS calcd. for $C_{10}H_{19}N_4O_2$ m/z 227.1508 (M+H). found: 227.1518.

B. 1-(2-Amino-ethyl)-1H-imidazol-2-ylamine xTFA (Cpd 5c). To a flask containing 5b (0.059 g, 0.26 mmol) in DCM (2 mL) at rt was added TFA (2 mL). The resulting solution was stirred at rt for 1 h then concentrated to a residue, stored at <0.5 mm Hg for 1 h, and used directly without further purification.

C. 6-[2-(2-Amino-3H-imidazol-4-yl)-ethylamino]-3-(4-fluoro-benzyl)-1-(4-trifluoromethoxy-benzyl)-1H-[1,3,5]triazine-2,4-dione (Cpd 2). To a solution of compound 3d (0.050 g, 0.13 mmol) in ethanol (0.75 mL) was added crude 5c (0.26 mmol) and DIEA (0.068 mL, 0.39 mmol). The mixture was heated at 95° C. for 17 h, concentrated, and the resulting residue was purified by reverse-phase liquid chromatography using a gradient of 90:10 (water:acetonitrile, with 0.1% TFA) to 90:10 (water:acetonitrile, with 0.1% TFA) to give the title compound 2. $^1$H NMR (CDCl$_3$) δ, 3.60-3.71 (2H, m), 3.74 (3H, s), 3.88-3.97 (2H, m), 4.97 (2H, s), 5.07 (2H, s), 6.03 (1H, s), 6.31 (1H, s), 6.79 (2H, d, J=8.77 Hz),

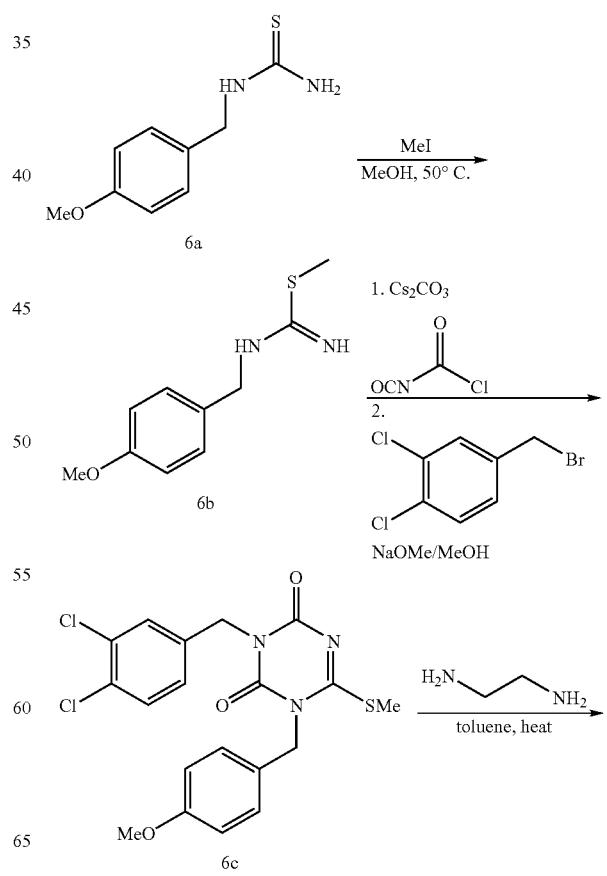

-continued

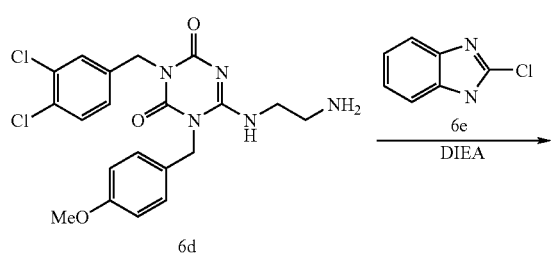

6d

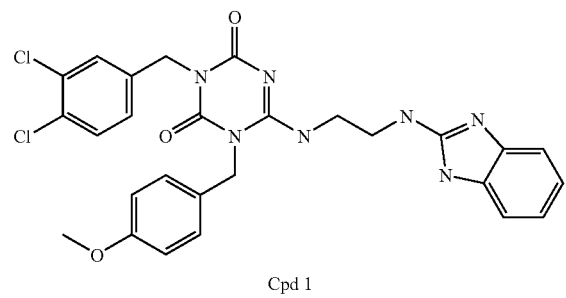

Cpd 1

A. To compound 6a (5 g, 25.5 mmol) suspended in methanol (50 mL) was added methyl iodide (4.8 mL, 0.076 mmol) and the reaction was heated to 50° C. for 15 min. The reaction was concentrated to a residue to give compound 6b. Compound 6b was used without further purification for the next reaction.

B. To compound 6b (25.5 mmol) dissolved in dry THF (50 mL) was added cesium carbonate (25 g, 76 mmol) and the reaction was cooled to −78° C. A solution of chlorocarbonyl-isocyanate (2.2 mL) in 10 mL THF was added to compound 6b and the reaction was stirred toward rt for 3 h at which time phenyl isocyanatoformate (2 mL) was added. Stirring was continued for 2 h. The residue was taken up in DMSO (50 mL) and 3,4-dichlorobenzyl bromide (7.3 g, 31 mmol) was added to the reaction. After 30 min of stirring, water (50 mL) was added to the reaction mixture and the aqueous phase was extracted with 4×50 mL ethyl ether. The combined ether extracts were dried, filtered, and concentrated under reduced pressure. The resulting residue was purified by normal phase column chromatography (10-75% EtOAc in heptane) to elute compound 6c.

C. To compound 6c (0.5 g, 1.1 mmol) in toluene (4 mL) in a microwave vessel was added ethylene diamine (382 □L, 5.7 mL) and the mixture was heated at 160° C. for 10 min. At that time, xylenes were added (10 mL) and the mixture was concentrated and stored under reduced pressure for approximately 16 h. Compound 6d was used in subsequent reactions without further purification.

D. To compound 6d (0.050 g, 0.11 mmol) in ethanol in a microwave vessel was added compound 6e (0.017 mg, 0.11 mmol) and Et₃N (25 □L, 0.14 mmol) and the mixture was heated at 180° C. for 25 min. At that time, the mixture was concentrated, and the resulting residue was purified by reverse-phase liquid chromatography using a gradient of 90:10 (water:acetonitrile, with 0.1% TFA) to 90:10 (water:acetonitrile, with 0.1% TFA) to give the title compound 1. $C_{27}H_{26}Cl_2N_7O_3$ calc=566.15; found=566.16.

Example 7

Cpd 16: A mixture of 3-(4-Fluoro-benzyl)-1-(4-methoxy-benzyl)-6-[2-(2-methylamino-benzoimidazol-1-yl)-ethylamino]-1H-[1,3,5]triazine-2,4-dione and 6-[2-(2-Dimethylamino-benzoimidazol-1-yl)-ethylamino]-3-(4-fluoro-benzyl)-1-(4-methoxy-benzyl)-1H-[1,3,5]triazine-2,4-dione

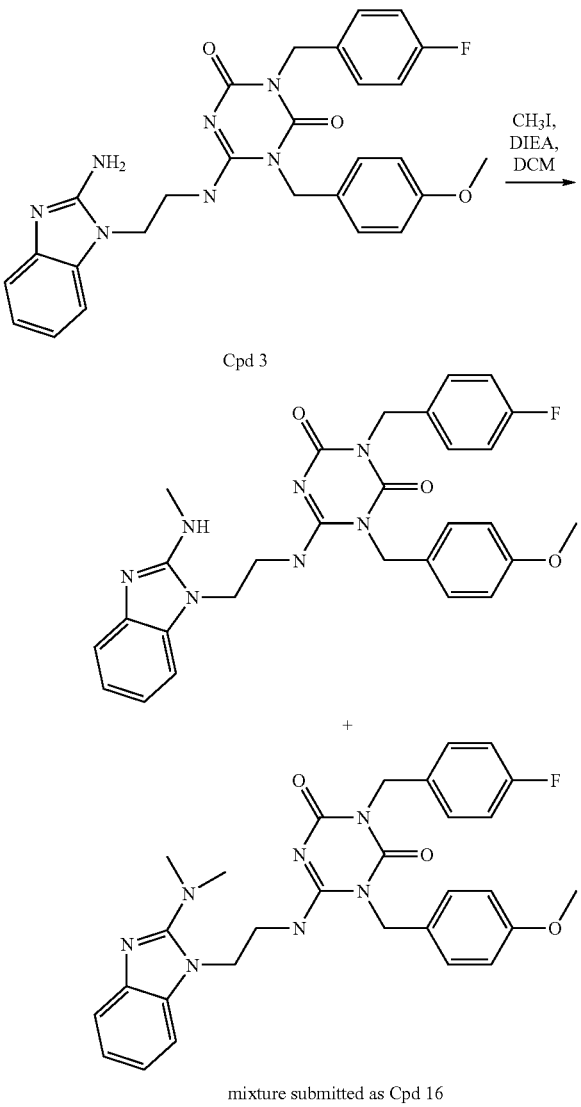

mixture submitted as Cpd 16

To the tri-hydrochloride salt of compound 3 (0.028 g, 0.045 mmol) in DCM (5 mL) was added methyl iodide (3.1 □L, 0.05 mmol) and DIEA (30 □L, 0.27 mmol), and the reaction was allowed to stir at rt. After 4 h, an additional 10 □L of DIEA was added, and stirring at rt was continued. After approximately 12 h, an additional 3.1 □L of methyl iodide and 10 □L of DIEA was added. After 4 more hours, an additional 3.1 □L of methyl iodide was added. After approximately 12 h, an additional 3.1 □L of methyl iodide and 10 □L of DIEA was added. Finally, 10 □L of methyl iodide and 20 □L of DIEA was added to completion of the reaction. Over 6 d, a total of 42.4 □L of methyl iodide and 95 □L of DIEA was added. The reaction was concentrated and purified by reverse-phase liquid chromatography to afford 60% of the mono-methylated product and 40% of the dimethylated product as a mixture.

Example 8

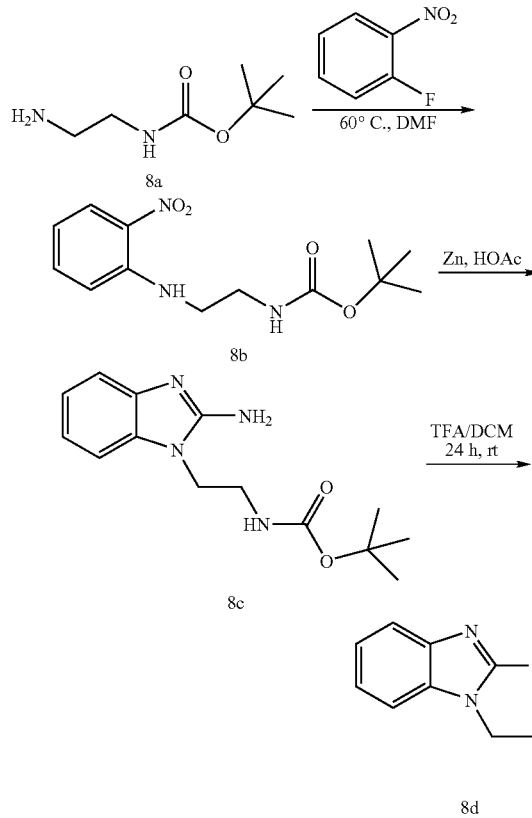

A. Compound 8c was prepared according to the methods described in Example 4, Steps A and B, substituting compound 8a for compound 3e, and substituting 2-fluoro-nitrobenzene for 2-fluoro-4-methyl-nitrobenzene in Step A. In Step B, compound 8b was substituted for compound 4a.

B. To compound 8c was added a 1:1 mixture of TFA and methylene chloride, and the mixture was stirred at rt for 24 hrs. At this time, the mixture was washed sequentially with water and saturated aqueous sodium bicarbonate, and the organic phase was concentrated to a residue of compound 8d, which was used in subsequent steps without further purification.

Example 9

1,3-Bis-(4-methoxy-benzyl)-2,6-dioxo-1,2,3,6-tetrahydro-pyrimidine-4-carboxylic acid [2-(2-aminobenzoimidazol-1-yl)-ethyl]-amide (Cpd 13)

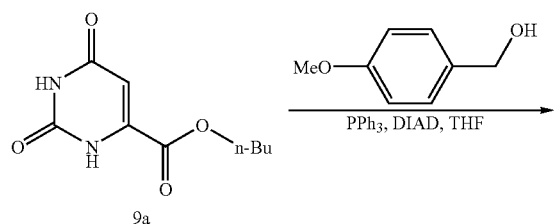

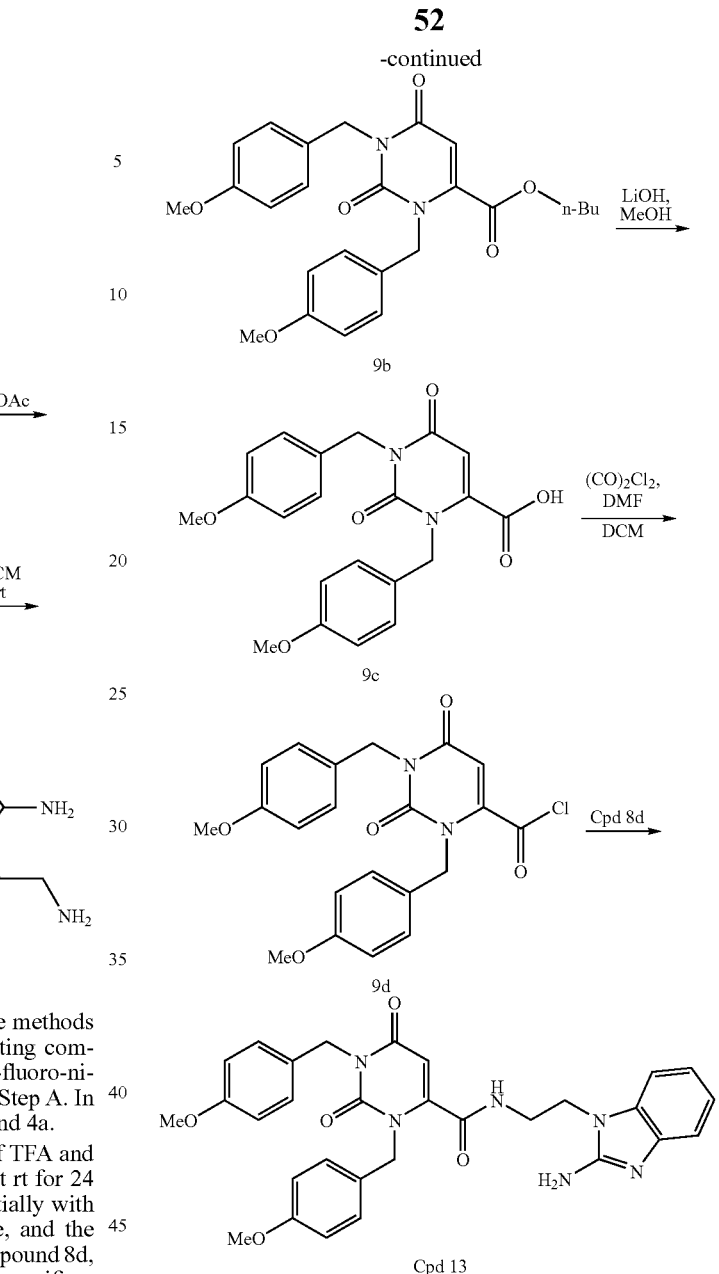

A. To compound 9a (1.00 g, 4.7 mmol) in THF (50 mL) was added triphenyl phosphine (5.0 g) and 4-methoxybenzyl alcohol (2.00 g, 14.1 mmol) at rt. To the mixture was added DIAD (3.80 g) in one portion and the reaction was stirred overnight at rt. The mixture was then diluted with water, extracted with EtOAc, dried, filtered, and concentrated to a residue under reduced pressure. The residue was purified by normal phase chromatography (heptane: EtOAc, 9:1 to 3:1) to give compound 9b.

B. Compound 9b was taken up in MeOH/H$_2$O (60 mL, 5:1) and lithium hydroxide monohydrate (0.5 g) was added to the mixture. The reaction was stirred for 48 h at rt. The mixture was then concentrated and purified by reverse-phase liquid chromatography to give compound 9c.

C. Compound 9c (0.075 g) was dissolved in DCM (3 mL) and one drop of DMF. To this mixture was added oxalyl chloride and the reaction was stirred at rt for 2 h to give compound 9d which was used without further purification.

D. To the reaction mixture of compound 9d dissolved in dichloromethane and DIEA was added amine 8d (1.2 equiv). Upon completion, the reaction was diluted with water and extracted with DCM. The combined organic extracts were dried over Na$_2$SO$_4$, filtered, and concentrated under reduced pressure to afford compound 13.

Using the methods described in the schemes and specific examples, and adaptations thereof, compounds 1 to 87 of Table 1 were prepared.

Formula (Ia)

| Cpd No. | A$_1$ | D | W | L$_2$ | Q |
|---|---|---|---|---|---|
| 1 | 3,4-dichloro-phenyl | 4-methoxy-phenylmethyl | N | —NH(CH$_2$)$_2$— | 1H-benzo imidazol-2-ylamino |
| 2 | 4-fluoro-phenyl | 4-methoxy-phenylmethyl | N | —NH(CH$_2$)$_2$— | 2-amino-imidazol-1-yl |
| 3 | 4-fluoro-phenyl | 4-methoxy-phenylmethyl | N | —NH(CH$_2$)$_2$— | 2-amino-benzoimidazol-1-yl |
| 4 | 4-fluoro-phenyl | 4-methoxy-phenylmethyl | N | —NH(CH$_2$)$_2$— | 2-amino-3H-imidazol-4-yl |
| 5 | 4-fluoro-phenyl | 4-methoxy-phenylmethyl | N | —NH(CH$_2$)$_2$— | 2-amino-5-fluoro-benzoimidazol-1-yl |
| 6 | 4-fluoro-phenyl | 4-methoxy-phenylmethyl | N | —NHCH$_2$— | 2-amino-1H-imidazol-4-yl |
| 7 | 4-fluoro-phenyl | 4-methoxy-phenylmethyl | N | —NH(CH$_2$)$_2$— | 2-amino-6-methyl-benzoimidazol-1-yl |
| 8 | 4-fluoro-phenyl | 4-methoxy-phenylmethyl | N | —NH(CH$_2$)$_2$— | 2-amino-5-trifluoromethyl-benzoimidazol-1-yl |
| 9 | 4-fluoro-phenyl | 4-methoxy-phenylmethyl | N | —NH(CH$_2$)$_2$— | 2-amino-5-methanesulfonyl-benzoimidazol-1-yl |
| 10 | 4-fluoro-phenyl | 4-methoxy-phenylmethyl | N | —NH(CH$_2$)$_2$— | 2-amino-6-chloro-benzoimidazol-1-yl |
| 11 | 4-fluoro-phenyl | 4-methoxy-phenylmethyl | N | —NH(CH$_2$)$_2$— | 2-amino-4-fluoro-benzoimidazol-1-yl |
| 12 | 4-fluoro-phenyl | 4-methoxy-phenylmethyl | N | —NH(CH$_2$)$_2$— | 2-amino-4H-quinazolin-3-yl |
| 13 | 4-methoxy-phenyl | 4-methoxy-phenylmethyl | CH | —C(O)NH(CH$_2$)$_2$— | 2-amino-'benzoimidazol-1-yl |
| 14 | 4-chloro-phenyl | 4-methoxy-phenylmethyl | N | —NH(CH$_2$)$_2$— | 2-amino-benzoimidazol-1-yl |
| 15 | 4-fluoro-phenyl | 4-methoxy-phenylmethyl | N | —NH(CH$_2$)$_2$— | 2-t-butylcarbonylamino-benzoimidazol-1-yl |
| 16 | 4-fluoro-phenyl | 4-methoxy-phenylmethyl | N | —NH(CH$_2$)$_2$— | a mixture of 2-methylamino-benzoimidazol-1-yl and 2-dimethylamino-benzoimidazol-1-yl |
| 17 | 4-fluoro-phenyl | 4-methoxy-phenylmethyl | N | —NH(CH$_2$)$_2$— | 2-trifluoromethylcarbonyl amino-benzoimidazol-1-yl |
| 18 | 4-fluoro-phenyl | 4-methoxy-phenylmethyl | N | —NH(CH$_2$)$_2$— | 2-t-butylcarbonylamino-imidazol-1-yl |
| 19 | 4-fluoro-phenyl | 4-trifluoromethoxy-phenylmethyl | N | —NH(CH$_2$)$_2$— | 2-amino-benzoimidazol-1-yl |
| 20 | 4-fluoro-phenyl | 4-difluoromethoxy-phenylmethyl | N | —NH(CH$_2$)$_2$— | 2-amino-benzoimidazol-1-yl |
| 21 | 4-fluoro-phenyl | 4-fluoro-phenylmethyl | N | —NH(CH$_2$)$_2$— | 2-amino-imidazol-1-yl |
| 22 | 4-fluoro-phenyl | 4-trifluoromethoxy-phenylmethyl | N | —NH(CH$_2$)$_2$— | 2-amino-imidazol-1-yl |
| 23 | 4-fluoro-phenyl | 4-difluoromethoxy-phenylmethyl | N | —NH(CH$_2$)$_2$— | 2-amino-imidazol-1-yl |

| | | | | | |
|---|---|---|---|---|---|
| 24 | 4-fluoro-phenyl | 4-difluoromethoxy-phenylmethyl | N | —NH(CH$_2$)$_2$— | 2-methylcarbonylamino-benzoimidazol-1-yl |
| 25 | 4-fluoro-phenyl | 4-difluoromethoxy-phenylmethyl | N | —NH(CH$_2$)$_2$— | 2-amino-6-fluoro-benzoimidazol-1-yl |
| 26 | 4-fluoro-phenyl | 4-difluoromethoxy-phenylmethyl | N | —NH(CH$_2$)$_2$— | 5-fluoro-2-amino-benzoimidazol-1-yl |
| 27 | 4-fluoro-phenyl | 4-difluoromethoxy-phenylmethyl | N | —NH(CH$_2$)$_2$— | 2-amino-5-trifluoromethyl-benzoimidazol-1-yl |
| 28 | 4-fluoro-phenyl | 4-difluoromethoxy-phenylmethyl | N | —NH(CH$_2$)$_2$— | 2-amino-4,6-difluoro-benzoimidazol-1-yl |
| 29 | 4-fluoro-phenyl | 4-difluoromethoxy-phenylmethyl | N | —NH(CH$_2$)$_2$— | 2-amino-6,7-difluoro-benzoimidazol-1-yl |
| 30 | 4-fluoro-phenyl | 4-difluoromethoxy-phenylmethyl | N | —NH(CH$_2$)$_2$— | 2-amino-6-chloro-benzoimidazol-1-yl |
| 31 | 4-fluoro-phenyl | 4-difluoromethoxy-phenylmethyl | N | —NH(CH$_2$)$_3$— | 2-amino-4-fluoro-benzoimidazol-1-yl |
| 32 | 4-fluoro-phenyl | 4-difluoromethoxy-phenylmethyl | N | —NH(CH$_2$)$_2$— | 2-amino-7-fluoro-benzoimidazol-1-yl |
| 33 | 4-fluoro-phenyl | 4-trifluoromethoxy phenylmethyl | N | —NH(CH$_2$)$_2$— | 2-amino-6-fluoro-benzoimidazol-1-yl |
| 34 | 4-fluoro-phenyl | 4-trifluoromethoxy-phenylmethyl | N | —NH(CH$_2$)$_2$— | 2-amino-5-fluoro-benzoimidazol-1-yl |
| 35 | 4-fluoro-phenyl | 4-trifluoromethoxy-phenylmethyl | N | —NH(CH$_2$)$_2$— | 2-amino-5-trifluoromethyl-benzoimidazol-1-yl |
| 36 | 4-fluoro-phenyl | 4-trifluoromethoxy-phenylmethyl | N | —NH(CH$_2$)$_2$— | 2-amino-4,6-difluoro-benzoimidazol-1-yl |
| 37 | 4-fluoro-phenyl | 4-trifluoromethoxy-phenylmethyl | N | —NH(CH$_2$)$_2$— | 2-amino-6,7-difluoro-benzoimidazol-1-yl |
| 38 | 4-fluoro-phenyl | 4-trifluoromethoxy-phenylmethyl | N | —NH(CH$_2$)$_2$— | 2-amino-6-chloro-benzoimidazol-1-yl |
| 39 | 4-fluoro-phenyl | 4-trifluoromethoxy-phenylmethyl | N | —NH(CH$_2$)$_2$— | 2-amino-4-fluoro-benzoimidazol-1-yl |
| 40 | 4-fluoro-phenyl | 4-trifluoromethoxy-phenylmethyl | N | —NH(CH$_2$)$_2$— | 2-amino-7-fluoro-benzoimidazol-1-yl |
| 41 | 4-fluoro-phenyl | 4-difluoromethoxy-phenylmethyl | N | —NH(CH$_2$)$_4$— | 2-amino-4H-quinazolin-3-yl |
| 42 | 4-fluoro-phenyl | 4-difluoromethoxy-phenylmethyl | N | —NH(CH$_2$)$_2$— | 2-amino-5-chloro-4H-quinazolin-3-yl |
| 43 | 4-fluoro-phenyl | 4-difluoromethoxy-phenylmethyl | N | —NH(CH$_2$)$_2$— | 2-amino-6-chloro-4H-quinazolin-3-yl |
| 44 | 4-fluoro-phenyl | 4-difluoromethoxy-phenylmethyl | N | —NH(CH$_2$)$_2$— | 2-amino-7-chloro-4H-quinazolin-3-yl |
| 45 | 4-fluoro-phenyl | 4-difluoromethoxy-phenylmethyl | N | —NH(CH$_2$)$_2$— | 2-amino-6-fluoro-4H-quinazolin-3-yl |
| 46 | 4-fluoro-phenyl | 4-difluoromethoxy-phenylmethyl | N | —NH(CH$_2$)$_2$— | 2-amino-7-fluoro-4H-quinazolin-3-yl |
| 47 | 4-fluoro-phenyl | 4-trifluoromethoxy-phenylmethyl | N | —NH(CH$_2$)$_2$— | 2-amino-4H-quinazolin-3-yl |
| 48 | 4-fluoro-phenyl | 4-trifluoromethoxy-phenylmethyl | N | —NH(CH$_2$)$_2$— | 2-amino-5-chloro-4H-quinazolin-3-yl |
| 49 | 4-fluoro-phenyl | 4-trifluoromethoxy-phenylmethyl | N | —NH(CH$_2$)$_2$— | 2-amino-6-chloro-4H-quinazolin-3-yl |

-continued

| | | | | | |
|---|---|---|---|---|---|
| 50 | 4-fluoro-phenyl | 4-trifluoromethoxy-phenylmethyl | N | —NH(CH$_2$)$_2$— | 2-amino-7-chloro-4H-quinazolin-3-yl |
| 51 | 4-fluoro-phenyl | 4-trifluoromethoxy-phenylmethyl | N | —NH(CH$_2$)$_2$— | 2-amino-6-fluoro-4H-quinazolin-3-yl |
| 52 | 4-fluoro-phenyl | 4-trifluoromethoxy-phenylmethyl | N | —NH(CH$_2$)$_2$— | 2-amino-7-fluoro-4H-quinazolin-3-yl |
| 53 | 4-fluoro-phenyl | 4-difluoromethoxy-phenylmethyl | N | —NH(CH$_2$)$_2$— | 2-amino-3H-imidazol-4-yl |
| 54 | 4-fluoro-phenyl | 4-trifluoromethoxy-phenylmethyl | N | —NH(CH$_2$)$_2$— | 2-amino-3H-imidazol-4-yl |
| 55 | 4-fluoro-phenyl | 4-difluoromethoxy-phenylmethyl | N | —NH(CH$_2$)$_2$— | 2-amino-4-methoxy-benzoimidazol-1-yl |
| 56 | 4-fluoro-phenyl | 4-difluoromethoxy-phenylmethyl | N | —NH(CH$_2$)$_2$— | 2-amino-6-hydroxy-4H-quinazolin-3-yl |
| 57 | 4-fluoro-phenyl | 4-difluoromethoxy-phenylmethyl | N | —NH(CH$_2$)$_2$— | 2-amino-7-methoxy-4H-quinazolin-3-yl |
| 58 | 4-fluoro-phenyl | 4-difluoromethoxy-phenylmethyl | N | —NH(CH$_2$)$_2$— | 2-amino-4H-quinazolin-1-yl |
| 59 | 3,4-dichloro-phenyl | 4-methoxy-phenylmethyl | N | —NH(CH$_2$)$_2$— | 2-amino-3H-imidazol-4-yl |
| 60 | 4-ethyl-phenyl | 4-methoxy-phenylmethyl | N | —NH(CH$_2$)$_2$— | 2-amino-3H-imidazol-4-yl |
| 61 | 4-methylthio-phenyl | 4-methoxy-phenylmethyl | N | —NH(CH$_2$)$_2$— | 2-amino-3H-imidazol-4-yl |
| 62 | 2,3-dihydro-benzofuran-5-yl | 4-methoxy-phenylmethyl | N | —NH(CH$_2$)$_2$— | 2-amino-3H-imidazol-4-yl |
| 63 | 3,4-dichloro-phenyl | 2,3-dihydro-benzofuran-5-ylmethyl | N | —NH(CH$_2$)$_2$— | 2-amino-3H-imidazol-4-yl |
| 64 | 4-methylthio-phenyl | 2,3-dihydro-benzofuran-5-ylmethyl | N | —NH(CH$_2$)$_2$— | 2-amino-3H-imidazol-4-yl |
| 65 | 4-ethyl-phenyl | 2,3-dihydro-benzofuran-5-ylmethyl | N | —NH(CH$_2$)$_2$— | 2-amino-3H-imidazol-4-yl |
| 66 | 2,3-dihydro-benzofuran-5-yl | 2,3-dihydro-benzofuran-5-ylmethyl | N | —NH(CH$_2$)$_2$—<br>—NH(CH$_2$)$_2$— | 2-amino-3H-imidazol-4-yl |
| 67 | 1-methyl-1H-benzotriazol-5-yl | 4-methoxy-phenylmethyl | N | —NH(CH$_2$)$_2$— | 2-amino-3H-imidazol-4-yl |
| 68 | 1-methyl-1H-benzotriazol-5-yl | 2,3-dihydro-benzofuran-5-yl methyl | N | —NH(CH$_2$)$_2$— | 2-amino-3H-imidazol-4-yl |
| 69 | 3,4-dichloro-phenyl | 4-methoxy-phenylmethyl | N | —NH(CH$_2$)$_2$— | 2-amino-benzoimidazol-1-yl |
| 70 | 4-methylthio-phenyl | 4-methoxy-phenylmethyl | N | —NH(CH$_2$)$_2$— | 2-amino-benzimidazol-1-yl |
| 71 | 4-ethyl-phenyl | 4-methoxy-phenylmethyl | N | —NH(CH$_2$)$_2$— | 2-amino-benzoimidazol-1-yl |
| 72 | 2,3-dihydro-benzofuran-5-yl | 4-methoxy-phenylmethyl | N | —NH(CH$_2$)$_2$— | 2-amino-benzoimidazol-1-yl |
| 73 | 3,4-dichloro-phenyl | 2,3-dihydro-benzofuran-5-yl methyl | N | —NH(CH$_2$)$_2$—<br>—NH(CH$_2$)$_2$— | 2-amino-benzoimidazol-1-yl |
| 74 | 4-methylthio-phenyl | 2,3-dihydro-benzofuran-5-yl methyl | N | —NH(CH$_2$)$_2$— | 2-amino-benzoimidazol-1-yl |
| 75 | 4-ethyl-phenyl | 2,3-dihydro-benzofuran-5-yl methyl | N | —NH(CH$_2$)$_2$— | 2-amino-benzoimidazol-1-yl |

-continued

| # | | | | | |
|---|---|---|---|---|---|
| 76 | 2,3-dihydro-benzofuran-5-yl | 2,3-dihydro-benzofuran-5-yl methyl | N | —NH(CH$_2$)$_2$— | 2-amino-benzoimidazol-1-yl |
| 77 | 1-methyl-1H-benzotriazol-5-yl | 4-methoxy-phenylmethyl | N | —NH(CH$_2$)$_2$— | 2-amino-benzoimidazol-1-yl |
| 78 | 1-methyl-1H-benzotriazol-5-yl | 2,3-dihydro-benzofuran-5-ylmethyl | N | —NH(CH$_2$)$_2$— | 2-amino-benzoimidazol-1-yl |
| 79 | 3,4-dichloro-phenyl | 4-difluoromethoxy-phenylmethyl | N | —NH(CH$_2$)$_2$— | 2-amino-3H-imidazol-4-yl |
| 80 | 4-methylthio-phenyl | 4-difluoromethoxy-phenylmethyl | N | —NH(CH$_2$)$_2$— | 2-amino-3H-imidazol-4-yl |
| 81 | 4-ethyl-phenyl | 4-difluoromethoxy-phenylmethyl | N | —NH(CH$_2$)$_2$— | 2-amino-3H-imidazol-4-yl |
| 82 | 2,3-dihydro-benzofuran-5-yl | 4-difluoromethoxy-phenylmethyl | N | —NH(CH$_2$)$_2$— | 2-amino-3H-imidazol-4-yl |
| 83 | 1-methyl-1H-benzotriazol-5-yl | 4-difluoromethoxy-phenylmethyl | N | —NH(CH$_2$)$_2$— | 2-amino-3H-imidazol-4-yl |
| 84 | 3,4-dichloro-phenyl | 4-difluoromethoxy-phenylmethyl | N | —NH(CH$_2$)$_2$— | 2-amino-benzoimidazol-1-yl |
| 85 | 4-methylthio-phenyl | 4-difluoromethoxy-phenylmethyl | N | —NH(CH$_2$)$_2$— | 2-amino-benzoimidazol-1-yl |
| 86 | 4-ethyl-phenyl | 4-difluoromethoxy-phenylmethyl | N | —NH(CH$_2$)$_2$— | 2-amino-benzoimidazol-1-yl |
| 87 | 2,3-dihydro-benzofuran-5-yl | 4-difluoromethoxy-phenylmethyl | N | —NH(CH$_2$)$_2$— | 2-amino-benzoimidazol-1-yl |

BIOLOGICAL EXAMPLES

Biological Example 1

Expression, Isolation, and Purification of Prokineticin-1

Recombinant N-terminal FLAG-tagged human prokineticin-1 (sequence-MRGATRVSIMLLLVTVSDCDYKD-DDDKAVITGACERDVQCGAGTCCAISLWL RGLRM-CTPLGREGEECHPGSHKVPFFRKRKHHTCPCLPNLL CSRFPDGRYR CSMDLKNINF) was expressed in stably transfected HEK 293 cells.

HEK 293 cells were grown to 100% confluence in DMEM selective high-glucose media (Invitrogen, Carlsbad, Calif.) containing 10% FBS, 20 mM HEPES, sodium pyruvate, penicillin and streptomycin (50 □g/ml each), and G418 (400 mg/L). The DMEM media used to culture the HEK 293 cells was replenished every other day with fresh media over a two-week period of time. Culture media containing the PK-1 peptide was collected, and filtered in 500 mL 0.2 □m pore size filters (Corning Incorporated, Corning, N.Y.). The filtrate was stored in a filtrate bottle at 4° C. The PK-1 peptide containing media was purified by gravity flow passage of media over M2 agarose columns (Sigma Chemical, St. Louis, Mo.) at 4° C. Following media passage, the agarose columns were washed with sterile 1×PBS (pH 7.4) until protein could no longer be detected by OD 280 nm. Columns were then eluted with a 0.1 M glycine-HCl solution at pH 2.8. The eluted material was immediately neutralized, by collecting into tubes containing 1M Tris pH 8. Peak fractions were identified by OD 280 and pooled. The pooled fractions were subjected to Enterokinase cleavage of Flag epitope 4 units/mL overnight at room temperature. Enterokinase was removed, and sample aliquot was stored at −80° C.

Results of Mass Spectral Analysis of Prokineticin 1 Ligand from Above Purification The samples were analyzed using Maldi TOF-MS and LC-Electrospray-Mass Spectral Analysis.
Desired Protein Sequence:

```
AVITGACERDVQCGAGTCCAISLWLRGLRMCTPLGREGEECHPGSHKVPF
FRKRKHHTCPCLPNLLCSRFPDGRYRCSMDLKNINF
```

Calculated Avg. Molecular Mass=9667.4.
MALDI-TOF Analysis
Sample Preparation

The protein sample solution (10 □L) was desalted using a C4 Zip Tip according to the User Guide for Reversed-Phase ZipTip, 2002 Millipore Corporation.
Mass Spectrometry A Micromass TOF Spec E mass spectrometer was used to determine molecular mass. MassLynx software 3.4 was used for the system control and data acquisition. MALDI positive ion mass spectra were acquired over a mass range of 0-80,000 Da. The raw MS data were baseline subtracted and smoothed using Masslynx software and compared to the masses obtained from a reference standard.

Masses of eluting components were calculated using the Agilent deconvolution software.

The mass spectral data shows the presence of the desired protein (molecular mass=9667) and an additional related component with a measured molecular mass of 9172 in about the same abundance based on mass spectral response. This mass agrees, within measurement error, with a possible truncation product missing the last four C-terminal residues indicated below.

Proposed Additional Protein Component Sequence

AVITGACERDVQCGAGTCCAISLWLRGLRMCTPLGREGEEECHPGSHKVPF

FRKRKHHTCPCLPNLLCSRFPDGRYRCSMDLK

Calculated Avg. Molecular Mass=9178.8.

No other related protenaceous components were detected. The mass accuracy for all measurements is approximately 0.1%.

Biological Example 2

Functional Assay

Screening Procedure for PK1 Antagonists on the Fluorometric Imaging Plate Reader (FLIPR)

At a time of 24 h prior to running the assay, in cell culture media (DMEM containing high Glucose and L-glutamine, 10% FBS, 1% Pen/Streptomycin, 1% Sodium Pyruvate, 20 mM HEPES, Zeocin 200 mg/L), 100 μL of 1.3*10$^6$/ml HEK 293 GPR73 (prokineticin 1 receptor) expressing cells were plated in a 96 well poly-d-lysine coated plate (Costar), and incubated at 37° C. and 5% CO$_2$. On the day in which the assay was run, the media was removed and 200 μL of 5× Calcium Plus Dye (Molecular Devices) which was previously resuspended with 200 mL of assay buffer [HBSS w/Ca$^{2+}$ and Mg$^{2+}$ w/o phenol red, 20 mM HEPES, 0.1% BSA, 10 mL probenecid (710 mg probenecid in 5 mL of 1N NaOH, to which was then added 5 mL HBSS containing 20 mM HEPES)] was added to each well of the 96-well plate. The plate was incubated at 37° C. and 5% CO$_2$ for 30 min in dark. The plate was removed and allowed to reach RT for 15 min in the dark. The assay was then run on the FLIPR. In Brief: base line read for 1 min, compound added (25 μL) and incubated for 4 min, 15 seconds, PK1 ligand preparation added (25 μL) for a final concentration of a previously determined EC$_{50}$ and fluorescence was counted for 1 min, 45 seconds. Baseline is described as the amount of relative fluorescence read when buffer alone is added to cells. Baseline was subtracted from all wells. Percent of control was calculated as follows:

> (Baseline subtracted well value is divided by baseline subtracted max value)*100. Percent inhibition is 100 minus the percent of control value.

The IC$_{50}$ is defined as the amount of a given compound required to inhibit 50% of the maximum signal that is generated by the concentration of PK1 preparation used in our assay. IC$_{50}$ values were calculated using GraphPad Prism.

Table 2 includes data generated from the PK1 functional assay described in Example 2.

Biological Data

TABLE 2

| Cpd | Ca$^{2+}$ Mobilization IC50 (μM) | Ca$^{2+}$ Mobilization IC50 (μM) | Ca$^{2+}$ Mobilization % Inh @10 μM | Ca$^{2+}$ Mobilization % Inh @10 μM |
|---|---|---|---|---|
| 1 | >10 | | 40.4 | |
| 2 | 0.019 | 0.005 | 97 | 97 |
| 2 | 0.497 | | 98 | |
| 3 | 0.008 | 0.029 | 96 | 94 |
| 4 | 0.048 | 0.042 | 97 | 96 |
| 5 | 0.069 | | 102 | |
| 6 | 0.322 | | 91 | |
| 7 | 0.123 | | 93 | |
| 8 | 0.163 | | 95 | |
| 9 | 2.29 | | 67 | |
| 10 | 0.155 | | 90 | |
| 11 | 0.146 | | 89 | |
| 12 | 0.028 | | 94 | |
| 13 | 7.39 | | 51 | |
| 14 | 0.077 | | 95 | |
| 15 | 0.797 | | 93 | |
| 16* | >10 | | 42 | |
| 17 | 0.419 | | 96 | |
| 18 | 0.106 | | 99 | |
| 19 | 0.104 | 0.212 | 102 | 100 |
| 20 | 0.053 | 0.052 | 103 | 101 |
| 21 | >10 | | 37 | |
| 22 | 0.061 | | 100 | |
| 23 | 0.028 | 0.057 | 100 | 97 |
| 24 | 7.91 | | 47 | |
| 25 | 0.17 | | 87 | |
| 26 | 0.081 | 0.015 | 92 | 88 |
| 27 | 0.31 | | 85 | |
| 28 | >10 | | 39 | |
| 29 | 0.406 | | 83 | |
| 30 | 0.252 | | 86 | |
| 31 | 1.28 | | 67 | |
| 32 | 0.132 | | 94 | |
| 33 | 0.323 | | 93 | |
| 34 | 0.363 | | 87 | |
| 35 | 5.01 | | 59 | |
| 36 | 8.24 | | 50 | |
| 37 | 2.2 | | 72 | |
| 38 | 0.67 | | 84 | |
| 39 | 0.38 | | 80 | |
| 40 | 0.969 | | 91 | |
| 41 | 0.129 | | 101 | |
| 42 | 0.063 | | 101 | |
| 43 | 0.111 | | 101 | |
| 44 | 0.118 | | 103 | |
| 45 | 0.092 | | 101 | |
| 46 | 0.061 | | 101 | |
| 47 | 0.123 | | 100 | |
| 48 | 0.116 | | 101 | |
| 49 | 0.233 | | 103 | |
| 50 | 0.332 | | 99 | |
| 51 | 0.996 | | 99 | |
| 52 | 0.359 | | 104 | |
| 53 | 0.036 | 0.015 | 93 | 100 |
| 54 | 0.027 | 0.097 | 96 | 95 |
| 54 | 0.183 | | 91 | |
| 55 | 0.233 | | 91 | |
| 56 | 0.161 | | 100 | |
| 57 | 0.144 | | 95 | |
| 58 | 0.171 | | 96 | |
| 59 | 0.049 | | 96 | |
| 60 | 0.295 | | 85 | |
| 61 | 0.021 | 0.019 | 101 | 102 |
| 62 | 0.241 | | 97 | |
| 63 | 2.01 | | 54 | |
| 64 | 0.17 | | 93 | |
| 65 | >10 | | 35 | |
| 66 | 2.42 | | 69 | |
| 67 | 0.171 | | 93 | |
| 68 | 1.41 | | 78 | |
| 69 | 0.066 | | 102 | |
| 70 | 0.022 | | 103 | |

TABLE 2-continued

| Cpd | Ca$^{2+}$ Mobilization IC50 (μM) | Ca$^{2+}$ Mobilization IC50 (μM) | Ca$^{2+}$ Mobilization % Inh @10 μM | Ca$^{2+}$ Mobilization % Inh @10 μM |
|---|---|---|---|---|
| 71 | 0.09 | | 101 | |
| 72 | 0.058 | | 102 | |
| 73 | 0.186 | | 90 | |
| 74 | 0.034 | | 102 | |
| 75 | 0.507 | | 83 | |
| 76 | 0.225 | | 97 | |
| 77 | 0.055 | | 99 | |
| 78 | 0.066 | 0.13 | 102 | 104 |
| 79 | 0.102 | | 96 | |
| 80 | 0.032 | | 98 | |
| 81 | 0.502 | | 90 | |
| 82 | 0.202 | | 96 | |
| 83 | 0.224 | | 98 | |
| 84 | 0.345 | | 97 | |
| 85 | 0.157 | | 99 | |
| 86 | 0.337 | | 94 | |
| 87 | 0.223 | | 102 | |

*Compound 16 was tested as a mixture of two compounds, as described in Table 1, hereinabove.

Biological Example 3

Effect of PK1 on Secretion and Gut Mucosal Ion Transport in Mammals

Methodology. Segments of ileum starting at a point 2 cm proximal to the ileocecal junction and extending 10 cm proximally were freshly excised, placed into Krebs-Ringer bicarbonate (KRB) solution, and emptied of their contents as a plastic rod was gently inserted into the intact segment. Ileal segments were scored with the back-edge of scalpel blade along the entire mesenteric border, and the intact muscular layers including the myenteric plexus were carefully removed with flat-head forceps. Three rectangular tissue sheets approximately 1.5 cm in length were prepared from the remaining muscle-stripped, mucosa-submucosa tissues and cut with care taken to avoid Peyer's patches. Each tissue sheet containing intact submucosal ganglia was pinned over a rectangular portal (total cross-sectional area of exposed mucosa=0.50 cm$^2$) between halves of an acrylic mounting cassette that was inserted between the tissue-bathing reservoirs of a modified Ussing-type flux chamber (Physiologic Instruments, Inc., San Diego, Calif.).

The apical (i.e., mucosal) and basolateral (i.e., serosal) surface of each tissue was bathed with 6 ml of an oxygenated KRB solution maintained at 36° C. Once mounted, tissues were allowed to equilibrate for 0.5-1 h before electrical field stimulation and addition of secretagogues or drugs. The KRB solution contained (in mM) 120 NaCl, 6 KCl, 1.2 MgCl$_2$, 1.2 NaH$_2$PO$_4$, 14.4 NaHCO$_3$, 2.5 CaCl$_2$, and 11.5 glucose or 11.5 mannitol. The KRB solution was continuously aerated with 95% O$_2$: 5% CO$_2$ and maintained at pH 7.3. Each chamber was equipped with a pair of saturated KCl-agar bridges for measurement of transmural electrical potential difference (PD) across the tissue, and a pair of Ag—AgCl agar electrodes connected to an automated voltage-clamp device (model VCC MC6, or model VCC MC8, Physiologic Instruments, Inc., San Diego, Calif.) that compensated for solution resistance between the PD-sensing bridges and for deviations detected from a transmural potential difference (PD) across the tissues that were clamped at 0 mV. Tissue conductance (G) was calculated (in mS) by determining the current necessary to change PD by 1 mV using bipolar pulses from a pulse generator. Short-circuit current (Isc in μA), an index of net active ion transport, was measured continuously. Tissue conductance (Gt in mS), an index of the barrier function to passive flow of ions, was calculated from changes in Isc and the transepithelial potential difference for each tissue.

Baseline recordings of short-circuit current (Isc) and G for each tissue were acquired and recorded for an additional 15 min period prior to the start of an experimental protocol. Stimulated changes in Isc were measured and recorded continuously with a computerized data acquisition system (PowerLab 8SP, ADInstruments, Inc., Colorado Springs, Colo.). Neurally-evoked changes in Isc were obtained by application of electrical field stimulation (80V, 0.5 ms, 10 Hz, 5 s) from the outputs of an electronic stimulator (S-48, Grass-Telefactor, Astro-Med, Inc., West Warwick, R.I.) attached via aluminum foil electrodes placed in direct contact with the mucosal surface at opposite poles of each tissue. Pharmacological agents and secretagogues were routinely added to the basolateral-side reservoir. Agonist or secretagogue effects on Isc were continuously recorded following basolateral addition. Concentration-response curves were constructed from the cumulative, step-wise addition of pre-determined increasing amounts of agonist or secretagogue that were added at or near the peak Isc response to the preceding lower concentration. Effects of antagonists or inhibitors of secretion were evaluated after a 10-20 minute exposure period that was followed by challenge with a specific agonist or secretagogue.

Statistical Analysis. All values are reported as means+SE. Electrophysiological data obtained with Ussing flux-type chambers were normalized to tissue surface area and expressed per cm$^2$. Stimulated changes in ion transport were determined as the absolute difference between a baseline value prior to stimulation and the maximal response (ΔIsc) evoked by a given stimulus or secretagogue. An estimated EC$_{50}$ for the stimulatory action of PK1 on epithelial secretion was determined from a 7-point cumulative concentration-response test using a computer calculated curve-fitting function in PRISM (GraphPad Software, Inc.). An unpaired, two-tailed Student's t-test was used to determine statistical significance between any two groups, e.g., control and experimental tissues. An ANOVA in conjunction with a post hoc Neuman-Keuls multiple comparisons test was used to determine significant differences among multiple groups. P<0.05 was considered statistically significant.

Figure 2:
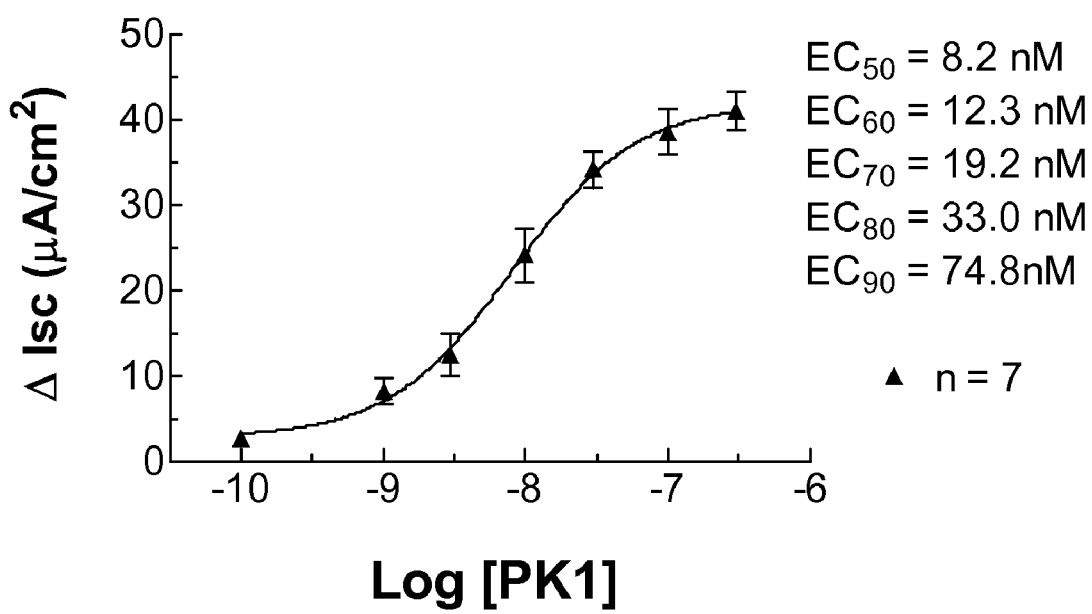
FIG. 2 shows a cumulative concentration-response curve evoked in the short-circuit current (Isc) response to PK1 peptide in PK1 exposed rat ileal tissues mounted in Ussing-type ion flux chambers.

Summary of results. The basal Isc was 35.2±2.4 μA/cm$^2$ and tissue conductance (G) was 33.7±0.9 mS/cm$^2$ (n=79 tissues from 34 rats). Following a single-dose addition of PK1 to the Krebs solution bathing the basolateral tissue surface, Isc gradually increased to a peak value within 2-4 min and then declined back toward baseline within 10-15 min. The PK1-evoked increases in Isc were concentration dependent with an EC$_{50}$ of approximately 8.2 nM determined from cumulative concentration-response studies (see FIG. 2). Cumulative concentration-response curve evoked in the short-circuit current (Isc) response to Prokineticin 1 (PK1) peptide in PK1 exposed rat ileal tissues mounted in Ussing-type ion flux chambers. Change in Isc is reported as the difference between the peak Isc response to PK1 at a given concentration compared to the initial baseline (unstimulated) Isc value and expressed as ΔIsc measured in microAmps (μA) corrected for the surface area (in cm$^2$) of the tissue mounted in the Ussing-type chamber. An EC$_{50}$ value for the response curve was calculated as described below in methodology. The maximal response for the PK1-evoked response occurred at 100 nM; 100 nM PK1 evoked an increase in Isc of 28.7±2.9 μA/cm$^2$ from baseline (n=42 tissues from 29 rats) and 10 nM PK1 evoked an increase of 13.5±2. μA/cm² (n=33 tissues from 22 rats). The concentrations of 10 nM and 100 nM were used in all subsequent studies. PK1 had no significant effect on G in any of our studies. The pro-secretory effect of PK1 was not blocked in the presence of the nerve conduction toxin, Tetrodotoxin (TTX), or blockade of muscarinic receptors present on mucosal enterocytes by the anti-cholinergic drug, Atropine, indicating that the its action is not dependent on intrinsic neural activity in the tissues. The PK1 evoked increase in Isc requires the presence of endogenous PK1 receptors since exogenous PK1 peptide added to ileum mucosal tissues from PK1 receptor knock-out mice failed to elicit a significant change in Isc compared to wild-type littermates.

Biological Example 4

Small Molecule PK1 Receptor Antagonists are Effective at Suppressing Both PK1 and Cholera Toxin Stimulated Gut Secretion in Rat Ileum Methodology. The basic methodology for Ussing-type ion flux chambers used in these studies was the same as that described in detail above with the following modifications to the experimental protocol. Following a 30-45 minute equilibration period, baseline-stable tissues were subjected to a train of electrical field stimulation (EFS; 80 V, 0.5 ms, 10 Hz, 5 s) applied from contacts connecting the foil electrodes on opposite poles of the tissue to the polarized, isolated outputs from an electronic square-pulse stimulator. The responses to two sequential EFS were used to gauge tissue viability and comparability of the responses of individual tissues from each rat and between rats. Tissue conductance was measured at periodic intervals as changes in the amplitudes of brief short-circuit current responses evoked by application of 1 mV amplitude bi-polar pulses from a pulse generator using Ohm's Law. Three to four tissues from each rat were studied. The tissues from a given animal were grouped and assigned accordingly: one control tissue which received only vehicle followed by two consecutive doses of PK-1 ligand added in a cumulative fashion to the basolateral surface of the tissue; the remaining two to three tissues from the same animal were assigned to be exposed to a given PK-1 receptor antagonist (e.g., 3-4 tissues from 1 rat: Control, Antagonist₁, Antagonist₂, and/or Antagonist₃). Test compound was added to the basolateral tissue side reservoir at a final concentration of 1 μM and allowed a 15 minute incubation period prior to challenge with the PK1 peptide. At the end of this 15 min exposure period, PK1 ligand at 10 and 100 nM was added in a cumulative fashion to each tissue to characterize the inhibitory effect of the test compound. At the conclusion of the experiment, EFS was re-applied to gauge tissue viability and stability of responsiveness.

For the Cholera toxin studies, paired mucosal tissues were obtained from each rat and mounted in Ussing-type chambers. Following tissue equilibration, baseline-stable and conductance-stable tissues were exposed to 1 μg/ml Cholera toxin (i.e., one tissue from each pair) added to the mucosa together with simultaneous addition of DMSO vehicle or Compound 3 of the present invention (i.e., one tissue from each pair) to the serosa at a final concentration of 10 μM to start the experiment. From this point on, baseline Isc and periodic assessment of tissue conductance were monitored and recorded for up to 4 hours.

Figure 3:
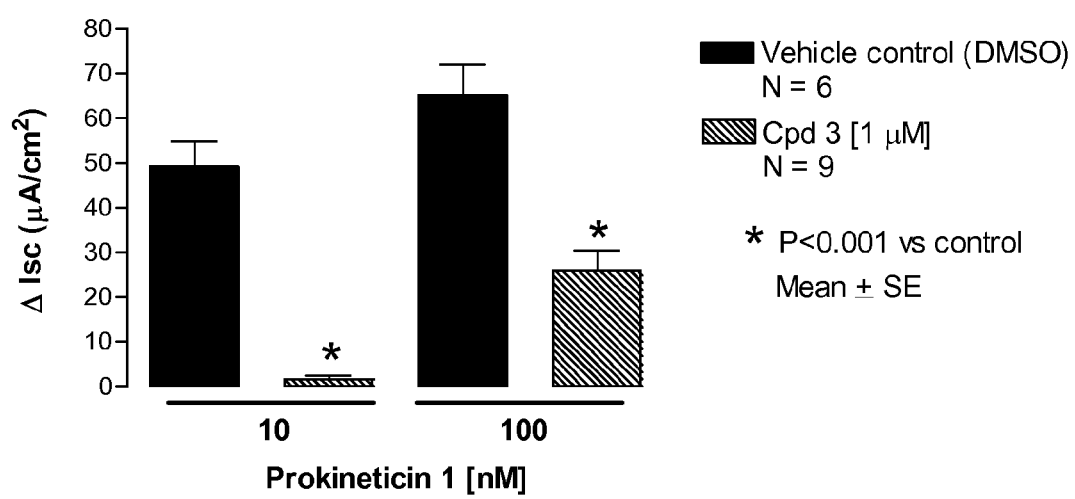
FIG. 3 is a graphical representation that shows that Compound 3 of the present invention suppresses the PK1-evoked stimulation of gut secretion in rat ileum, without inhibiting the stimulatory action of an unrelated secretagogue.
Figure 4:
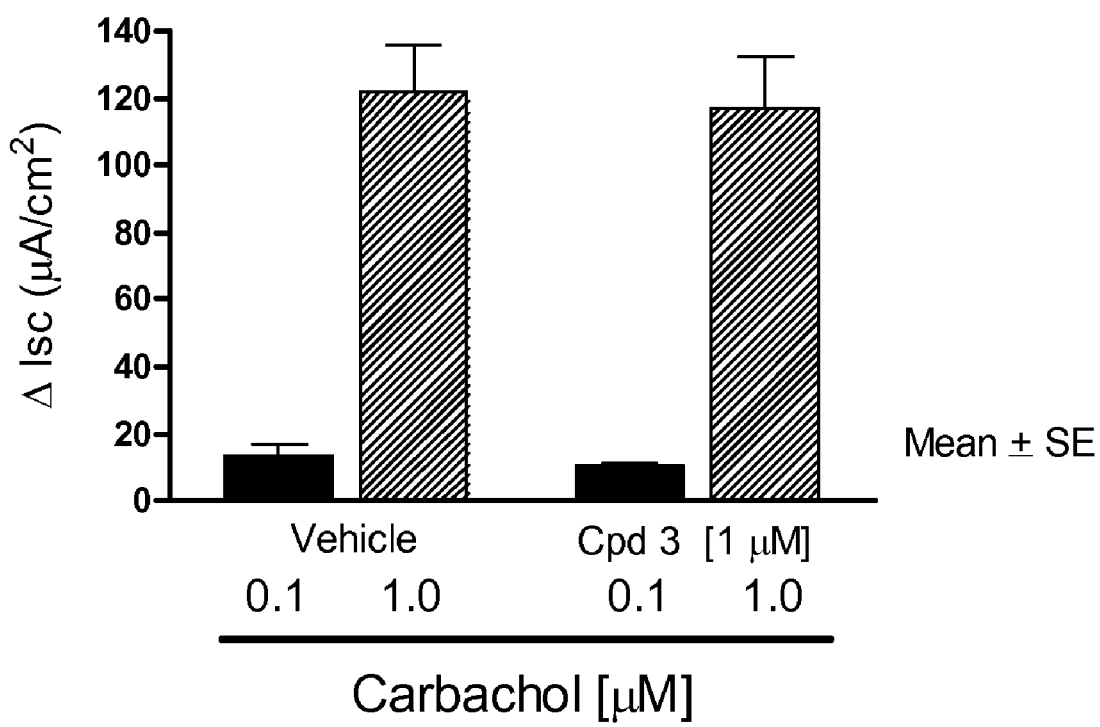
FIG. 4 is a graphical representation that shows that Compound 3 of the present invention suppresses the Cholera toxin-evoked stimulation of gut secretion in rat ileum, without inhibiting the stimulatory action of an unrelated secretagogue.

Summary of results. Pre-treatment of tissues with PK1 antagonists alone had no measurable effect on baseline Isc and tissue conductance (G). The results indicate that suppression of the PK1 evoked increase in Isc in isolated rat ileum mucosa was successfully achieved in the presence of Compound 3 of the present invention, which was identified using a functional cell based screening assay (i.e., mobilization of intracellular $Ca^{2+}$) as a putative antagonist at the PK1 receptor. In trials with this compound, the observed suppression of the Isc response evoked by two ascending cumulative concentrations of PK1 showed characteristics of a significant surmountable antagonism (see FIG. 3). The PK1 evoked increase in Isc was suppressed by Cpd 3, a small molecule antagonist at the PK1 receptor. These data strongly suggest that good efficacy can be achieved in the selective functional blockade of the PK1 receptor by this small molecule inhibitor to modulate the pro-secretory effect of PK1 on the intestinal epithelium. The selectivity of the functional blockade of the PK1 receptor by Compound 3 was confirmed by testing this compound against an unrelated cholinergic secretagogue, carbachol. Compound 3 failed to suppress the pro-secretory effect of carbachol tested at two different concentrations added in an ascending cumulative fashion to the serosal side of each tissue in the Ussing-type flux chambers (see FIG. 4). Increased Isc evoked in response to the cholinergic agonist Carbachol was not suppressed by Compound 3, a small molecule antagonist at the PK1 receptor.

Figure 5:
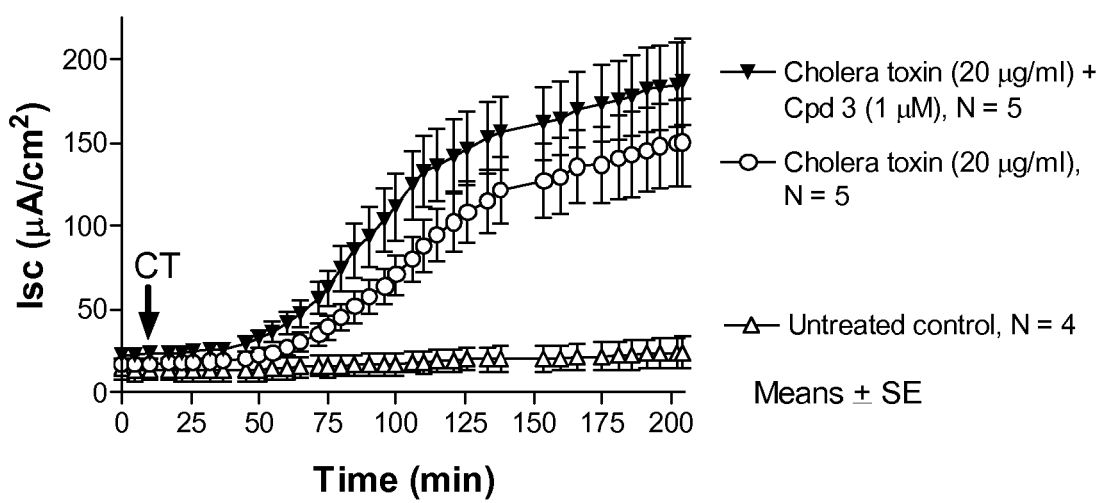
FIG. 5 shows that Compound 3 of the present invention suppresses *Vibrio cholera* toxin induced increased in baseline Isc of muscle-stripped rat ileum mucosa.

To investigate the potential anti-secretory efficacy of selective small molecule PK1 receptor antagonists, we established a model of secretory diarrhea ex vivo in the Ussing-type flux chambers with mucosal exposure to Cholera toxin. Mucosal application of Cholera toxin mimics the route of exposure for this disease-causing agent in animals and man. Pre-treatment of isolated rat ileum mucosa with Compound 3 (10 μM added to the serosa), did significantly suppress the sustained increase in baseline Isc over time evoked by 1 μg/ml Cholera toxin added to the mucosa by approximately 50-60% (see FIG. 5). Compound 3 (1 μM), had no significant effect versus the increased baseline short-circuit current (Isc) evoked by *Vibrio cholera* toxin (20 μg/ml) added to the mucosal surface of muscle-stripped rat ileum. These data suggest the potential for the efficacious use of PK1 receptor antagonists from this chemical class in gut disease states that have a significant secretory diarrhea component.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

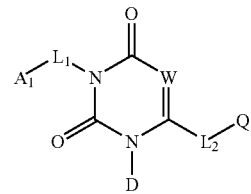

Formula (I)

wherein:
A₁ is hydrogen, $C_{1-4}$alkoxy, aryl, aryloxy, optionally benzofused heterocyclyl, or an optionally benzofused heteroaryl;
and aryl, aryloxy, heteroaryl, heterocyclyl, the benzo portion of benzofused heterocyclyl, and benzofused heteroaryl are optionally substituted with a substituent selected from the group consisting of $C_{1-6}$alkyl, hydroxyl($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, $C_{1-6}$alkylamino, di($C_{1-6}$alkyl)amino, cyano, hydroxyl, aminocarbonyl, $C_{1-6}$alkylaminocarbonyl, di($C_{1-6}$alkyl)aminocarbonyl, $C_{1-6}$alkoxycarbonylamino, $C_{1-6}$alkylcarbonyl, $C_{1-6}$alkylthiocarbonyl, formyl, $C_{1-6}$alkylsulfonyl, $C_{1-6}$alkylsulfonylamino, aminosulfonyl, $C_{1-6}$alkylaminosulfonyl, and di($C_{1-6}$alkyl)aminosulfonyl; and wherein aryl, aryloxy, heteroaryl, heterocyclyl, the benzo portion of benzofused heterocyclyl, and benzofused heteroaryl are optionally further substituted with one to two substituents independently selected from the group consisting of $C_{1-4}$alkyl, $C_{1-4}$alkoxy, halogen, and hydroxyl; provided that $A_1$ is other than 3,5-di-t-butyl-phenyl;

$L_1$ is —$(CH_2)_r$—, —$CH_2C_{2-4}$alkenyl-, or —$CH_2CH_2X(CH_2)_s$—, wherein $L_1$ is optionally substituted with one to two substituents independently selected from the group consisting of $C_{1-6}$alkyl, $C_{2-6}$alkenyl, $C_{2-6}$alkynyl, and halogen; and, r is an integer of 1 to 5; such that r is greater than or equal to 4 when $A_1$ is $C_{1-4}$alkoxy;

s is an integer of 1 to 3;

X is O or S;

D is —P-$A_2$;

wherein P is —$(CH_2)_{1-2}$— or —$CH_2CH=CH$— when $A_2$ is phenyl, optionally benzofused heterocyclyl, optionally benzofused heteroaryl, or $C_{3-8}$cycloalkyl; alternatively, P is —$(CH_2)_{3-6}$—, when $A_2$ is hydrogen, $C_{1-4}$alkoxy, or $C_{1-4}$alkoxycarbonyl; and wherein P is optionally substituted with one to two substituents independently selected from the group consisting of $C_{1-6}$alkyl, $C_{2-6}$alkenyl, $C_{2-6}$alkynyl, and halogen;

$A_2$ is hydrogen; dihydrobenzofuranyl; heteroaryl other than unsubstituted hydroxyl-2-yl; $C_{3-8}$cycloalkyl; or phenyl optionally substituted at the meta and para positions with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, $C_{1-6}$alkylamino, di($C_{1-6}$alkyl)amino, cyano, hydroxyl, nitro, $C_{1-6}$alkylcarbonyl, $C_{1-6}$alkylthiocarbonyl, aminocarbonyl, $C_{1-6}$alkylaminocarbonyl, di($C_{1-6}$alkyl)aminocarbonyl, $C_{1-6}$alkylcarbonylamino, and a non fused $C_{3-6}$cycloalkyloxy; wherein dihydrobenzofuranyl, heteroaryl, and $C_{3-8}$cycloalkyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl ($C_{1-6}$)alkoxy, phenyl, $C_{1-6}$alkylthio, $C_{1-6}$alkoxycarbonyl, amino, $C_{1-6}$alkylamino, di($C_{1-6}$alkyl)amino, cyano, hydroxyl, nitro, $C_{1-6}$alkylcarbonyl, $C_{1-6}$alkylthiocarbonyl, aminocarbonyl, $C_{1-6}$alkylaminocarbonyl, di($C_{1-6}$alkyl)aminocarbonyl, $C_{1-6}$alkylcarbonylamino, and a non fused $C_{3-6}$cycloalkyloxy;

provided that no more than two substituents on $A_2$ are aryl($C_{1-6}$)alkoxy, phenyl, or a non fused $C_{3-6}$cycloalkyloxy;

such that both $A_1$ and $A_2$ are not 4-fluoro-phenyl when $L_1$ and $L_2$ are both —$CH_2$— and Q is a substituent of formula $Q_1$;

W is N;

$L_2$ is a bivalent radical selected from the group consisting of pyrrolidinyl or piperidinyl attached to the W-containing ring of Formula (I) via its nitrogen atom, wherein said pyrrolidinyl or piperidinyl is substituted on a carbon atom with —$(CH_2)_{0-2}$—;

—NH—$C_{5-7}$cycloalkyl-$(CH_2)_{0-2}$—; such that when $C_{5-7}$cycloalkyl is cyclohexyl, Q is attached at either the 2- or cis-4-position relative to the position of —NH—;

—C(=O)NH($CR^yR^z$)$_{2-5}$—;

and

—NH—CH($R^x$)—($CR^yR^z$)$_{1-5}$—;

$R^x$, $R^y$, and $R^z$ are independently H or $C_{1-4}$alkyl;

and provided that $L_2$ in any instance does not exceed 7 atoms in length;

such that Q is selected from the group consisting of $Q_1$, $Q_2$, $Q_4$, and $Q_6$ when $L_2$ is other than —NH—CH($R^x$)—($CR^yR^z$)$_{1-5}$;

Q is

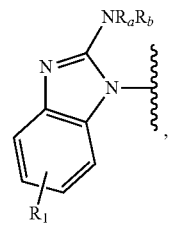

$Q_1$

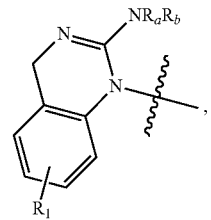

$Q_2$

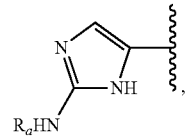

$Q_3$

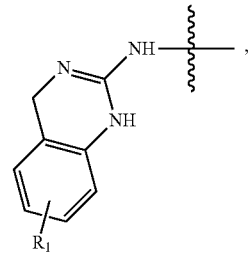

$Q_4$

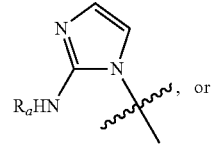

$Q_5$, or

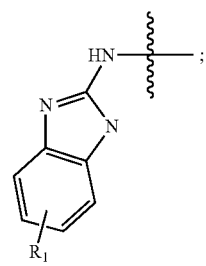

$Q_6$ wherein the benzo portion of $Q_1$, $Q_2$, $Q_4$ and $Q_6$ is optionally substituted with $R_1$;

$R_1$ is one to two substituents independently selected from the group consisting of hydrogen, methyl, fluro, chloro and trifluoromethyl;

$R_a$ and $R_b$ are independently hydrogen, trifluoromethylcarbonyl, $C_{1-4}$alkylcarbonyl, and methyl;

or an enantiomer, a diastereomer, or a pharmaceutically acceptable salt thereof.

2. A compound of Formula (I)

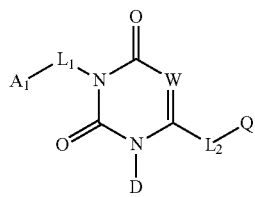

Formula (I)

wherein:

$A_1$ is hydrogen, $C_{1-4}$alkoxy, aryl, aryloxy, optionally benzofused heterocyclyl, or an optionally benzofused heteroaryl;

and aryl, aryloxy, heteroaryl, heterocyclyl, the benzo portion of benzofused heterocyclyl, and benzofused heteroaryl are optionally substituted with a substituent selected from the group consisting of $C_{1-6}$alkyl, hydroxyl($C_{1-6}$)alkyl, $C_{1-6}$alkoxy, halogen, nitro, halogenated $C_{1-6}$alkyl, halogenated $C_{1-6}$alkoxy, $C_{1-6}$alkylthio, $C_{1-6}$alkoxycarbonyl, amino, $C_{1-6}$alkylamino, di($C_{1-6}$alkyl)amino, cyano, hydroxyl, aminocarbonyl, $C_{1-6}$alkylaminocarbonyl, di($C_{1-6}$alkyl)aminocarbonyl, $C_{1-6}$alkoxycarbonylamino, $C_{1-6}$alkylcarbonyl, $C_{1-6}$alkylthiocarbonyl, formyl, $C_{1-6}$alkylsulfonyl, $C_{1-6}$alkylsulfonylamino, aminosulfonyl, $C_{1-6}$alkylaminosulfonyl, and di($C_{1-6}$alkyl)aminosulfonyl; and wherein aryl, aryloxy, heteroaryl, heterocyclyl, the benzo portion of benzofused heterocyclyl, and benzofused heteroaryl are optionally further substituted with one to two substituents independently selected from the group consisting of $C_{1-4}$alkyl, $C_{1-4}$alkoxy, halogen, and hydroxyl; provided that $A_1$ is other than 3,5-di-t-butyl-phenyl;

$L_1$ is —$(CH_2)_r$—, —$CH_2C_{2-4}$alkenyl-, or —$CH_2CH_2X$$(CH_2)_s$—, wherein $L_1$ is optionally substituted with one to two substituents independently selected from the group consisting of $C_{1-6}$alkyl, $C_{2-6}$alkenyl, $C_{2-6}$alkynyl, and halogen; and, r is an integer of 1 to 5; such that r is greater than or equal to 4 when $A_1$ is $C_{1-4}$alkoxy;

s is an integer of 1 to 3;

X is O or S;

D is —P-$A_2$;

wherein P is —$(CH_2)_{1-2}$— or —$CH_2CH$=$CH$— when $A_2$ is phenyl, optionally benzofused heterocyclyl, optionally benzofused heteroaryl, or $C_{3-8}$cycloalkyl; alternatively, P is —$(CH_2)_{3-6}$—, when $A_2$ is hydrogen, $C_{1-4}$alkoxy, or $C_{1-4}$alkoxycarbonyl; and wherein P is optionally substituted with one to two substituents independently selected from the group consisting of $C_{1-6}$alkyl, $C_{2-6}$alkenyl, $C_{2-6}$alkynyl, and halogen;

$A_2$ is hydrogen; dihydrobenzofuranyl; heteroaryl other than unsubstituted hydroxyl-2-yl; $C_{3-8}$cycloalkyl; or phenyl optionally substituted at the meta and para positions with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, $C_{1-6}$alkylamino, di($C_{1-6}$alkyl)amino, cyano, hydroxyl, nitro, $C_{1-6}$alkylcarbonyl, $C_{1-6}$alkylthiocarbonyl, aminocarbonyl, $C_{1-6}$alkylaminocarbonyl, di($C_{1-6}$alkyl)aminocarbonyl, $C_{1-6}$alkylcarbonylamino, and a non fused $C_{3-6}$cycloalkyloxy; wherein dihydrobenzofuranyl, heteroaryl, and $C_{3-8}$cycloalkyl are optionally substituted with one to three substituents independently selected from the group consisting of $C_{1-6}$alkyl, $C_{1-6}$alkoxy, halogen, halogenated $C_{1-6}$alkyl, halogenated $C_{1-6}$alkoxy, aryl($C_{1-6}$)alkoxy, phenyl, $C_{1-6}$alkylthio, $C_{1-6}$alkoxycarbonyl, amino, $C_{1-6}$alkylamino, di($C_{1-6}$alkyl)amino, cyano, hydroxyl, nitro, $C_{1-6}$alkylcarbonyl, $C_{1-6}$alkylthiocarbonyl, aminocarbonyl, $C_{1-6}$alkylaminocarbonyl, di($C_{1-6}$alkyl)aminocarbonyl, $C_{1-6}$alkylcarbonylamino, and a non fused $C_{3-6}$cycloalkyloxy;

provided that no more than two substituents on $A_2$ are aryl($C_{1-6}$)alkoxy, phenyl, or a non fused $C_{3-6}$cycloalkyloxy;

such that both $A_1$ and $A_2$ are not 4-fluoro-phenyl when $L_1$ and $L_2$ are both —$CH_2$— and Q is a substituent of formula $Q_1$;

W is N;

$L_2$ is a bivalent radical selected from the group consisting of pyrrolidinyl or piperidinyl attached to the W-containing ring of Formula (I) via its nitrogen atom, wherein said pyrrolidinyl or piperidinyl is substituted on a carbon atom with —$(CH_2)_{0-2}$—;

—NH—$C_{5-7}$cycloalkyl-$(CH_2)_{0-2}$—; such that when $C_{5-7}$cycloalkyl is cyclohexyl, Q is attached at either the 2- or cis-4-position relative to the position of —NH—; —$C(=O)NH(CR^yR^z)_{2-5}$—;

and

—NH—$CH(R^x)$—$(CR^yR^z)_{1-5}$;

$R^x$, $R^y$, and $R^z$ are independently H or $C_{1-4}$alkyl;

and provided that $L_2$ in any instance does not exceed 7 atoms in length;

such that Q is selected from the group consisting of $Q_1$, $Q_2$, $Q_4$, and $Q_6$ when $L_2$ is other than —NH—$CH(R^x)$—$(CR^yR^z)_{1-5}$—;

Q is

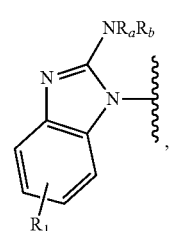

$Q_1$

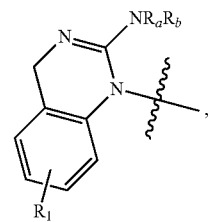

$Q_2$

-continued

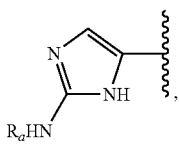,

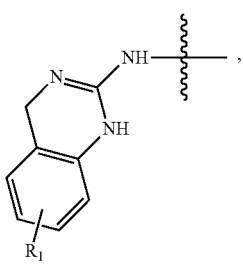,

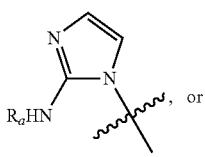, or

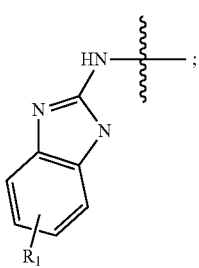;

wherein the benzo portion of $Q_1$, $Q_2$, $Q_4$ and $Q_6$ is optionally substituted with $R_1$;

$R_1$ is one to two substituents independently selected from hydrogen, fluoro, or chloro;

$R_a$ and $R_b$ are independently hydrogen, trifluoromethylcarbonyl, $C_{1-4}$alkylcarbonyl, and methyl;

or an enantiomer, a diastereomer, or a pharmaceutically acceptable salt thereof.

3. A pharmaceutical composition comprising a compound or salt according to claim 1 admixed with a pharmaceutically acceptable carrier, excipient, or diluent.

4. A pharmaceutical composition comprising a compound or salt according to claim 2 admixed with a pharmaceutically acceptable carrier, excipient, or diluent.

5. A method of treating a gastrointestinal (GI) disease or condition in a mammal in which the gastrointestinal (GI) disease or condition selected from the group consisting of irritable bowel syndrome (IBS, including diarrhea-predominant, as well as alternating diarrhea/constipation forms of IBS), inflammatory bowel disease (IBD, including ulcerative colitis, and Crohn's disease), and GERD and secretory bowel disorders induced by pathogens comprising administering to a patient in need thereof a therapeutically effective amount of a compound of claim 1.

6. A method of treating a gastrointestinal (GI) disease or condition in a mammal in which the gastrointestinal (GI) disease or condition selected from the group consisting of irritable bowel syndrome (IBS, including diarrhea-predominant, as well as alternating diarrhea/constipation forms of IBS), inflammatory bowel disease (IBD, including ulcerative colitis, and Crohn's disease), and GERD and secretory bowel disorders induced by pathogens comprising administering to a patient in need thereof a therapeutically effective amount of a compound of claim 2.

* * * * *